United States Patent
Kim et al.

(10) Patent No.: US 11,918,634 B2
(45) Date of Patent: Mar. 5, 2024

(54) METHOD FOR ACTIVATING T CELLS FOR CANCER TREATMENT

(71) Applicant: GOOD T CELLS, INC., Seoul (KR)

(72) Inventors: Jung Ho Kim, Seoul (KR); Beom Seok Kim, Seoul (KR)

(73) Assignee: GOOD T CELLS, INC., Seoul (KR)

( * ) Notice: Subject to any disclaimer, the term of this patent is extended or adjusted under 35 U.S.C. 154(b) by 770 days.

(21) Appl. No.: 16/638,055

(22) PCT Filed: Aug. 10, 2018

(86) PCT No.: PCT/KR2018/009224
§ 371 (c)(1),
(2) Date: Jun. 25, 2020

(87) PCT Pub. No.: WO2019/031938
PCT Pub. Date: Feb. 14, 2019

(65) Prior Publication Data
US 2021/0009952 A1 Jan. 14, 2021

(30) Foreign Application Priority Data

Aug. 10, 2017 (KR) .................. 10-2017-0101800

(51) Int. Cl.
| | | |
|---|---|---|
| *A61K 35/17* | (2015.01) | |
| *A61P 35/00* | (2006.01) | |
| *A61K 39/00* | (2006.01) | |
| *C12N 5/0783* | (2010.01) | |
| *A61K 38/16* | (2006.01) | |
| *A61K 38/17* | (2006.01) | |
| *C12N 15/869* | (2006.01) | |

(52) U.S. Cl.
CPC .......... *A61K 39/0011* (2013.01); *A61K 35/17* (2013.01); *A61K 38/162* (2013.01); *A61K 38/1774* (2013.01); *C12N 5/0636* (2013.01); *C12N 15/869* (2013.01); *C12N 2501/22* (2013.01); *C12N 2501/2302* (2013.01); *C12N 2501/2304* (2013.01); *C12N 2501/2307* (2013.01); *C12N 2501/2312* (2013.01); *C12N 2501/2315* (2013.01); *C12N 2501/2321* (2013.01); *C12N 2501/24* (2013.01); *C12N 2501/25* (2013.01); *C12N 2502/1107* (2013.01); *C12N 2502/1114* (2013.01); *C12N 2502/1121* (2013.01); *C12N 2502/1157* (2013.01)

(58) Field of Classification Search
CPC .. A61K 39/0011; A61K 35/17; A61K 38/162; C12N 5/0636; C12N 2502/1107; C12N 2502/1114; C12N 2502/1121; C12N 2502/1157; A61P 35/00
USPC ..................................................... 424/93.21
See application file for complete search history.

(56) References Cited

U.S. PATENT DOCUMENTS

| | | |
|---|---|---|
| 6,037,135 A | 3/2000 | Kubo et al. |
| 2010/0135994 A1 | 6/2010 | Banchereau et al. |
| 2015/0250868 A1* | 9/2015 | Cobbold .............. A61P 31/04 424/134.1 |

FOREIGN PATENT DOCUMENTS

| | | | |
|---|---|---|---|
| JP | 2007-117023 A | 5/2007 | |
| JP | 2015/501651 A | 1/2015 | |
| JP | 2016-523888 A | 8/2016 | |
| WO | WO-2011/039508 A2 | 4/2011 | |
| WO | WO-2012/123755 A1 | 9/2012 | |
| WO | WO-2016/172722 A1 | 10/2016 | |
| WO | WO-2016/203577 A1 | 12/2016 | |
| WO | WO-2017203362 A1 * | 11/2017 | ............ A61K 35/17 |

OTHER PUBLICATIONS

Byers, T. (CA Cancer Journal, 1999, 49: 353-361).*
Carr et al., "CD27 mediates interleukin-2-independent clonal expansion of the CD8+ T cell without effector differentiation", PNAS, 103(51): 19454-19459 (2006).
Fu et al., "Critical role of EBNA1-specific CD4+ T cells in the control of mouse Burkitt lymphoma in vivo", The Journal of Clinical Investigation, 114(4): 542-550 (2004).
Tschochner et al., "Identifying patient-specific Epstein-barr nuclear antigen-1 genetic variation and potential autoreactive targets relevant to multiple sclerosis pathogenesis", PLOS One, 11(2): e0147567 (2016).
Office Action in Korean Application No. 10-2018-0093987 dated Jul. 3, 2020.
Office Action in Korean Application No. 10-2020-0170517 dated Nov. 10, 2021.
European Application No. 18844804.7 (Patent No. 3666888) Extended European Search Report dated Jul. 30, 2021.

(Continued)

*Primary Examiner* — Yan Xiao
(74) *Attorney, Agent, or Firm* — MARSHALL, GERSTEIN & BORUN LLP

(57) ABSTRACT

The present invention relates to a cancer-specific tumor antigen neoepitope represented by any one of SEQ ID NOs: 1 to 184, an antigen-presenting cell loaded with the neoepitope, and a method for activating T cells for cancer treatment using the antigen-presenting cell. An antigen-presenting cell, that is, a dendritic cell, loaded with a cancer-specific tumor antigen epitope provided in the present invention enables rapid and effective induction of differentiation and proliferation of cancer antigen-specific T cells, preferably memory T cells, and the memory T cells thus activated can treat a cancerous or neoplastic condition or prevent recurrence, progression, or metastasis of cancer while avoiding the defense mechanism of cancer cells.

6 Claims, 10 Drawing Sheets

Specification includes a Sequence Listing.

(56) References Cited

OTHER PUBLICATIONS

Bollard et al., "Cytotoxic T Lymphocyte Therapy for Epstein-Barr Virus Hodgkin's Disease", The Journal of Experimental Medicine, 200(12): 1623-1633 (2004).
Xiao et al., "Dual non-contiguous peptide occupancy of HLA class I evoke antiviral human CD8 T cell response and form neo-epitopes with self-antigen", Scientific Reports, 7:5072 (2017).
Japanese Application No. 2020-507093 Office Action dated Jun. 24, 2022.
Kiyotaka Kuzushima, Virus, vol. 52, No. 1, pp. 123-127 (2002).
Lundegaard et al., "NetMHC-3.0: accurate web accessible predictions of human, mouse and monkey MHC class I affinities for peptides of length 8-11", Nucleic Acids Research, vol. 36, pp. W509-W512 (2008).
Kiessling et al., Identification of an HLA-A*0201—restricted T-cell epitope derived from the prostate cancer-associated protein prostein, *Brit. J. Can.*, 90:034-40 (2004).
Straathof et al., Characterization of Latent Membrane Protein 2 Specificity in CTL Lines from Patients with EBV-Positive Nasopharyngeal Carcinoma and Lymphoma 1, *J. Immunol.*, 175P:4137-47 (2011).

* cited by examiner

[FIG. 1]
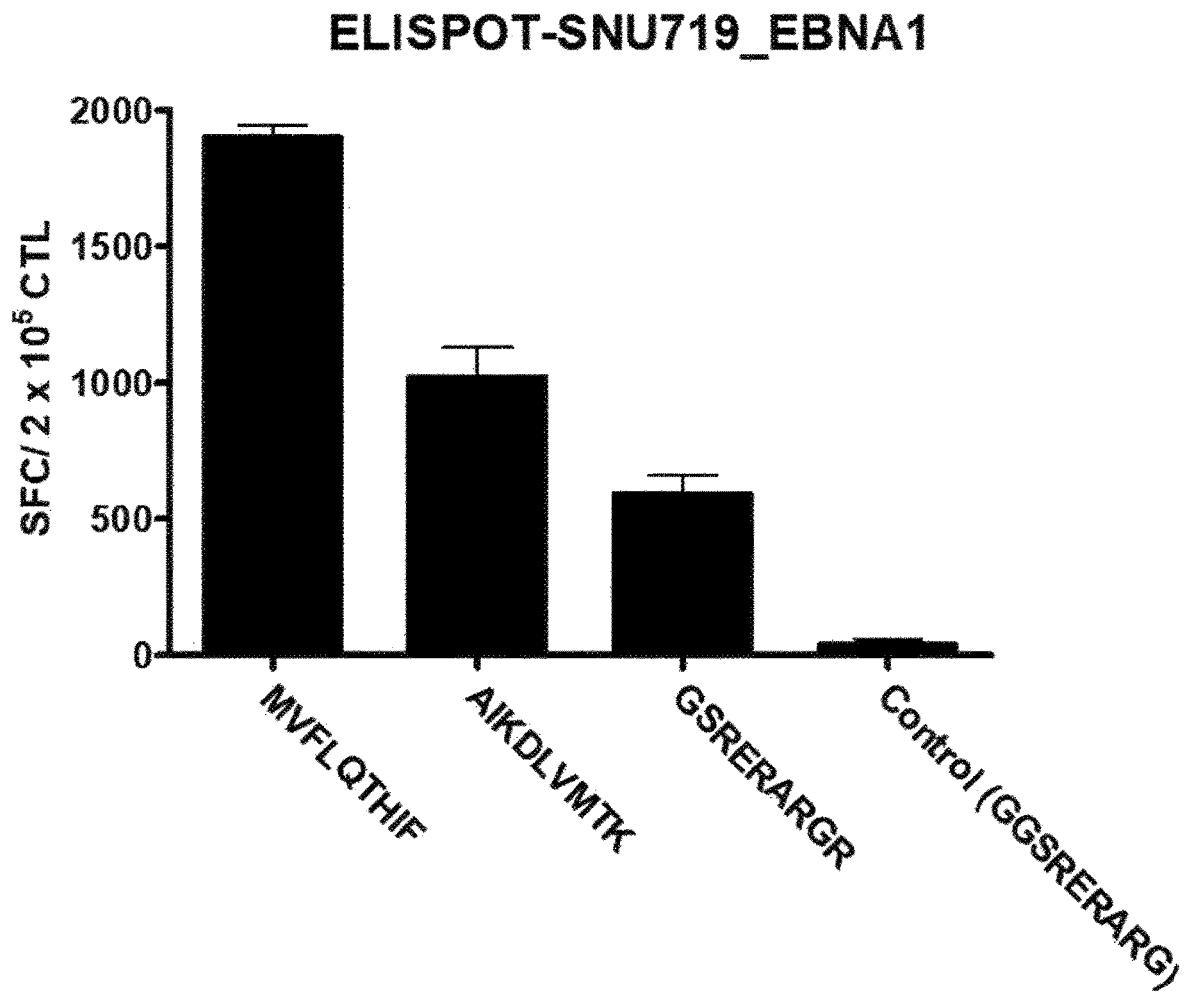

[FIG. 2]
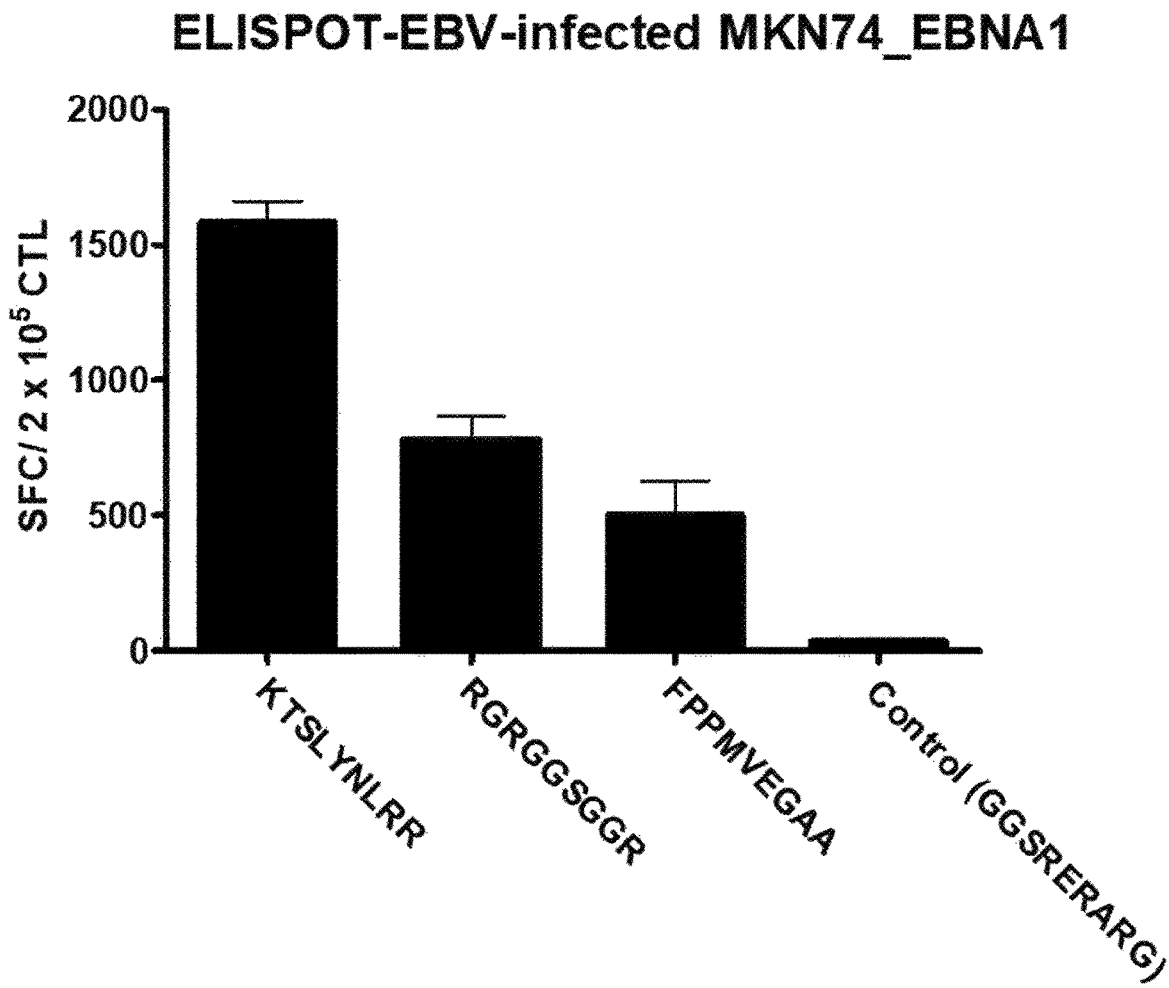

[FIG. 3]
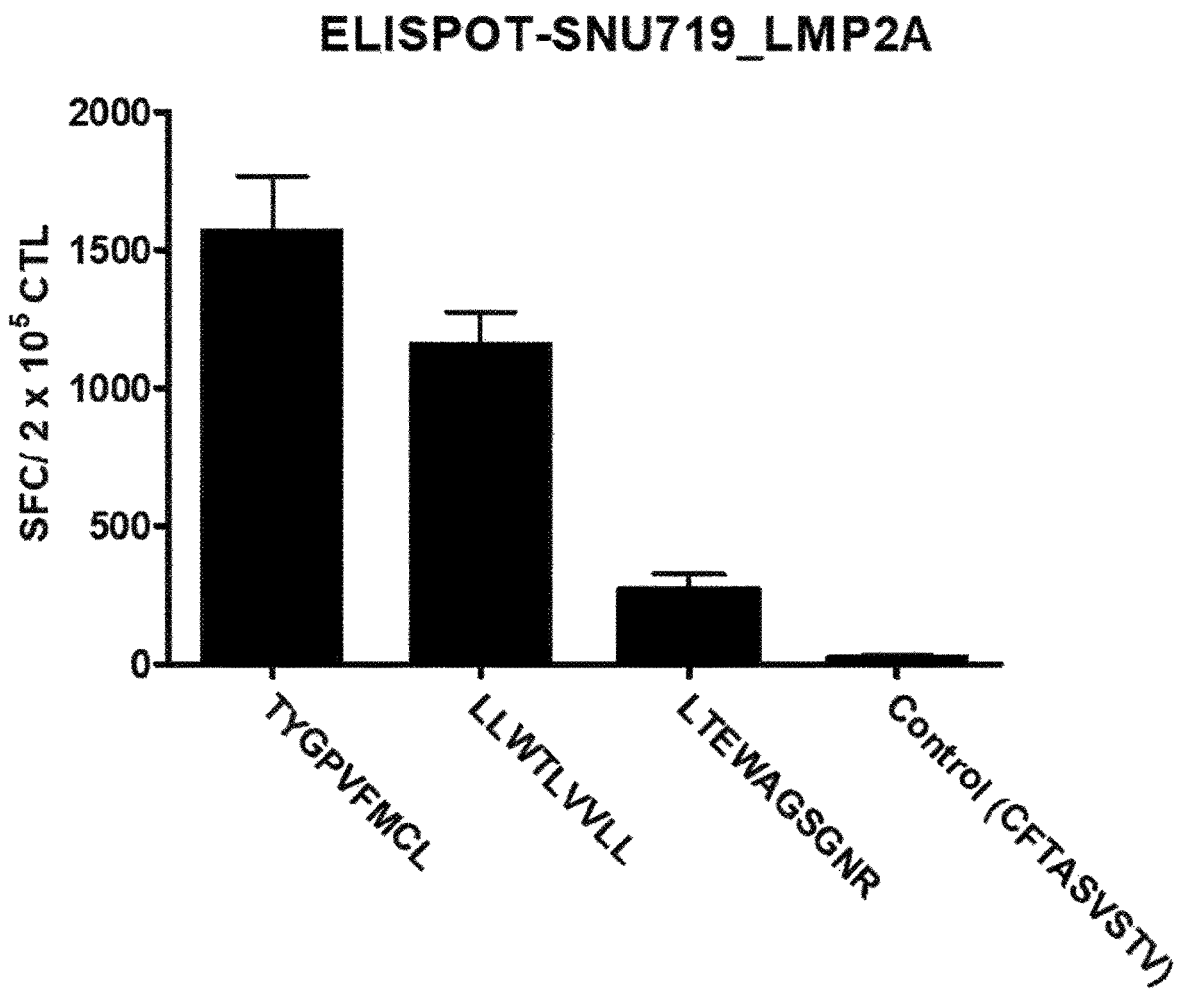

[FIG. 4]
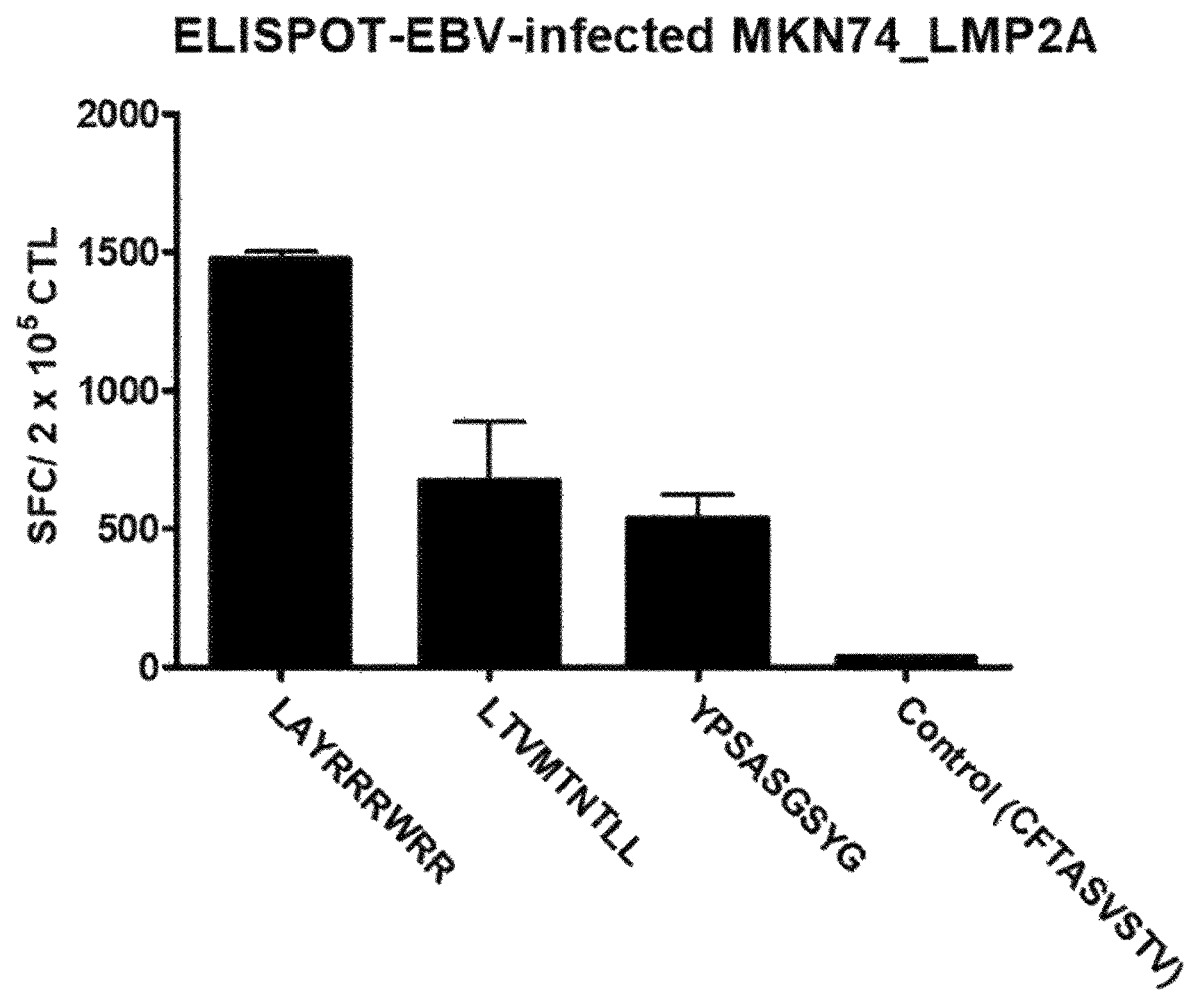

[FIG. 5]
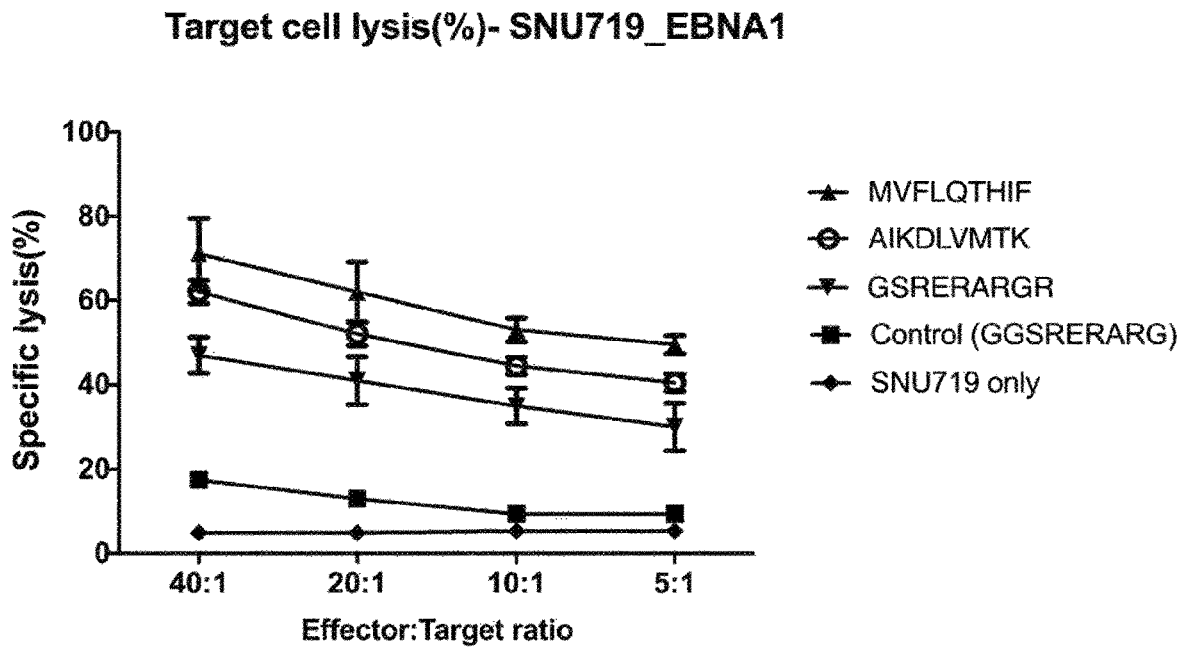
[FIG. 6]
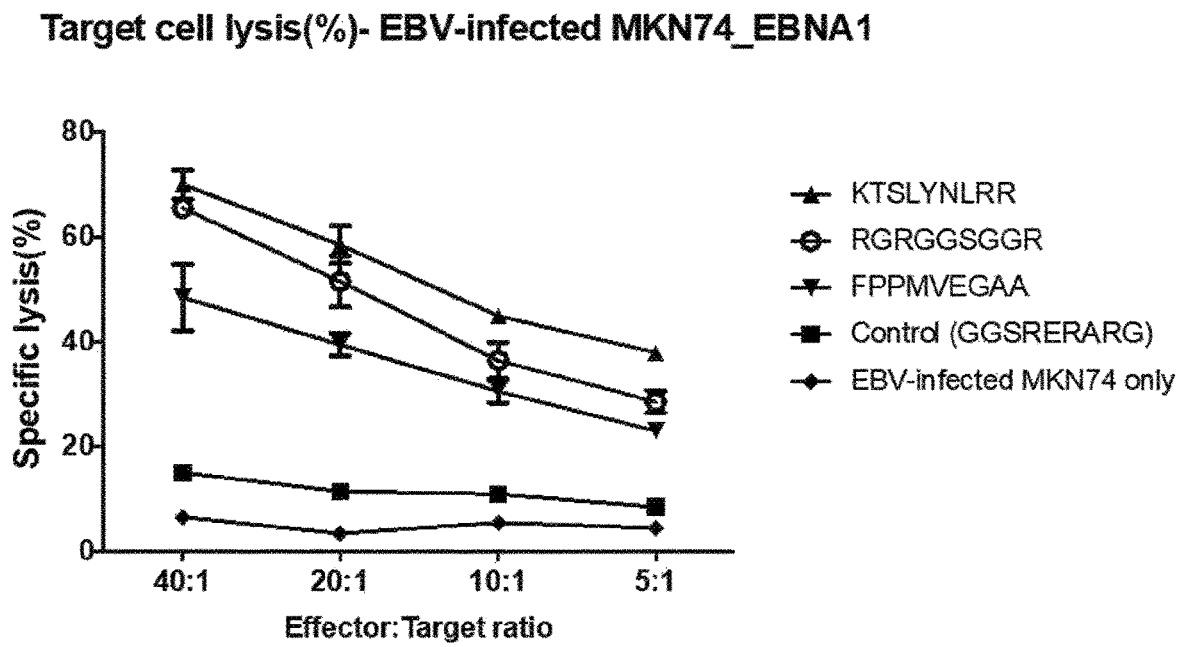

[FIG. 7]
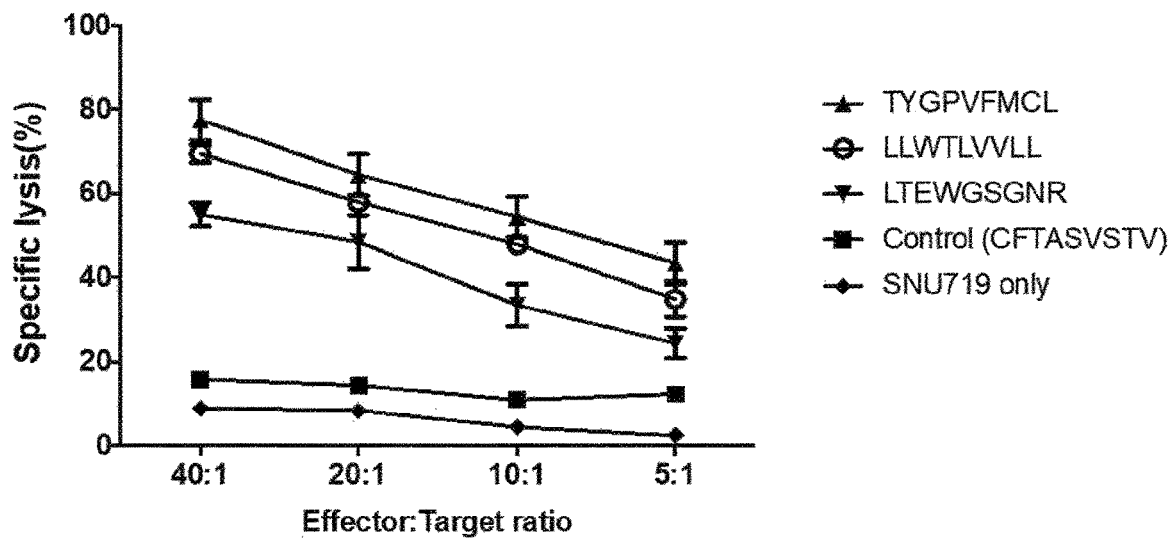
[FIG. 8]
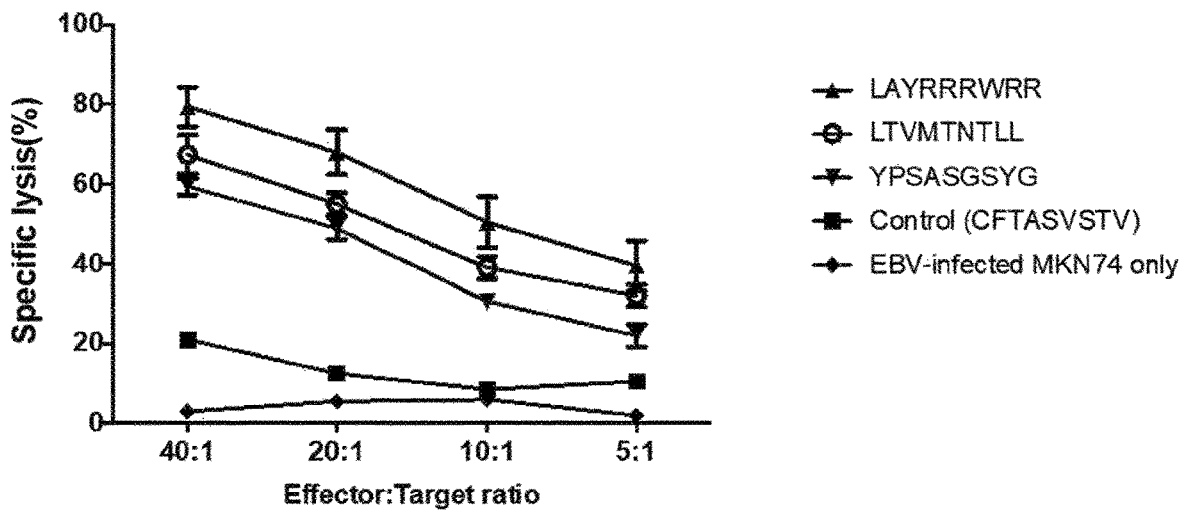

[FIG. 9]
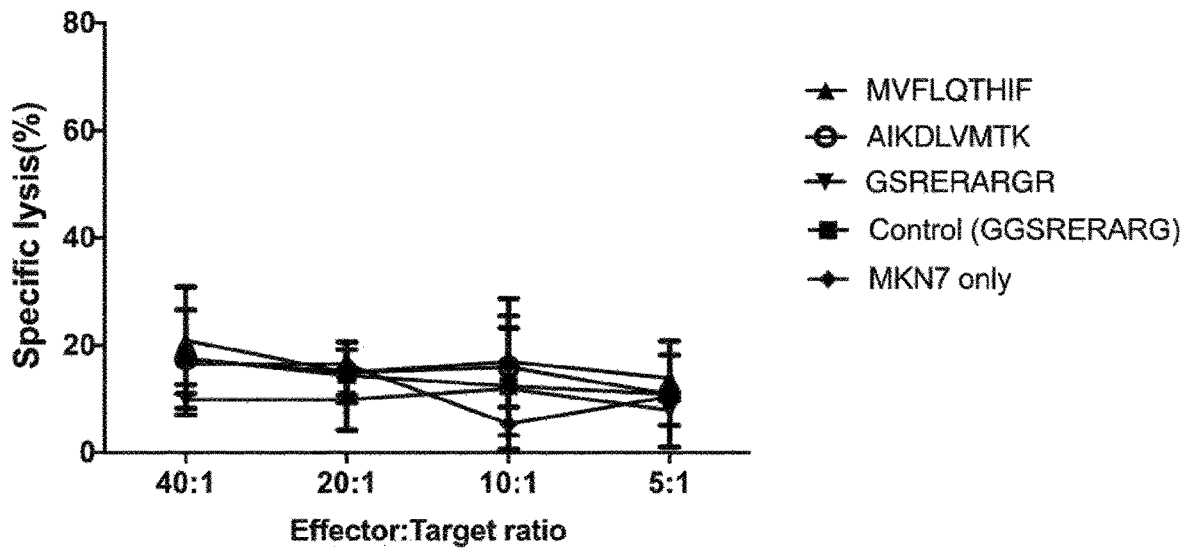
[FIG. 10]
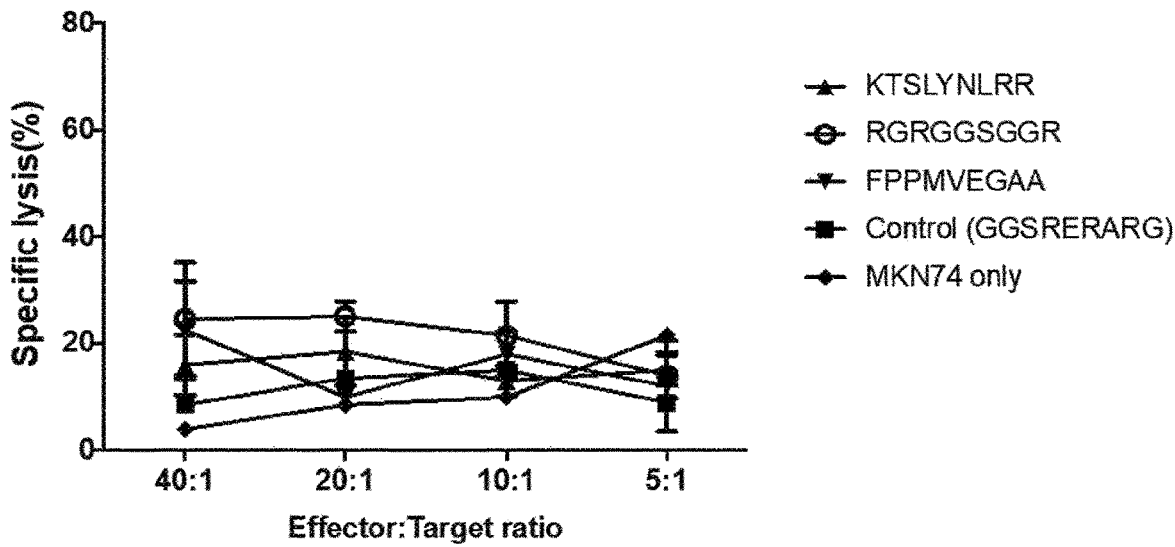

[FIG. 11]
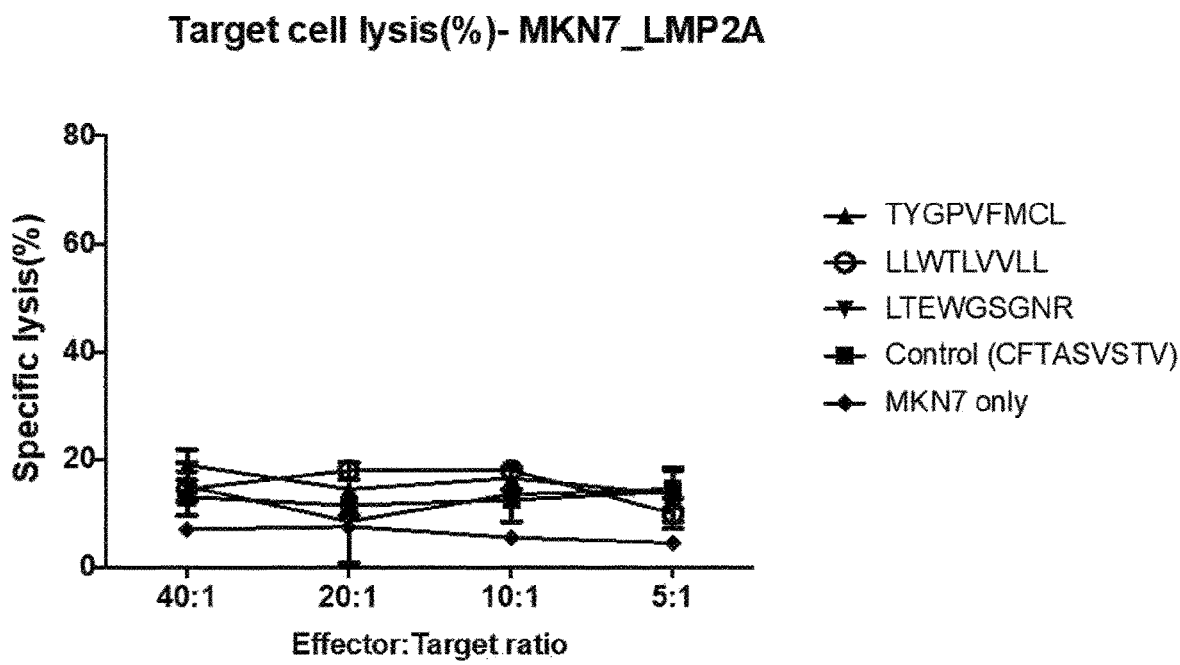
[FIG. 12]
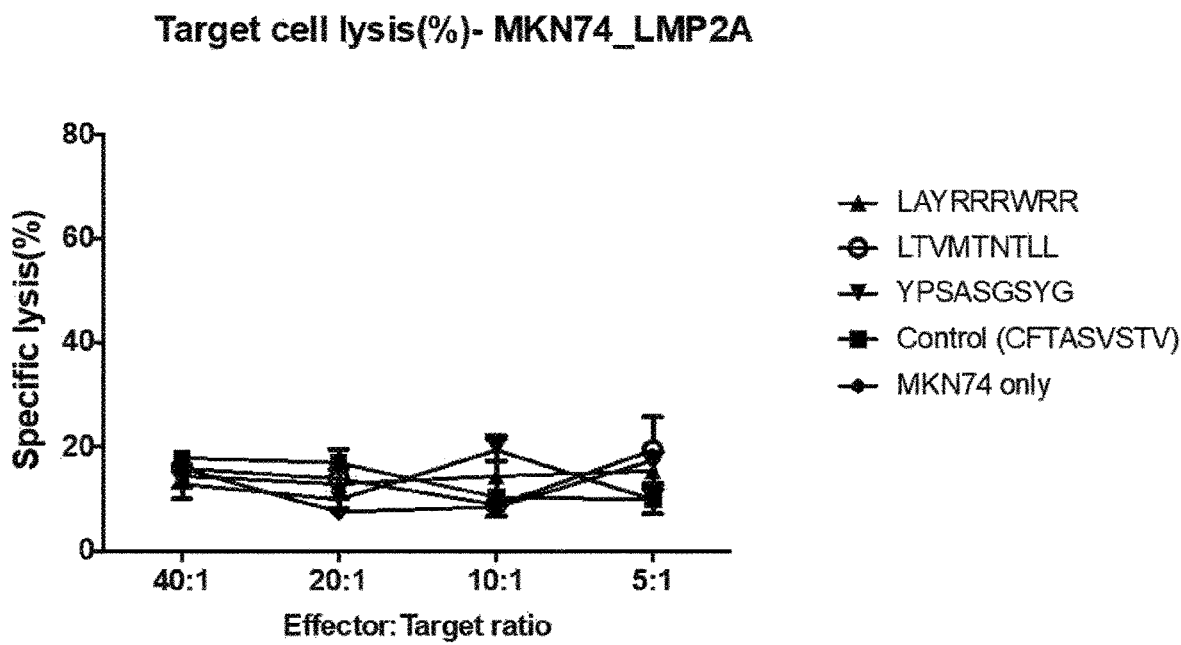

[FIG. 13]
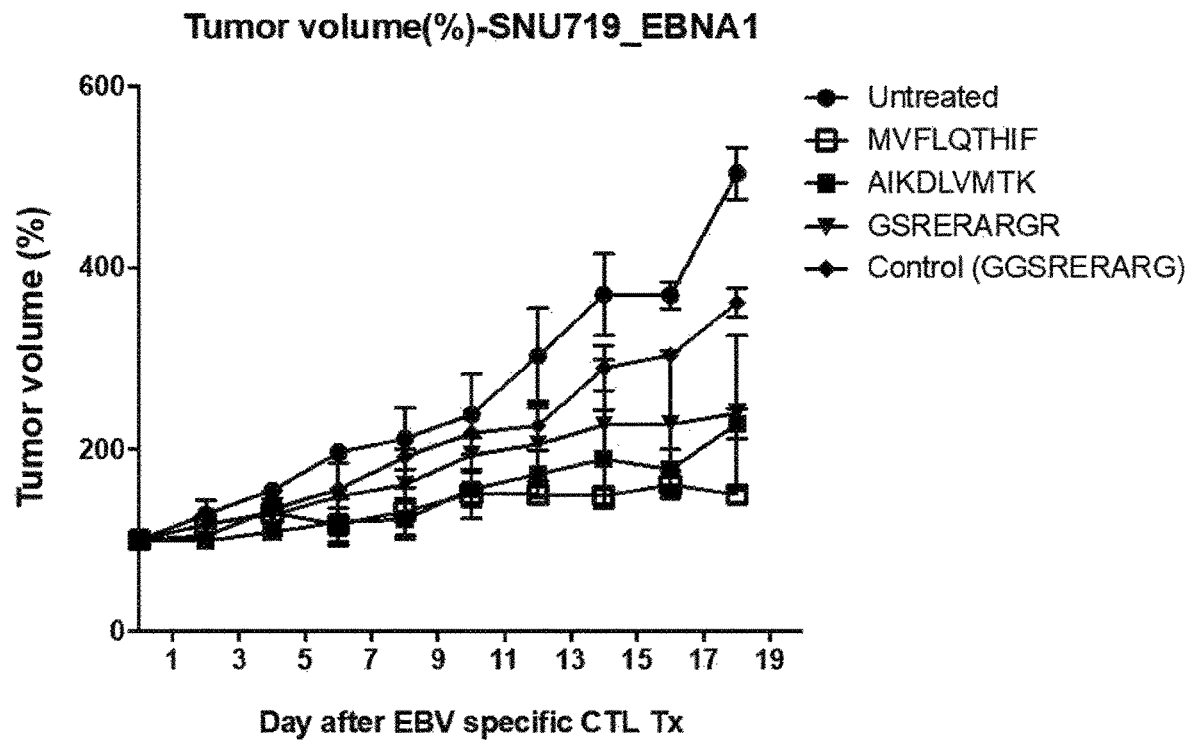
[FIG. 14]
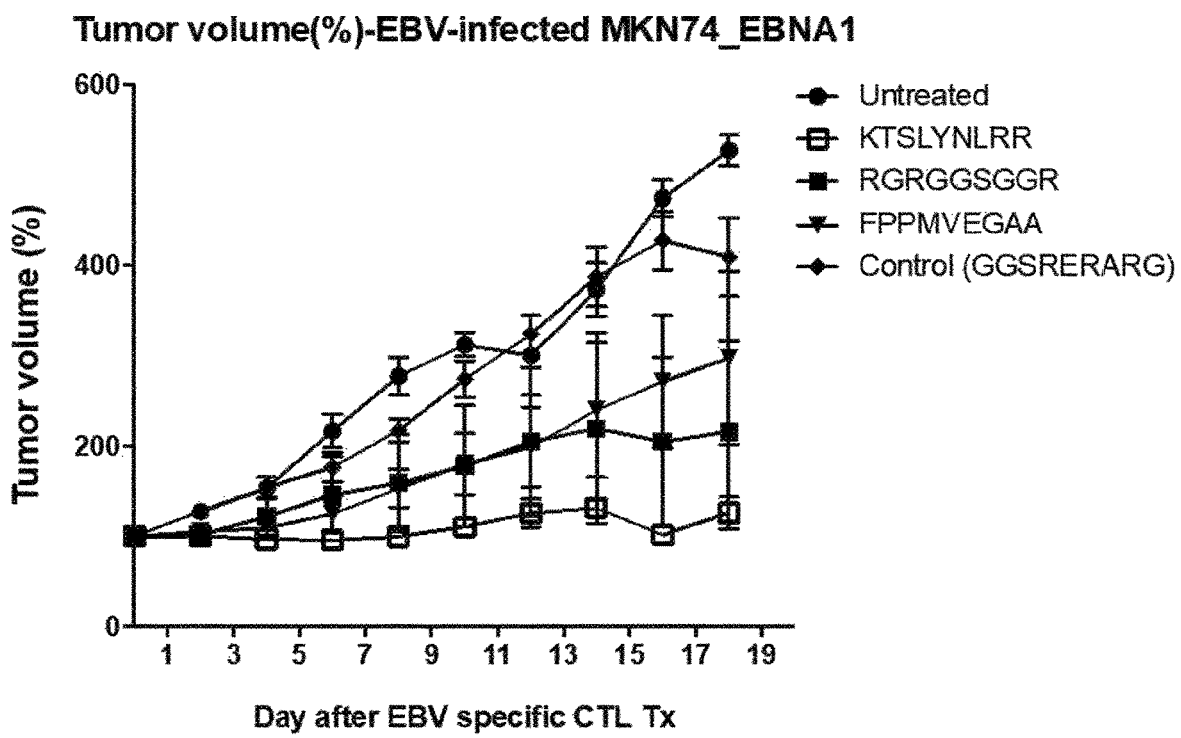

[FIG. 15]
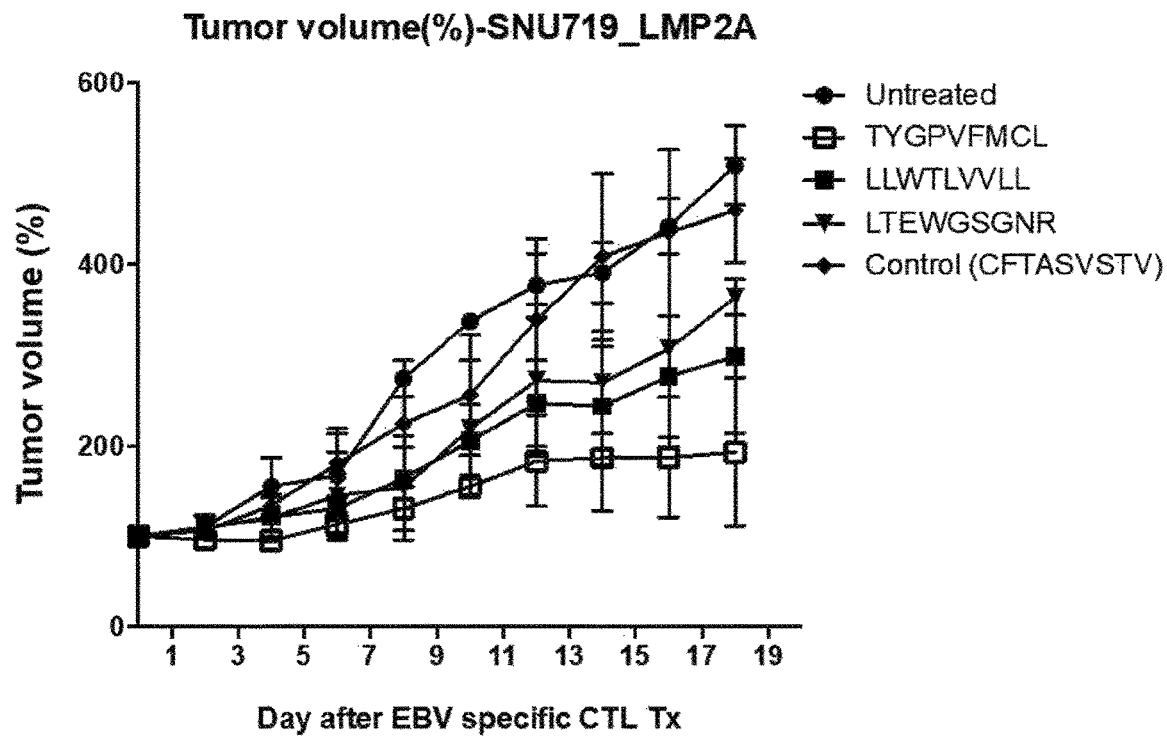
[FIG. 16]
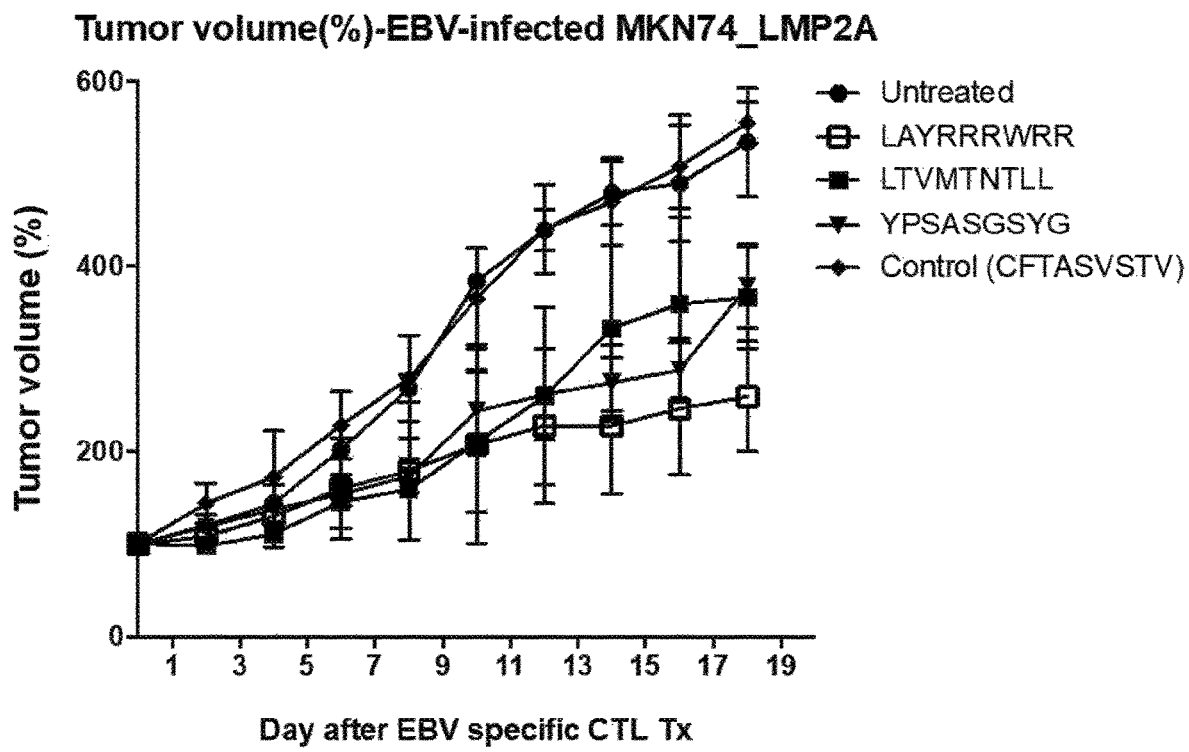

SEQUENCE LISTING

<160> NUMBER OF SEQ ID NOS: 184

<210> SEQ ID NO 1
<211> LENGTH: 9
<212> TYPE: PRT
<213> ORGANISM: Artificial Sequence
<220> FEATURE:
<223> OTHER INFORMATION: Synthetic sequence

<400> SEQUENCE: 1

Met Gly Ser Leu Glu Met Val Pro Met
1               5

<210> SEQ ID NO 2
<211> LENGTH: 9
<212> TYPE: PRT
<213> ORGANISM: Artificial Sequence
<220> FEATURE:
<223> OTHER INFORMATION: Synthetic sequence

<400> SEQUENCE: 2

Ser Met Asn Pro Val Cys Leu Pro Val
1               5

<210> SEQ ID NO 3
<211> LENGTH: 9
<212> TYPE: PRT
<213> ORGANISM: Artificial Sequence
<220> FEATURE:
<223> OTHER INFORMATION: Synthetic sequence

<400> SEQUENCE: 3

Asn Pro Val Cys Leu Pro Val Ile Val
1               5

<210> SEQ ID NO 4
<211> LENGTH: 9
<212> TYPE: PRT
<213> ORGANISM: Artificial Sequence
<220> FEATURE:
<223> OTHER INFORMATION: Synthetic sequence

<400> SEQUENCE: 4

Cys Leu Pro Val Ile Val Ala Pro Tyr
1               5

<210> SEQ ID NO 5
<211> LENGTH: 9
<212> TYPE: PRT
<213> ORGANISM: Artificial Sequence
<220> FEATURE:
<223> OTHER INFORMATION: Synthetic sequence

<400> SEQUENCE: 5

Leu Pro Val Ile Val Ala Pro Tyr Leu
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic sequence

<400> SEQUENCE: 6

```
Val Ile Val Ala Pro Tyr Leu Phe Trp
1               5

<210> SEQ ID NO 7
<211> LENGTH: 9
<212> TYPE: PRT
<213> ORGANISM: Artificial Sequence
<220> FEATURE:
<223> OTHER INFORMATION: Synthetic sequence

<400> SEQUENCE: 7

Ile Val Ala Pro Tyr Leu Phe Trp Leu
1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic sequence

<400> SEQUENCE: 8

Val Ala Pro Tyr Leu Phe Trp Leu Ala
1               5

<210> SEQ ID NO 9
<211> LENGTH: 9
<212> TYPE: PRT
<213> ORGANISM: Artificial Sequence
<220> FEATURE:
<223> OTHER INFORMATION: Synthetic sequence

<400> SEQUENCE: 9

Ala Pro Tyr Leu Phe Trp Leu Ala Ala
1               5

<210> SEQ ID NO 10
<211> LENGTH: 9
<212> TYPE: PRT
<213> ORGANISM: Artificial Sequence
<220> FEATURE:
<223> OTHER INFORMATION: Synthetic sequence

<400> SEQUENCE: 10

Pro Tyr Leu Phe Trp Leu Ala Ala Ile
1               5

<210> SEQ ID NO 11
<211> LENGTH: 9
<212> TYPE: PRT
<213> ORGANISM: Artificial Sequence
<220> FEATURE:
<223> OTHER INFORMATION: Synthetic sequence

<400> SEQUENCE: 11

Tyr Leu Phe Trp Leu Ala Ala Ile Ala
1               5

<210> SEQ ID NO 12
<211> LENGTH: 9
<212> TYPE: PRT
<213> ORGANISM: Artificial Sequence
<220> FEATURE:
<223> OTHER INFORMATION: Synthetic sequence

<400> SEQUENCE: 12
```

Leu Ala Ala Ile Ala Ala Ser Cys Phe
1               5

<210> SEQ ID NO 13
<211> LENGTH: 9
<212> TYPE: PRT
<213> ORGANISM: Artificial Sequence
<220> FEATURE:
<223> OTHER INFORMATION: Synthetic sequence

<400> SEQUENCE: 13

Ala Ile Ala Ala Ser Cys Phe Thr Ala
1               5

<210> SEQ ID NO 14
<211> LENGTH: 9
<212> TYPE: PRT
<213> ORGANISM: Artificial Sequence
<220> FEATURE:
<223> OTHER INFORMATION: Synthetic sequence

<400> SEQUENCE: 14

Ala Ala Ser Cys Phe Thr Ala Ser Val
1               5

<210> SEQ ID NO 15
<211> LENGTH: 9
<212> TYPE: PRT
<213> ORGANISM: Artificial Sequence
<220> FEATURE:
<223> OTHER INFORMATION: Synthetic sequence

<400> SEQUENCE: 15

Phe Thr Ala Ser Val Ser Thr Val Val
1               5

<210> SEQ ID NO 16
<211> LENGTH: 9
<212> TYPE: PRT
<213> ORGANISM: Artificial Sequence
<220> FEATURE:
<223> OTHER INFORMATION: Synthetic sequence

<400> SEQUENCE: 16

Ala Ser Val Ser Thr Val Val Thr Ala
1               5

<210> SEQ ID NO 17
<211> LENGTH: 9
<212> TYPE: PRT
<213> ORGANISM: Artificial Sequence
<220> FEATURE:
<223> OTHER INFORMATION: Synthetic sequence

<400> SEQUENCE: 17

Thr Ala Thr Gly Leu Ala Leu Ser Leu
1               5

<210> SEQ ID NO 18
<211> LENGTH: 9
<212> TYPE: PRT
<213> ORGANISM: Artificial Sequence
<220> FEATURE:
<223> OTHER INFORMATION: Synthetic sequence

<400> SEQUENCE: 18

Gly Leu Ala Leu Ser Leu Leu Leu Leu

```
1               5

<210> SEQ ID NO 19
<211> LENGTH: 9
<212> TYPE: PRT
<213> ORGANISM: Artificial Sequence
<220> FEATURE:
<223> OTHER INFORMATION: Synthetic sequence

<400> SEQUENCE: 19

Leu Ala Leu Ser Leu Leu Leu Leu Ala
1               5

<210> SEQ ID NO 20
<211> LENGTH: 9
<212> TYPE: PRT
<213> ORGANISM: Artificial Sequence
<220> FEATURE:
<223> OTHER INFORMATION: Synthetic sequence

<400> SEQUENCE: 20

Ala Leu Ser Leu Leu Leu Leu Ala Ala
1               5

<210> SEQ ID NO 21
<211> LENGTH: 9
<212> TYPE: PRT
<213> ORGANISM: Artificial Sequence
<220> FEATURE:
<223> OTHER INFORMATION: Synthetic sequence

<400> SEQUENCE: 21

Leu Ser Leu Leu Leu Leu Ala Ala Val
1               5

<210> SEQ ID NO 22
<211> LENGTH: 9
<212> TYPE: PRT
<213> ORGANISM: Artificial Sequence
<220> FEATURE:
<223> OTHER INFORMATION: Synthetic sequence

<400> SEQUENCE: 22

Ser Leu Leu Leu Leu Ala Ala Val Ala
1               5

<210> SEQ ID NO 23
<211> LENGTH: 9
<212> TYPE: PRT
<213> ORGANISM: Artificial Sequence
<220> FEATURE:
<223> OTHER INFORMATION: Synthetic sequence

<400> SEQUENCE: 23

Leu Leu Leu Ala Ala Val Ala Ser Ser
1               5

<210> SEQ ID NO 24
<211> LENGTH: 9
<212> TYPE: PRT
<213> ORGANISM: Artificial Sequence
<220> FEATURE:
<223> OTHER INFORMATION: Synthetic sequence

<400> SEQUENCE: 24

Leu Leu Ala Ala Val Ala Ser Ser Tyr
1               5
```

```
<210> SEQ ID NO 25
<211> LENGTH: 9
<212> TYPE: PRT
<213> ORGANISM: Artificial Sequence
<220> FEATURE:
<223> OTHER INFORMATION: Synthetic sequence

<400> SEQUENCE: 25

Ala Ala Val Ala Ser Ser Tyr Ala Ala
1               5

<210> SEQ ID NO 26
<211> LENGTH: 9
<212> TYPE: PRT
<213> ORGANISM: Artificial Sequence
<220> FEATURE:
<223> OTHER INFORMATION: Synthetic sequence

<400> SEQUENCE: 26

Ala Val Ala Ser Ser Tyr Ala Ala Ala
1               5

<210> SEQ ID NO 27
<211> LENGTH: 9
<212> TYPE: PRT
<213> ORGANISM: Artificial Sequence
<220> FEATURE:
<223> OTHER INFORMATION: Synthetic sequence

<400> SEQUENCE: 27

Ala Ser Ser Tyr Ala Ala Ala Gln Arg
1               5

<210> SEQ ID NO 28
<211> LENGTH: 9
<212> TYPE: PRT
<213> ORGANISM: Artificial Sequence
<220> FEATURE:
<223> OTHER INFORMATION: Synthetic sequence

<400> SEQUENCE: 28

Ser Ser Tyr Ala Ala Ala Gln Arg Lys
1               5

<210> SEQ ID NO 29
<211> LENGTH: 9
<212> TYPE: PRT
<213> ORGANISM: Artificial Sequence
<220> FEATURE:
<223> OTHER INFORMATION: Synthetic sequence

<400> SEQUENCE: 29

Ala Gln Arg Lys Leu Leu Thr Pro Val
1               5

<210> SEQ ID NO 30
<211> LENGTH: 9
<212> TYPE: PRT
<213> ORGANISM: Artificial Sequence
<220> FEATURE:
<223> OTHER INFORMATION: Synthetic sequence

<400> SEQUENCE: 30

Lys Leu Leu Thr Pro Val Thr Val Leu
1               5
```

```
<210> SEQ ID NO 31
<211> LENGTH: 9
<212> TYPE: PRT
<213> ORGANISM: Artificial Sequence
<220> FEATURE:
<223> OTHER INFORMATION: Synthetic sequence

<400> SEQUENCE: 31

Leu Leu Thr Pro Val Thr Val Leu Thr
1               5

<210> SEQ ID NO 32
<211> LENGTH: 9
<212> TYPE: PRT
<213> ORGANISM: Artificial Sequence
<220> FEATURE:
<223> OTHER INFORMATION: Synthetic sequence

<400> SEQUENCE: 32

Thr Pro Val Thr Val Leu Thr Ala Val
1               5

<210> SEQ ID NO 33
<211> LENGTH: 9
<212> TYPE: PRT
<213> ORGANISM: Artificial Sequence
<220> FEATURE:
<223> OTHER INFORMATION: Synthetic sequence

<400> SEQUENCE: 33

Thr Val Leu Thr Ala Val Val Thr Phe
1               5

<210> SEQ ID NO 34
<211> LENGTH: 9
<212> TYPE: PRT
<213> ORGANISM: Artificial Sequence
<220> FEATURE:
<223> OTHER INFORMATION: Synthetic sequence

<400> SEQUENCE: 34

Val Leu Thr Ala Val Val Thr Phe Phe
1               5

<210> SEQ ID NO 35
<211> LENGTH: 9
<212> TYPE: PRT
<213> ORGANISM: Artificial Sequence
<220> FEATURE:
<223> OTHER INFORMATION: Synthetic sequence

<400> SEQUENCE: 35

Leu Thr Ala Val Val Thr Phe Phe Ala
1               5

<210> SEQ ID NO 36
<211> LENGTH: 9
<212> TYPE: PRT
<213> ORGANISM: Artificial Sequence
<220> FEATURE:
<223> OTHER INFORMATION: Synthetic sequence

<400> SEQUENCE: 36

Thr Ala Val Val Thr Phe Phe Ala Ile
1               5
```

<210> SEQ ID NO 37
<211> LENGTH: 9
<212> TYPE: PRT
<213> ORGANISM: Artificial Sequence
<220> FEATURE:
<223> OTHER INFORMATION: Synthetic sequence

<400> SEQUENCE: 37

Thr Phe Phe Ala Ile Cys Leu Thr Trp
1               5

<210> SEQ ID NO 38
<211> LENGTH: 9
<212> TYPE: PRT
<213> ORGANISM: Artificial Sequence
<220> FEATURE:
<223> OTHER INFORMATION: Synthetic sequence

<400> SEQUENCE: 38

Phe Phe Ala Ile Cys Leu Thr Trp Arg
1               5

<210> SEQ ID NO 39
<211> LENGTH: 9
<212> TYPE: PRT
<213> ORGANISM: Artificial Sequence
<220> FEATURE:
<223> OTHER INFORMATION: Synthetic sequence

<400> SEQUENCE: 39

Phe Ala Ile Cys Leu Thr Trp Arg Ile
1               5

<210> SEQ ID NO 40
<211> LENGTH: 9
<212> TYPE: PRT
<213> ORGANISM: Artificial Sequence
<220> FEATURE:
<223> OTHER INFORMATION: Synthetic sequence

<400> SEQUENCE: 40

Ser Leu Leu Phe Ala Leu Leu Ala Ala
1               5

<210> SEQ ID NO 41
<211> LENGTH: 9
<212> TYPE: PRT
<213> ORGANISM: Artificial Sequence
<220> FEATURE:
<223> OTHER INFORMATION: Synthetic sequence

<400> SEQUENCE: 41

Leu Leu Phe Ala Leu Leu Ala Ala Ala
1               5

<210> SEQ ID NO 42
<211> LENGTH: 9
<212> TYPE: PRT
<213> ORGANISM: Artificial Sequence
<220> FEATURE:
<223> OTHER INFORMATION: Synthetic sequence

<400> SEQUENCE: 42

Ala Leu Leu Ala Ala Ala Gly Gly Leu
1               5

<210> SEQ ID NO 43

```
<211> LENGTH: 9
<212> TYPE: PRT
<213> ORGANISM: Artificial Sequence
<220> FEATURE:
<223> OTHER INFORMATION: Synthetic sequence

<400> SEQUENCE: 43

Ala Ala Ala Gly Gly Leu Gln Gly Ile
1               5

<210> SEQ ID NO 44
<211> LENGTH: 9
<212> TYPE: PRT
<213> ORGANISM: Artificial Sequence
<220> FEATURE:
<223> OTHER INFORMATION: Synthetic sequence

<400> SEQUENCE: 44

Gly Leu Gln Gly Ile Tyr Val Leu Val
1               5

<210> SEQ ID NO 45
<211> LENGTH: 9
<212> TYPE: PRT
<213> ORGANISM: Artificial Sequence
<220> FEATURE:
<223> OTHER INFORMATION: Synthetic sequence

<400> SEQUENCE: 45

Leu Gln Gly Ile Tyr Val Leu Val Met
1               5

<210> SEQ ID NO 46
<211> LENGTH: 9
<212> TYPE: PRT
<213> ORGANISM: Artificial Sequence
<220> FEATURE:
<223> OTHER INFORMATION: Synthetic sequence

<400> SEQUENCE: 46

Gly Ile Tyr Val Leu Val Met Leu Val
1               5

<210> SEQ ID NO 47
<211> LENGTH: 9
<212> TYPE: PRT
<213> ORGANISM: Artificial Sequence
<220> FEATURE:
<223> OTHER INFORMATION: Synthetic sequence

<400> SEQUENCE: 47

Tyr Val Leu Val Met Leu Val Leu Leu
1               5

<210> SEQ ID NO 48
<211> LENGTH: 9
<212> TYPE: PRT
<213> ORGANISM: Artificial Sequence
<220> FEATURE:
<223> OTHER INFORMATION: Synthetic sequence

<400> SEQUENCE: 48

Val Met Leu Val Leu Leu Ile Leu Ala
1               5

<210> SEQ ID NO 49
<211> LENGTH: 9
```

```
<212> TYPE: PRT
<213> ORGANISM: Artificial Sequence
<220> FEATURE:
<223> OTHER INFORMATION: Synthetic sequence

<400> SEQUENCE: 49

Met Leu Val Leu Leu Ile Leu Ala Tyr
1               5

<210> SEQ ID NO 50
<211> LENGTH: 9
<212> TYPE: PRT
<213> ORGANISM: Artificial Sequence
<220> FEATURE:
<223> OTHER INFORMATION: Synthetic sequence

<400> SEQUENCE: 50

Leu Val Leu Leu Ile Leu Ala Tyr Arg
1               5

<210> SEQ ID NO 51
<211> LENGTH: 9
<212> TYPE: PRT
<213> ORGANISM: Artificial Sequence
<220> FEATURE:
<223> OTHER INFORMATION: Synthetic sequence

<400> SEQUENCE: 51

Val Leu Leu Ile Leu Ala Tyr Arg Arg
1               5

<210> SEQ ID NO 52
<211> LENGTH: 9
<212> TYPE: PRT
<213> ORGANISM: Artificial Sequence
<220> FEATURE:
<223> OTHER INFORMATION: Synthetic sequence

<400> SEQUENCE: 52

Leu Leu Ile Leu Ala Tyr Arg Arg Arg
1               5

<210> SEQ ID NO 53
<211> LENGTH: 9
<212> TYPE: PRT
<213> ORGANISM: Artificial Sequence
<220> FEATURE:
<223> OTHER INFORMATION: Synthetic sequence

<400> SEQUENCE: 53

Leu Ile Leu Ala Tyr Arg Arg Arg Trp
1               5

<210> SEQ ID NO 54
<211> LENGTH: 9
<212> TYPE: PRT
<213> ORGANISM: Artificial Sequence
<220> FEATURE:
<223> OTHER INFORMATION: Synthetic sequence

<400> SEQUENCE: 54

Ile Leu Ala Tyr Arg Arg Arg Trp Arg
1               5

<210> SEQ ID NO 55
<211> LENGTH: 9
<212> TYPE: PRT
```

```
<213> ORGANISM: Artificial Sequence
<220> FEATURE:
<223> OTHER INFORMATION: Synthetic sequence

<400> SEQUENCE: 55

Leu Ala Tyr Arg Arg Arg Trp Arg Arg
1               5

<210> SEQ ID NO 56
<211> LENGTH: 9
<212> TYPE: PRT
<213> ORGANISM: Artificial Sequence
<220> FEATURE:
<223> OTHER INFORMATION: Synthetic sequence

<400> SEQUENCE: 56

Arg Leu Thr Val Cys Gly Gly Ile Met
1               5

<210> SEQ ID NO 57
<211> LENGTH: 9
<212> TYPE: PRT
<213> ORGANISM: Artificial Sequence
<220> FEATURE:
<223> OTHER INFORMATION: Synthetic sequence

<400> SEQUENCE: 57

Leu Thr Val Cys Gly Gly Ile Met Phe
1               5

<210> SEQ ID NO 58
<211> LENGTH: 9
<212> TYPE: PRT
<213> ORGANISM: Artificial Sequence
<220> FEATURE:
<223> OTHER INFORMATION: Synthetic sequence

<400> SEQUENCE: 58

Thr Val Cys Gly Gly Ile Met Phe Leu
1               5

<210> SEQ ID NO 59
<211> LENGTH: 9
<212> TYPE: PRT
<213> ORGANISM: Artificial Sequence
<220> FEATURE:
<223> OTHER INFORMATION: Synthetic sequence

<400> SEQUENCE: 59

Gly Gly Ile Met Phe Leu Ala Cys Val
1               5

<210> SEQ ID NO 60
<211> LENGTH: 9
<212> TYPE: PRT
<213> ORGANISM: Artificial Sequence
<220> FEATURE:
<223> OTHER INFORMATION: Synthetic sequence

<400> SEQUENCE: 60

Ile Met Phe Leu Ala Cys Val Leu Val
1               5

<210> SEQ ID NO 61
<211> LENGTH: 9
<212> TYPE: PRT
<213> ORGANISM: Artificial Sequence
```

```
<220> FEATURE:
<223> OTHER INFORMATION: Synthetic sequence

<400> SEQUENCE: 61

Phe Leu Ala Cys Val Leu Val Leu Ile
1               5

<210> SEQ ID NO 62
<211> LENGTH: 9
<212> TYPE: PRT
<213> ORGANISM: Artificial Sequence
<220> FEATURE:
<223> OTHER INFORMATION: Synthetic sequence

<400> SEQUENCE: 62

Val Leu Val Leu Ile Val Asp Ala Val
1               5

<210> SEQ ID NO 63
<211> LENGTH: 9
<212> TYPE: PRT
<213> ORGANISM: Artificial Sequence
<220> FEATURE:
<223> OTHER INFORMATION: Synthetic sequence

<400> SEQUENCE: 63

Leu Ile Val Asp Ala Val Leu Gln Leu
1               5

<210> SEQ ID NO 64
<211> LENGTH: 9
<212> TYPE: PRT
<213> ORGANISM: Artificial Sequence
<220> FEATURE:
<223> OTHER INFORMATION: Synthetic sequence

<400> SEQUENCE: 64

Ala Val Leu Gln Leu Ser Pro Leu Leu
1               5

<210> SEQ ID NO 65
<211> LENGTH: 9
<212> TYPE: PRT
<213> ORGANISM: Artificial Sequence
<220> FEATURE:
<223> OTHER INFORMATION: Synthetic sequence

<400> SEQUENCE: 65

Leu Gln Leu Ser Pro Leu Leu Gly Ala
1               5

<210> SEQ ID NO 66
<211> LENGTH: 9
<212> TYPE: PRT
<213> ORGANISM: Artificial Sequence
<220> FEATURE:
<223> OTHER INFORMATION: Synthetic sequence

<400> SEQUENCE: 66

Gln Leu Ser Pro Leu Leu Gly Ala Val
1               5

<210> SEQ ID NO 67
<211> LENGTH: 9
<212> TYPE: PRT
<213> ORGANISM: Artificial Sequence
<220> FEATURE:
```

```
<223> OTHER INFORMATION: Synthetic sequence

<400> SEQUENCE: 67

Ser Pro Leu Leu Gly Ala Val Thr Val
1               5

<210> SEQ ID NO 68
<211> LENGTH: 9
<212> TYPE: PRT
<213> ORGANISM: Artificial Sequence
<220> FEATURE:
<223> OTHER INFORMATION: Synthetic sequence

<400> SEQUENCE: 68

Val Thr Val Val Ser Met Thr Leu Leu
1               5

<210> SEQ ID NO 69
<211> LENGTH: 9
<212> TYPE: PRT
<213> ORGANISM: Artificial Sequence
<220> FEATURE:
<223> OTHER INFORMATION: Synthetic sequence

<400> SEQUENCE: 69

Thr Val Val Ser Met Thr Leu Leu Leu
1               5

<210> SEQ ID NO 70
<211> LENGTH: 9
<212> TYPE: PRT
<213> ORGANISM: Artificial Sequence
<220> FEATURE:
<223> OTHER INFORMATION: Synthetic sequence

<400> SEQUENCE: 70

Val Val Ser Met Thr Leu Leu Leu Leu
1               5

<210> SEQ ID NO 71
<211> LENGTH: 9
<212> TYPE: PRT
<213> ORGANISM: Artificial Sequence
<220> FEATURE:
<223> OTHER INFORMATION: Synthetic sequence

<400> SEQUENCE: 71

Val Ser Met Thr Leu Leu Leu Leu Ala
1               5

<210> SEQ ID NO 72
<211> LENGTH: 9
<212> TYPE: PRT
<213> ORGANISM: Artificial Sequence
<220> FEATURE:
<223> OTHER INFORMATION: Synthetic sequence

<400> SEQUENCE: 72

Ser Met Thr Leu Leu Leu Leu Ala Phe
1               5

<210> SEQ ID NO 73
<211> LENGTH: 9
<212> TYPE: PRT
<213> ORGANISM: Artificial Sequence
<220> FEATURE:
<223> OTHER INFORMATION: Synthetic sequence
```

<400> SEQUENCE: 73

Met Thr Leu Leu Leu Ala Phe Val
1               5

<210> SEQ ID NO 74
<211> LENGTH: 9
<212> TYPE: PRT
<213> ORGANISM: Artificial Sequence
<220> FEATURE:
<223> OTHER INFORMATION: Synthetic sequence

<400> SEQUENCE: 74

Thr Leu Leu Leu Leu Ala Phe Val Leu
1               5

<210> SEQ ID NO 75
<211> LENGTH: 9
<212> TYPE: PRT
<213> ORGANISM: Artificial Sequence
<220> FEATURE:
<223> OTHER INFORMATION: Synthetic sequence

<400> SEQUENCE: 75

Leu Leu Leu Ala Phe Val Leu Trp Leu
1               5

<210> SEQ ID NO 76
<211> LENGTH: 9
<212> TYPE: PRT
<213> ORGANISM: Artificial Sequence
<220> FEATURE:
<223> OTHER INFORMATION: Synthetic sequence

<400> SEQUENCE: 76

Leu Leu Ala Phe Val Leu Trp Leu Ser
1               5

<210> SEQ ID NO 77
<211> LENGTH: 9
<212> TYPE: PRT
<213> ORGANISM: Artificial Sequence
<220> FEATURE:
<223> OTHER INFORMATION: Synthetic sequence

<400> SEQUENCE: 77

Thr Leu Gly Ala Ala Leu Leu Thr Leu
1               5

<210> SEQ ID NO 78
<211> LENGTH: 9
<212> TYPE: PRT
<213> ORGANISM: Artificial Sequence
<220> FEATURE:
<223> OTHER INFORMATION: Synthetic sequence

<400> SEQUENCE: 78

Ala Ala Leu Leu Thr Leu Ala Ala Ala
1               5

<210> SEQ ID NO 79
<211> LENGTH: 9
<212> TYPE: PRT
<213> ORGANISM: Artificial Sequence
<220> FEATURE:
<223> OTHER INFORMATION: Synthetic sequence

```
<400> SEQUENCE: 79

Ala Leu Leu Thr Leu Ala Ala Ala Leu
1               5

<210> SEQ ID NO 80
<211> LENGTH: 9
<212> TYPE: PRT
<213> ORGANISM: Artificial Sequence
<220> FEATURE:
<223> OTHER INFORMATION: Synthetic sequence

<400> SEQUENCE: 80

Leu Thr Leu Ala Ala Ala Leu Ala Leu
1               5

<210> SEQ ID NO 81
<211> LENGTH: 9
<212> TYPE: PRT
<213> ORGANISM: Artificial Sequence
<220> FEATURE:
<223> OTHER INFORMATION: Synthetic sequence

<400> SEQUENCE: 81

Thr Leu Ala Ala Ala Leu Ala Leu Leu
1               5

<210> SEQ ID NO 82
<211> LENGTH: 9
<212> TYPE: PRT
<213> ORGANISM: Artificial Sequence
<220> FEATURE:
<223> OTHER INFORMATION: Synthetic sequence

<400> SEQUENCE: 82

Leu Ala Ala Ala Leu Ala Leu Leu Ala
1               5

<210> SEQ ID NO 83
<211> LENGTH: 9
<212> TYPE: PRT
<213> ORGANISM: Artificial Sequence
<220> FEATURE:
<223> OTHER INFORMATION: Synthetic sequence

<400> SEQUENCE: 83

Ala Ala Leu Ala Leu Leu Ala Ser Leu
1               5

<210> SEQ ID NO 84
<211> LENGTH: 9
<212> TYPE: PRT
<213> ORGANISM: Artificial Sequence
<220> FEATURE:
<223> OTHER INFORMATION: Synthetic sequence

<400> SEQUENCE: 84

Ala Leu Ala Leu Leu Ala Ser Leu Ile
1               5

<210> SEQ ID NO 85
<211> LENGTH: 9
<212> TYPE: PRT
<213> ORGANISM: Artificial Sequence
<220> FEATURE:
<223> OTHER INFORMATION: Synthetic sequence

<400> SEQUENCE: 85
```

```
Leu Ala Leu Leu Ala Ser Leu Ile Leu
1               5

<210> SEQ ID NO 86
<211> LENGTH: 9
<212> TYPE: PRT
<213> ORGANISM: Artificial Sequence
<220> FEATURE:
<223> OTHER INFORMATION: Synthetic sequence

<400> SEQUENCE: 86

Tyr Pro Ser Ala Ser Gly Ser Tyr Gly
1               5

<210> SEQ ID NO 87
<211> LENGTH: 9
<212> TYPE: PRT
<213> ORGANISM: Artificial Sequence
<220> FEATURE:
<223> OTHER INFORMATION: Synthetic sequence

<400> SEQUENCE: 87

Leu Leu Ala Ser Leu Ile Leu Gly Thr
1               5

<210> SEQ ID NO 88
<211> LENGTH: 9
<212> TYPE: PRT
<213> ORGANISM: Artificial Sequence
<220> FEATURE:
<223> OTHER INFORMATION: Synthetic sequence

<400> SEQUENCE: 88

Ser Leu Ile Leu Gly Thr Leu Asn Leu
1               5

<210> SEQ ID NO 89
<211> LENGTH: 9
<212> TYPE: PRT
<213> ORGANISM: Artificial Sequence
<220> FEATURE:
<223> OTHER INFORMATION: Synthetic sequence

<400> SEQUENCE: 89

Leu Ile Leu Gly Thr Leu Asn Leu Thr
1               5

<210> SEQ ID NO 90
<211> LENGTH: 9
<212> TYPE: PRT
<213> ORGANISM: Artificial Sequence
<220> FEATURE:
<223> OTHER INFORMATION: Synthetic sequence

<400> SEQUENCE: 90

Gly Thr Leu Asn Leu Thr Thr Met Phe
1               5

<210> SEQ ID NO 91
<211> LENGTH: 9
<212> TYPE: PRT
<213> ORGANISM: Artificial Sequence
<220> FEATURE:
<223> OTHER INFORMATION: Synthetic sequence

<400> SEQUENCE: 91
```

```
Thr Leu Asn Leu Thr Thr Met Phe Leu
1               5

<210> SEQ ID NO 92
<211> LENGTH: 9
<212> TYPE: PRT
<213> ORGANISM: Artificial Sequence
<220> FEATURE:
<223> OTHER INFORMATION: Synthetic sequence

<400> SEQUENCE: 92

Asn Leu Thr Thr Met Phe Leu Leu Met
1               5

<210> SEQ ID NO 93
<211> LENGTH: 9
<212> TYPE: PRT
<213> ORGANISM: Artificial Sequence
<220> FEATURE:
<223> OTHER INFORMATION: Synthetic sequence

<400> SEQUENCE: 93

Thr Thr Met Phe Leu Leu Met Leu Leu
1               5

<210> SEQ ID NO 94
<211> LENGTH: 9
<212> TYPE: PRT
<213> ORGANISM: Artificial Sequence
<220> FEATURE:
<223> OTHER INFORMATION: Synthetic sequence

<400> SEQUENCE: 94

Thr Met Phe Leu Leu Met Leu Leu Trp
1               5

<210> SEQ ID NO 95
<211> LENGTH: 9
<212> TYPE: PRT
<213> ORGANISM: Artificial Sequence
<220> FEATURE:
<223> OTHER INFORMATION: Synthetic sequence

<400> SEQUENCE: 95

Phe Leu Leu Met Leu Leu Trp Thr Leu
1               5

<210> SEQ ID NO 96
<211> LENGTH: 9
<212> TYPE: PRT
<213> ORGANISM: Artificial Sequence
<220> FEATURE:
<223> OTHER INFORMATION: Synthetic sequence

<400> SEQUENCE: 96

Leu Leu Met Leu Leu Trp Thr Leu Val
1               5

<210> SEQ ID NO 97
<211> LENGTH: 9
<212> TYPE: PRT
<213> ORGANISM: Artificial Sequence
<220> FEATURE:
<223> OTHER INFORMATION: Synthetic sequence

<400> SEQUENCE: 97

Leu Met Leu Leu Trp Thr Leu Val Val
```

```
1               5
```

<210> SEQ ID NO 98
<211> LENGTH: 9
<212> TYPE: PRT
<213> ORGANISM: Artificial Sequence
<220> FEATURE:
<223> OTHER INFORMATION: Synthetic sequence

<400> SEQUENCE: 98

```
Met Leu Leu Trp Thr Leu Val Val Leu
1               5
```

<210> SEQ ID NO 99
<211> LENGTH: 9
<212> TYPE: PRT
<213> ORGANISM: Artificial Sequence
<220> FEATURE:
<223> OTHER INFORMATION: Synthetic sequence

<400> SEQUENCE: 99

```
Leu Leu Trp Thr Leu Val Val Leu Leu
1               5
```

<210> SEQ ID NO 100
<211> LENGTH: 9
<212> TYPE: PRT
<213> ORGANISM: Artificial Sequence
<220> FEATURE:
<223> OTHER INFORMATION: Synthetic sequence

<400> SEQUENCE: 100

```
Cys Pro Leu Thr Lys Ile Leu Leu Ala
1               5
```

<210> SEQ ID NO 101
<211> LENGTH: 9
<212> TYPE: PRT
<213> ORGANISM: Artificial Sequence
<220> FEATURE:
<223> OTHER INFORMATION: Synthetic sequence

<400> SEQUENCE: 101

```
Ile Leu Leu Ala Arg Leu Phe Leu Tyr
1               5
```

<210> SEQ ID NO 102
<211> LENGTH: 9
<212> TYPE: PRT
<213> ORGANISM: Artificial Sequence
<220> FEATURE:
<223> OTHER INFORMATION: Synthetic sequence

<400> SEQUENCE: 102

```
Leu Leu Ala Arg Leu Phe Leu Tyr Ala
1               5
```

<210> SEQ ID NO 103
<211> LENGTH: 9
<212> TYPE: PRT
<213> ORGANISM: Artificial Sequence
<220> FEATURE:
<223> OTHER INFORMATION: Synthetic sequence

<400> SEQUENCE: 103

```
Arg Leu Phe Leu Tyr Ala Leu Ala Leu
1               5
```

<210> SEQ ID NO 104
<211> LENGTH: 9
<212> TYPE: PRT
<213> ORGANISM: Artificial Sequence
<220> FEATURE:
<223> OTHER INFORMATION: Synthetic sequence

<400> SEQUENCE: 104

Phe Leu Tyr Ala Leu Ala Leu Leu Leu
1               5

<210> SEQ ID NO 105
<211> LENGTH: 9
<212> TYPE: PRT
<213> ORGANISM: Artificial Sequence
<220> FEATURE:
<223> OTHER INFORMATION: Synthetic sequence

<400> SEQUENCE: 105

Leu Tyr Ala Leu Ala Leu Leu Leu Leu
1               5

<210> SEQ ID NO 106
<211> LENGTH: 9
<212> TYPE: PRT
<213> ORGANISM: Artificial Sequence
<220> FEATURE:
<223> OTHER INFORMATION: Synthetic sequence

<400> SEQUENCE: 106

Tyr Ala Leu Ala Leu Leu Leu Leu Ala
1               5

<210> SEQ ID NO 107
<211> LENGTH: 9
<212> TYPE: PRT
<213> ORGANISM: Artificial Sequence
<220> FEATURE:
<223> OTHER INFORMATION: Synthetic sequence

<400> SEQUENCE: 107

Leu Ala Leu Leu Leu Leu Ala Ser Ala
1               5

<210> SEQ ID NO 108
<211> LENGTH: 9
<212> TYPE: PRT
<213> ORGANISM: Artificial Sequence
<220> FEATURE:
<223> OTHER INFORMATION: Synthetic sequence

<400> SEQUENCE: 108

Ala Leu Leu Leu Leu Ala Ser Ala Leu
1               5

<210> SEQ ID NO 109
<211> LENGTH: 9
<212> TYPE: PRT
<213> ORGANISM: Artificial Sequence
<220> FEATURE:
<223> OTHER INFORMATION: Synthetic sequence

<400> SEQUENCE: 109

Leu Leu Leu Leu Ala Ser Ala Leu Ile
1               5

<210> SEQ ID NO 110
<211> LENGTH: 9
<212> TYPE: PRT
<213> ORGANISM: Artificial Sequence
<220> FEATURE:
<223> OTHER INFORMATION: Synthetic sequence

<400> SEQUENCE: 110

Leu Leu Leu Ala Ser Ala Leu Ile Ala
1               5

<210> SEQ ID NO 111
<211> LENGTH: 9
<212> TYPE: PRT
<213> ORGANISM: Artificial Sequence
<220> FEATURE:
<223> OTHER INFORMATION: Synthetic sequence

<400> SEQUENCE: 111

Ala Leu Ile Ala Gly Gly Ser Ile Leu
1               5

<210> SEQ ID NO 112
<211> LENGTH: 9
<212> TYPE: PRT
<213> ORGANISM: Artificial Sequence
<220> FEATURE:
<223> OTHER INFORMATION: Synthetic sequence

<400> SEQUENCE: 112

Gly Ser Ile Leu Gln Thr Asn Phe Lys
1               5

<210> SEQ ID NO 113
<211> LENGTH: 9
<212> TYPE: PRT
<213> ORGANISM: Artificial Sequence
<220> FEATURE:
<223> OTHER INFORMATION: Synthetic sequence

<400> SEQUENCE: 113

Lys Ser Leu Ser Ser Thr Glu Phe Ile
1               5

<210> SEQ ID NO 114
<211> LENGTH: 9
<212> TYPE: PRT
<213> ORGANISM: Artificial Sequence
<220> FEATURE:
<223> OTHER INFORMATION: Synthetic sequence

<400> SEQUENCE: 114

Ser Ser Thr Glu Phe Ile Pro Asn Leu
1               5

<210> SEQ ID NO 115
<211> LENGTH: 9
<212> TYPE: PRT
<213> ORGANISM: Artificial Sequence
<220> FEATURE:
<223> OTHER INFORMATION: Synthetic sequence

<400> SEQUENCE: 115

Phe Ile Pro Asn Leu Phe Cys Met Leu
1               5

```
<210> SEQ ID NO 116
<211> LENGTH: 9
<212> TYPE: PRT
<213> ORGANISM: Artificial Sequence
<220> FEATURE:
<223> OTHER INFORMATION: Synthetic sequence

<400> SEQUENCE: 116

Ile Pro Asn Leu Phe Cys Met Leu Leu
1               5

<210> SEQ ID NO 117
<211> LENGTH: 9
<212> TYPE: PRT
<213> ORGANISM: Artificial Sequence
<220> FEATURE:
<223> OTHER INFORMATION: Synthetic sequence

<400> SEQUENCE: 117

Asn Leu Phe Cys Met Leu Leu Leu Ile
1               5

<210> SEQ ID NO 118
<211> LENGTH: 9
<212> TYPE: PRT
<213> ORGANISM: Artificial Sequence
<220> FEATURE:
<223> OTHER INFORMATION: Synthetic sequence

<400> SEQUENCE: 118

Met Leu Leu Leu Ile Val Ala Gly Ile
1               5

<210> SEQ ID NO 119
<211> LENGTH: 9
<212> TYPE: PRT
<213> ORGANISM: Artificial Sequence
<220> FEATURE:
<223> OTHER INFORMATION: Synthetic sequence

<400> SEQUENCE: 119

Leu Leu Ile Val Ala Gly Ile Leu Phe
1               5

<210> SEQ ID NO 120
<211> LENGTH: 9
<212> TYPE: PRT
<213> ORGANISM: Artificial Sequence
<220> FEATURE:
<223> OTHER INFORMATION: Synthetic sequence

<400> SEQUENCE: 120

Leu Ile Val Ala Gly Ile Leu Phe Ile
1               5

<210> SEQ ID NO 121
<211> LENGTH: 9
<212> TYPE: PRT
<213> ORGANISM: Artificial Sequence
<220> FEATURE:
<223> OTHER INFORMATION: Synthetic sequence

<400> SEQUENCE: 121

Ile Val Ala Gly Ile Leu Phe Ile Leu
1               5

<210> SEQ ID NO 122
```

```
<211> LENGTH: 9
<212> TYPE: PRT
<213> ORGANISM: Artificial Sequence
<220> FEATURE:
<223> OTHER INFORMATION: Synthetic sequence

<400> SEQUENCE: 122

Phe Ile Leu Ala Ile Leu Thr Glu Trp
1               5

<210> SEQ ID NO 123
<211> LENGTH: 9
<212> TYPE: PRT
<213> ORGANISM: Artificial Sequence
<220> FEATURE:
<223> OTHER INFORMATION: Synthetic sequence

<400> SEQUENCE: 123

Leu Thr Glu Trp Gly Ser Gly Asn Arg
1               5

<210> SEQ ID NO 124
<211> LENGTH: 9
<212> TYPE: PRT
<213> ORGANISM: Artificial Sequence
<220> FEATURE:
<223> OTHER INFORMATION: Synthetic sequence

<400> SEQUENCE: 124

Arg Thr Tyr Gly Pro Val Phe Met Cys
1               5

<210> SEQ ID NO 125
<211> LENGTH: 9
<212> TYPE: PRT
<213> ORGANISM: Artificial Sequence
<220> FEATURE:
<223> OTHER INFORMATION: Synthetic sequence

<400> SEQUENCE: 125

Thr Tyr Gly Pro Val Phe Met Cys Leu
1               5

<210> SEQ ID NO 126
<211> LENGTH: 9
<212> TYPE: PRT
<213> ORGANISM: Artificial Sequence
<220> FEATURE:
<223> OTHER INFORMATION: Synthetic sequence

<400> SEQUENCE: 126

Phe Met Cys Leu Gly Gly Leu Leu Thr
1               5

<210> SEQ ID NO 127
<211> LENGTH: 9
<212> TYPE: PRT
<213> ORGANISM: Artificial Sequence
<220> FEATURE:
<223> OTHER INFORMATION: Synthetic sequence

<400> SEQUENCE: 127

Met Cys Leu Gly Gly Leu Leu Thr Met
1               5

<210> SEQ ID NO 128
<211> LENGTH: 9
```

```
<212> TYPE: PRT
<213> ORGANISM: Artificial Sequence
<220> FEATURE:
<223> OTHER INFORMATION: Synthetic sequence

<400> SEQUENCE: 128

Cys Leu Gly Gly Leu Leu Thr Met Val
1               5

<210> SEQ ID NO 129
<211> LENGTH: 9
<212> TYPE: PRT
<213> ORGANISM: Artificial Sequence
<220> FEATURE:
<223> OTHER INFORMATION: Synthetic sequence

<400> SEQUENCE: 129

Gly Leu Leu Thr Met Val Ala Gly Ala
1               5

<210> SEQ ID NO 130
<211> LENGTH: 9
<212> TYPE: PRT
<213> ORGANISM: Artificial Sequence
<220> FEATURE:
<223> OTHER INFORMATION: Synthetic sequence

<400> SEQUENCE: 130

Leu Leu Thr Met Val Ala Gly Ala Val
1               5

<210> SEQ ID NO 131
<211> LENGTH: 9
<212> TYPE: PRT
<213> ORGANISM: Artificial Sequence
<220> FEATURE:
<223> OTHER INFORMATION: Synthetic sequence

<400> SEQUENCE: 131

Leu Thr Met Val Ala Gly Ala Val Trp
1               5

<210> SEQ ID NO 132
<211> LENGTH: 9
<212> TYPE: PRT
<213> ORGANISM: Artificial Sequence
<220> FEATURE:
<223> OTHER INFORMATION: Synthetic sequence

<400> SEQUENCE: 132

Thr Met Val Ala Gly Ala Val Trp Leu
1               5

<210> SEQ ID NO 133
<211> LENGTH: 9
<212> TYPE: PRT
<213> ORGANISM: Artificial Sequence
<220> FEATURE:
<223> OTHER INFORMATION: Synthetic sequence

<400> SEQUENCE: 133

Met Val Ala Gly Ala Val Trp Leu Thr
1               5

<210> SEQ ID NO 134
<211> LENGTH: 9
<212> TYPE: PRT
```

```
<213> ORGANISM: Artificial Sequence
<220> FEATURE:
<223> OTHER INFORMATION: Synthetic sequence

<400> SEQUENCE: 134

Val Ala Gly Ala Val Trp Leu Thr Val
1               5

<210> SEQ ID NO 135
<211> LENGTH: 9
<212> TYPE: PRT
<213> ORGANISM: Artificial Sequence
<220> FEATURE:
<223> OTHER INFORMATION: Synthetic sequence

<400> SEQUENCE: 135

Trp Leu Thr Val Met Thr Asn Thr Leu
1               5

<210> SEQ ID NO 136
<211> LENGTH: 9
<212> TYPE: PRT
<213> ORGANISM: Artificial Sequence
<220> FEATURE:
<223> OTHER INFORMATION: Synthetic sequence

<400> SEQUENCE: 136

Leu Thr Val Met Thr Asn Thr Leu Leu
1               5

<210> SEQ ID NO 137
<211> LENGTH: 9
<212> TYPE: PRT
<213> ORGANISM: Artificial Sequence
<220> FEATURE:
<223> OTHER INFORMATION: Synthetic sequence

<400> SEQUENCE: 137

Val Met Thr Asn Thr Leu Leu Ser Ala
1               5

<210> SEQ ID NO 138
<211> LENGTH: 9
<212> TYPE: PRT
<213> ORGANISM: Artificial Sequence
<220> FEATURE:
<223> OTHER INFORMATION: Synthetic sequence

<400> SEQUENCE: 138

Met Thr Asn Thr Leu Leu Ser Ala Trp
1               5

<210> SEQ ID NO 139
<211> LENGTH: 9
<212> TYPE: PRT
<213> ORGANISM: Artificial Sequence
<220> FEATURE:
<223> OTHER INFORMATION: Synthetic sequence

<400> SEQUENCE: 139

Thr Leu Leu Ser Ala Trp Ile Leu Thr
1               5

<210> SEQ ID NO 140
<211> LENGTH: 9
<212> TYPE: PRT
<213> ORGANISM: Artificial Sequence
```

```
<220> FEATURE:
<223> OTHER INFORMATION: Synthetic sequence

<400> SEQUENCE: 140

Leu Leu Ser Ala Trp Ile Leu Thr Ala
1               5

<210> SEQ ID NO 141
<211> LENGTH: 9
<212> TYPE: PRT
<213> ORGANISM: Artificial Sequence
<220> FEATURE:
<223> OTHER INFORMATION: Synthetic sequence

<400> SEQUENCE: 141

Ser Ala Trp Ile Leu Thr Ala Gly Phe
1               5

<210> SEQ ID NO 142
<211> LENGTH: 9
<212> TYPE: PRT
<213> ORGANISM: Artificial Sequence
<220> FEATURE:
<223> OTHER INFORMATION: Synthetic sequence

<400> SEQUENCE: 142

Trp Ile Leu Thr Ala Gly Phe Leu Ile
1               5

<210> SEQ ID NO 143
<211> LENGTH: 9
<212> TYPE: PRT
<213> ORGANISM: Artificial Sequence
<220> FEATURE:
<223> OTHER INFORMATION: Synthetic sequence

<400> SEQUENCE: 143

Ile Leu Thr Ala Gly Phe Leu Ile Phe
1               5

<210> SEQ ID NO 144
<211> LENGTH: 9
<212> TYPE: PRT
<213> ORGANISM: Artificial Sequence
<220> FEATURE:
<223> OTHER INFORMATION: Synthetic sequence

<400> SEQUENCE: 144

Leu Thr Ala Gly Phe Leu Ile Phe Leu
1               5

<210> SEQ ID NO 145
<211> LENGTH: 9
<212> TYPE: PRT
<213> ORGANISM: Artificial Sequence
<220> FEATURE:
<223> OTHER INFORMATION: Synthetic sequence

<400> SEQUENCE: 145

Phe Leu Ile Phe Leu Ile Gly Phe Ala
1               5

<210> SEQ ID NO 146
<211> LENGTH: 9
<212> TYPE: PRT
<213> ORGANISM: Artificial Sequence
<220> FEATURE:
```

```
<223> OTHER INFORMATION: Synthetic sequence

<400> SEQUENCE: 146

Ile Phe Leu Ile Gly Phe Ala Leu Phe
1               5

<210> SEQ ID NO 147
<211> LENGTH: 9
<212> TYPE: PRT
<213> ORGANISM: Artificial Sequence
<220> FEATURE:
<223> OTHER INFORMATION: Synthetic sequence

<400> SEQUENCE: 147

Phe Leu Ile Gly Phe Ala Leu Phe Gly
1               5

<210> SEQ ID NO 148
<211> LENGTH: 9
<212> TYPE: PRT
<213> ORGANISM: Artificial Sequence
<220> FEATURE:
<223> OTHER INFORMATION: Synthetic sequence

<400> SEQUENCE: 148

Leu Ile Gly Phe Ala Leu Phe Gly Val
1               5

<210> SEQ ID NO 149
<211> LENGTH: 9
<212> TYPE: PRT
<213> ORGANISM: Artificial Sequence
<220> FEATURE:
<223> OTHER INFORMATION: Synthetic sequence

<400> SEQUENCE: 149

Gly Phe Ala Leu Phe Gly Val Ile Arg
1               5

<210> SEQ ID NO 150
<211> LENGTH: 9
<212> TYPE: PRT
<213> ORGANISM: Artificial Sequence
<220> FEATURE:
<223> OTHER INFORMATION: Synthetic sequence

<400> SEQUENCE: 150

Leu Phe Gly Val Ile Arg Cys Cys Arg
1               5

<210> SEQ ID NO 151
<211> LENGTH: 9
<212> TYPE: PRT
<213> ORGANISM: Artificial Sequence
<220> FEATURE:
<223> OTHER INFORMATION: Synthetic sequence

<400> SEQUENCE: 151

Val Pro Met Gly Ala Gly Pro Pro Ser
1               5

<210> SEQ ID NO 152
<211> LENGTH: 9
<212> TYPE: PRT
<213> ORGANISM: Artificial Sequence
<220> FEATURE:
<223> OTHER INFORMATION: Synthetic sequence
```

<400> SEQUENCE: 152

Arg Gly Arg Gly Gly Ser Gly Gly Arg
1               5

<210> SEQ ID NO 153
<211> LENGTH: 9
<212> TYPE: PRT
<213> ORGANISM: Artificial Sequence
<220> FEATURE:
<223> OTHER INFORMATION: Synthetic sequence

<400> SEQUENCE: 153

Arg Gly Arg Gly Gly Ser Gly Gly Arg
1               5

<210> SEQ ID NO 154
<211> LENGTH: 9
<212> TYPE: PRT
<213> ORGANISM: Artificial Sequence
<220> FEATURE:
<223> OTHER INFORMATION: Synthetic sequence

<400> SEQUENCE: 154

Arg Gly Arg Gly Gly Ser Gly Gly Arg
1               5

<210> SEQ ID NO 155
<211> LENGTH: 9
<212> TYPE: PRT
<213> ORGANISM: Artificial Sequence
<220> FEATURE:
<223> OTHER INFORMATION: Synthetic sequence

<400> SEQUENCE: 155

Arg Gly Arg Gly Arg Glu Arg Ala Arg
1               5

<210> SEQ ID NO 156
<211> LENGTH: 9
<212> TYPE: PRT
<213> ORGANISM: Artificial Sequence
<220> FEATURE:
<223> OTHER INFORMATION: Synthetic sequence

<400> SEQUENCE: 156

Arg Ala Arg Gly Gly Ser Arg Glu Arg
1               5

<210> SEQ ID NO 157
<211> LENGTH: 9
<212> TYPE: PRT
<213> ORGANISM: Artificial Sequence
<220> FEATURE:
<223> OTHER INFORMATION: Synthetic sequence

<400> SEQUENCE: 157

Gly Ser Arg Glu Arg Ala Arg Gly Arg
1               5

<210> SEQ ID NO 158
<211> LENGTH: 9
<212> TYPE: PRT
<213> ORGANISM: Artificial Sequence
<220> FEATURE:
<223> OTHER INFORMATION: Synthetic sequence

<400> SEQUENCE: 158

Arg Ala Arg Gly Arg Gly Arg Gly Arg
1               5

<210> SEQ ID NO 159
<211> LENGTH: 9
<212> TYPE: PRT
<213> ORGANISM: Artificial Sequence
<220> FEATURE:
<223> OTHER INFORMATION: Synthetic sequence

<400> SEQUENCE: 159

Arg Gly Arg Gly Arg Gly Glu Lys Arg
1               5

<210> SEQ ID NO 160
<211> LENGTH: 9
<212> TYPE: PRT
<213> ORGANISM: Artificial Sequence
<220> FEATURE:
<223> OTHER INFORMATION: Synthetic sequence

<400> SEQUENCE: 160

Arg Gly Arg Gly Glu Lys Arg Pro Arg
1               5

<210> SEQ ID NO 161
<211> LENGTH: 9
<212> TYPE: PRT
<213> ORGANISM: Artificial Sequence
<220> FEATURE:
<223> OTHER INFORMATION: Synthetic sequence

<400> SEQUENCE: 161

Ser Ser Ser Ser Gly Ser Pro Pro Arg
1               5

<210> SEQ ID NO 162
<211> LENGTH: 9
<212> TYPE: PRT
<213> ORGANISM: Artificial Sequence
<220> FEATURE:
<223> OTHER INFORMATION: Synthetic sequence

<400> SEQUENCE: 162

His Pro Val Gly Asp Ala Asp Tyr Phe
1               5

<210> SEQ ID NO 163
<211> LENGTH: 9
<212> TYPE: PRT
<213> ORGANISM: Artificial Sequence
<220> FEATURE:
<223> OTHER INFORMATION: Synthetic sequence

<400> SEQUENCE: 163

Lys Gly Gly Trp Phe Gly Lys His Arg
1               5

<210> SEQ ID NO 164
<211> LENGTH: 9
<212> TYPE: PRT
<213> ORGANISM: Artificial Sequence
<220> FEATURE:
<223> OTHER INFORMATION: Synthetic sequence

<400> SEQUENCE: 164

```
Arg Gly Arg Gly Arg Gly Arg Gly Arg
1               5
```

<210> SEQ ID NO 165
<211> LENGTH: 9
<212> TYPE: PRT
<213> ORGANISM: Artificial Sequence
<220> FEATURE:
<223> OTHER INFORMATION: Synthetic sequence

<400> SEQUENCE: 165

```
Glu Gly Leu Arg Val Leu Leu Ala Arg
1               5
```

<210> SEQ ID NO 166
<211> LENGTH: 9
<212> TYPE: PRT
<213> ORGANISM: Artificial Sequence
<220> FEATURE:
<223> OTHER INFORMATION: Synthetic sequence

<400> SEQUENCE: 166

```
Arg Val Leu Leu Ala Arg Ser His Val
1               5
```

<210> SEQ ID NO 167
<211> LENGTH: 9
<212> TYPE: PRT
<213> ORGANISM: Artificial Sequence
<220> FEATURE:
<223> OTHER INFORMATION: Synthetic sequence

<400> SEQUENCE: 167

```
Leu Leu Ala Arg Ser His Val Glu Arg
1               5
```

<210> SEQ ID NO 168
<211> LENGTH: 9
<212> TYPE: PRT
<213> ORGANISM: Artificial Sequence
<220> FEATURE:
<223> OTHER INFORMATION: Synthetic sequence

<400> SEQUENCE: 168

```
Arg Gly Arg Gly Arg Gly Gly Gly Arg
1               5
```

<210> SEQ ID NO 169
<211> LENGTH: 9
<212> TYPE: PRT
<213> ORGANISM: Artificial Sequence
<220> FEATURE:
<223> OTHER INFORMATION: Synthetic sequence

<400> SEQUENCE: 169

```
Gly Val Phe Val Tyr Gly Gly Ser Lys
1               5
```

<210> SEQ ID NO 170
<211> LENGTH: 9
<212> TYPE: PRT
<213> ORGANISM: Artificial Sequence
<220> FEATURE:
<223> OTHER INFORMATION: Synthetic sequence

<400> SEQUENCE: 170

```
Lys Thr Ser Leu Tyr Asn Leu Arg Arg
1               5
```

<210> SEQ ID NO 171
<211> LENGTH: 9
<212> TYPE: PRT
<213> ORGANISM: Artificial Sequence
<220> FEATURE:
<223> OTHER INFORMATION: Synthetic sequence

<400> SEQUENCE: 171

```
Ile Ala Leu Ala Val Pro Gln Cys Arg
1               5
```

<210> SEQ ID NO 172
<211> LENGTH: 9
<212> TYPE: PRT
<213> ORGANISM: Artificial Sequence
<220> FEATURE:
<223> OTHER INFORMATION: Synthetic sequence

<400> SEQUENCE: 172

```
Ile Thr Pro Leu Ser Arg Leu Pro Phe
1               5
```

<210> SEQ ID NO 173
<211> LENGTH: 9
<212> TYPE: PRT
<213> ORGANISM: Artificial Sequence
<220> FEATURE:
<223> OTHER INFORMATION: Synthetic sequence

<400> SEQUENCE: 173

```
Arg Glu Ser Ile Val Cys Tyr Phe Met
1               5
```

<210> SEQ ID NO 174
<211> LENGTH: 9
<212> TYPE: PRT
<213> ORGANISM: Artificial Sequence
<220> FEATURE:
<223> OTHER INFORMATION: Synthetic sequence

<400> SEQUENCE: 174

```
Glu Ser Ile Val Cys Tyr Phe Met Val
1               5
```

<210> SEQ ID NO 175
<211> LENGTH: 9
<212> TYPE: PRT
<213> ORGANISM: Artificial Sequence
<220> FEATURE:
<223> OTHER INFORMATION: Synthetic sequence

<400> SEQUENCE: 175

```
Ser Ile Val Cys Tyr Phe Met Val Phe
1               5
```

<210> SEQ ID NO 176
<211> LENGTH: 9
<212> TYPE: PRT
<213> ORGANISM: Artificial Sequence
<220> FEATURE:
<223> OTHER INFORMATION: Synthetic sequence

<400> SEQUENCE: 176

```
Ile Val Cys Tyr Phe Met Val Phe Leu
```

```
1               5
```

<210> SEQ ID NO 177
<211> LENGTH: 9
<212> TYPE: PRT
<213> ORGANISM: Artificial Sequence
<220> FEATURE:
<223> OTHER INFORMATION: Synthetic sequence

<400> SEQUENCE: 177

```
Phe Met Val Phe Leu Gln Thr His Ile
1               5
```

<210> SEQ ID NO 178
<211> LENGTH: 9
<212> TYPE: PRT
<213> ORGANISM: Artificial Sequence
<220> FEATURE:
<223> OTHER INFORMATION: Synthetic sequence

<400> SEQUENCE: 178

```
Met Val Phe Leu Gln Thr His Ile Phe
1               5
```

<210> SEQ ID NO 179
<211> LENGTH: 9
<212> TYPE: PRT
<213> ORGANISM: Artificial Sequence
<220> FEATURE:
<223> OTHER INFORMATION: Synthetic sequence

<400> SEQUENCE: 179

```
Phe Leu Gln Thr His Ile Phe Ala Glu
1               5
```

<210> SEQ ID NO 180
<211> LENGTH: 9
<212> TYPE: PRT
<213> ORGANISM: Artificial Sequence
<220> FEATURE:
<223> OTHER INFORMATION: Synthetic sequence

<400> SEQUENCE: 180

```
Leu Gln Thr His Ile Phe Ala Glu Val
1               5
```

<210> SEQ ID NO 181
<211> LENGTH: 9
<212> TYPE: PRT
<213> ORGANISM: Artificial Sequence
<220> FEATURE:
<223> OTHER INFORMATION: Synthetic sequence

<400> SEQUENCE: 181

```
Ala Ile Lys Asp Leu Val Met Thr Lys
1               5
```

<210> SEQ ID NO 182
<211> LENGTH: 9
<212> TYPE: PRT
<213> ORGANISM: Artificial Sequence
<220> FEATURE:
<223> OTHER INFORMATION: Synthetic sequence

<400> SEQUENCE: 182

```
Asn Ile Lys Val Thr Val Cys Ser Phe
1               5
```

```
<210> SEQ ID NO 183
<211> LENGTH: 9
<212> TYPE: PRT
<213> ORGANISM: Artificial Sequence
<220> FEATURE:
<223> OTHER INFORMATION: Synthetic sequence

<400> SEQUENCE: 183

Thr Val Cys Ser Phe Asp Asp Gly Val
1               5

<210> SEQ ID NO 184
<211> LENGTH: 9
<212> TYPE: PRT
<213> ORGANISM: Artificial Sequence
<220> FEATURE:
<223> OTHER INFORMATION: Synthetic sequence

<400> SEQUENCE: 184

Phe Pro Pro Met Val Glu Gly Ala Ala
1               5
```

METHOD FOR ACTIVATING T CELLS FOR CANCER TREATMENT

CROSS REFERENCE TO RELATED APPLICATIONS

This application is a U.S. National Stage of International Application No. PCT/KR2018/009224, filed Aug. 10, 2018, which claims the benefit of priority from Korean Patent Application No. 10-2017-0101800, filed Aug. 10, 2017. The entire contents of these applications are incorporated herein by reference in their entirety.

INCORPORATION BY REFERENCE OF MATERIAL SUBMITTED ELECTRONICALLY

Incorporated by reference in its entirety is a computer-readable nucleotide/amino acid sequence listing submitted concurrently herewith and identified as follows: ASCII (text) file named "55299 SubSeqlisting.txt," 35,819 bytes, created on May 22, 2020.

TECHNICAL FIELD

The present invention relates to a cancer-specific tumor antigen neoepitope, an antigen-presenting cell loaded with the neoepitope, and a method for activating T cells for cancer treatment using the antigen-presenting cell.

BACKGROUND ART

Gastric cancer is known as a malignancy with a high incidence in the world, especially in Asia. There have been many known causes of development of gastric cancer; however, gastric cancer may be typically classified into EBV-associated gastric cancer, which is caused by infection with Epstein-Barr virus (EBV), and gastric cancer cell antigen-associated gastric cancer, which is caused by accumulation of genetic mutations in gastrointestinal cells. For current treatment for gastric cancer, excision of cancerous tissue has long been known to be the most effective, and chemotherapy and radiation therapy are also performed. However, it appears that gastric cancer is a hard-to-cure disease when not found early. In addition, although clinical trials have been conducted through several biological agents (antibodies, small molecules), therapeutic agents with good clinical effects have not yet been reported.

Recently, cancer cell-specific targeted therapy using patient-derived autologous T cells has been studied in several institutions, and clinical trials have been conducted for lymphoma using chimeric antigen receptor (CAR) T cells in several institutions. As a result, due to good clinical effects and low side effects, such therapy has attracted much attention as a new field of anticancer therapy.

Use of patient-derived T cells decreases induction of immune responses which is the biggest side effect of cell therapeutic agents, and removes restrictions on the donor's HLA type. Thus, such T cells have been known as therapeutic agents which are effective and have no side effects. To date, CD8+ T cells, CD4+ T cells, NK cells, dendritic cells, and CAR T cells are known as types of cell therapeutic agents which are most widely used in the field of anticancer therapy. NK cells have cell-killing efficacy, and have several side effects due to not having antigen specificity. Dendritic cells are therapeutic agents belonging to the vaccine concept in that they have no function of directly killing cells, and are capable of delivering antigen specificity to T cells in the patient's body so that cancer cell specificity is imparted to T cells with high efficiency. In addition, CD4+ T cells play a role in helping other cells through antigen specificity, and CD8+ T cells are known to have the best antigen specificity and cell-killing effect.

However, most cell therapeutic agents, which have been used or developed to date, have limitations and thus have no clinical effect. Taking a look at the limitations, cancer cells, on their own, secrete substances that suppress immune responses in the human body, or do not present antigens necessary for production of antibodies against such cancer cells, thereby preventing an appropriate immune response from occurring.

Meanwhile, dendritic cells not only act as surveillants to detect antigens that come from the outside of the human body or are produced internally, but also quickly travel to the secondary lymphoid organs with such recognized and absorbed antigen, thereby acting as specialized antigen-presenting cells that present the antigens to immune cells, including T cells, which react with the antigens. Anti-cancer immunotherapeutic vaccines using dendritic cells have been developed through several methods, and may be largely divided into ex vivo generated dendritic cell vaccines and in vivo dendritic cell vaccines. The in vivo dendritic cell vaccine works in a manner of directly delivering an antigen to dendritic cells present in the body. In addition, a method using the ex vivo generated dendritic cell vaccine is in such a manner that dendritic cells are isolated from the patient's PBMCs and an antigen to be presented is delivered to the isolated dendritic cells, through which the dendritic cells are activated and then injected back into the patient so that the antigen is delivered from the injected dendritic cells to T cells. In the latter, ex vivo dendritic cell culture method and antigen delivery method are important, and currently used antigen presentation methods include transfection of DNA of an antigen to be presented using virus or nucleofection, or antigen delivery targeting dendritic cells in which an antigen is bound to an antibody targeting the dendritic cells.

Currently, the biggest problems in dendritic cell vaccines are that severe chronic inflammatory phenomena in the body and the Warburg effect are exhibited, and it is considered very difficult to achieve effective activation of anticancer immune cells under the cancer microenvironment in which immunosuppressive cytokines, immunosuppressive T cells, dendritic cells, and the like are present.

Technical Problem

An object of the present invention is to provide an Epstein-Barr virus (EBV)-positive cancer-specific tumor antigen neoepitope, and a composition for activating T cells which comprises the same.

Another object of the present invention is to provide an antigen-presenting cell loaded with a neoepitope of the present invention, the antigen-presenting cell being capable of activating T cells for cancer treatment.

Yet another object of the present invention is to provide a T cell, activated by the antigen-presenting cell loaded with a neoepitope of the present invention.

Still yet another object of the present invention is to provide a method for activating T cells for cancer treatment.

However, the technical problem to be solved by the present invention is not limited to the above-mentioned problems, and other problems which are not mentioned will be clearly understood by those skilled in the art from the following description.

Solution to Problem

According to an embodiment of the present invention, there is provided a cancer-specific tumor antigen epitope.

In the present invention, the "cancer-specific tumor antigen epitope" is derived from a protein antigen which is present only in cancer cells and is not present in normal cells. In the present invention, the cancer-specific tumor antigen epitope includes at least one epitope recognized by T cell receptors; and such an epitope may preferably include epitopes present in Epstein-Barr virus (EBV)-positive cancer cells, including the EBV viral epitopes or cancer cell epitopes, and may more preferably be the Epstein-Barr virus (EBV)-positive cancer cell antigen which is Epstein-Barr virus latent membrane protein 2 (LMP2a), or Epstein-Barr nuclear antigen 1 (EBNA-1), or a neoepitope thereof.

In the present invention, the "Epstein-Barr virus latent membrane protein 2 (LMP2a)" is one of several EBV genes expressed in all of type II and III diseases/malignancies. LMP2a corresponds to a transmembrane protein that acts as a negative modulator of B cell-receptor signaling and promotes cell survival through sequestering of tyrosine kinases. HLA-A2-restricted peptides are epitope-specific cytotoxic T lymphocytes, which are detectable ex vivo in 60% to 75% of individuals, and are the most immunodominant LMP epitopes in latent diseases. The CLGGLLTMV peptide has long been seen to be a potential target for NPC and HL treatments, since the epitope is conserved in biopsies taken from NPC and HL patients and, along with other EBV latent epitopes, is immunologically weak.

In the present invention, the "Epstein-Barr nuclear antigen 1 (EBNA-1)" corresponds to a multifunctional, dimeric viral protein associated with Epstein-Barr virus. This corresponds to an EBV protein found only in all EBV-associated malignancies. This plays an important role in maintaining the altered state that cells take when the cells are infected with EBV. EBNA-1, on the other hand, corresponds to a glycine-alanine repeat sequence that separates a protein into amino- and carboxy-terminal domains. This sequence serves to stabilize a protein, prevent proteasomal breakdown, and impair antigen processing and MHC class I-restricted antigen presentation. Thus, the EBNA-1 inhibits CD8-restricted cytotoxic T cell responses against virus-infected cells. The EBNA-1 is expressed by Qp promoter in all latency programs and corresponds to the only viral protein expressed in latency program I.

In the present invention, the "neoepitope" refers to an epitope that is not present in a reference such as normal, non-cancerous cells or germline cells and is found in cancer cells.

In the present invention, the neoepitope may exhibit binding affinity with at least one of HLA-A, HLA-B, HLA-C, HLA-E, HLA-F, HLA-G, β2-microglobulin, HLA-DPA1, HLA-DPB1, HLA-DQA1, HLA-DQB1, HLA-DRA1, HLA-DRB1, HLA-DRB3, HLA-DRB4, HLA-DRB5, HLA-DM, HLA-DOA, and HLA-DOB loci so that T cells, preferably memory T cells, extracted from human blood can have efficacy. Among these, the neoepitope may include those exhibiting high binding affinity with at least one of the HLA types that are most expressed by Koreans, for example, HLA-A*2402, HLA-A*A0201, HLA-A*3303, HLA-A*1101, HLA-A*0206, HLA-A*3101, HLA-B*5101, HLA-B*4403, HLA-B*5401, HLA-B*5801, and HLA-B*3501.

Preferably, in the present invention, the neoepitope has high binding affinity for HLA-A*2402 and may include neoepitopes of LMP2a antigen which is a peptide represented by any one of SEQ ID NOs: 1 to 151; or has high binding affinity for HLA-A*3101 and may include neoepitopes of EBNA-1 antigen which is a peptide represented by any one of SEQ ID NOs: 152 to 184.

Here, in the present invention, for a method of measuring neoepitope-HLA affinity, NetMHC 3.4 (URL: www.cbs.dtu.dk/services/NetMHC-3.4/) may be used to predict whether a neoepitope binds to a specific HLA allele. However, the present invention is not limited thereto.

In the present invention, the "HLA" or "human leukocyte antigen" refers to human gene that encodes a major histocompatibility complex (MHC) protein on the surface of cells that are responsible for regulation of the immune system. "HLA-I" or "HLA class I" refers to human MHC class I gene including HLA-A, HLA-B, HLA-C, HLA-E, HLA-F, HLA-G, and β2-microglobulin loci. "HLA-II" or "HLA class II" refers to human MHC class II gene including HLA-DPA1, HLA-DPB1, HLA-DQA1, HLA-DQB1, HLA-DRA1, HLA-DRB1, HLA-DRB3, HLA-DRB4, HLA-DRB5, HLA-DM, HLA-DOA, and HLA-DOB loci.

In the present invention, the cancer may be Epstein-Barr virus (EBV)-positive cancer, including EBV-positive gastric cancer, EBV-positive cervical cancer, EBV-positive Burkitt's lymphoma, EBV-positive T cell lymphoma, EBV-positive breast cancer, EBV-positive leiomyosarcoma, EBV-positive smooth muscle tumor, EBV-positive Hodgkin lymphoma, EBV-positive nasopharyngeal cancer, or EBV-positive post-transplant lymphoproliferative disorder (PTLD), with EBV-positive gastric cancer being preferred.

According to another embodiment of the present invention, there is provided a nucleic acid molecule, encoding a cancer-specific tumor antigen epitope provided in the present invention, preferably a neoepitope of LMP2a or EBNA-1 which is an antigen of Epstein-Barr virus (EBV)-positive cancer cells.

The nucleic acid molecule of the present invention includes any nucleic acid molecule obtained by converting an amino acid sequence of a polypeptide provided in the present invention into a polynucleotide sequence as known to those skilled in the art. Thus, various polynucleotide sequences may be prepared due to open reading frame (ORF), all of which are also included in the nucleic acid molecule of the present invention.

According to yet another embodiment of the present invention, there is provided an expression vector, into which the isolated nucleic acid molecule provided in the present invention is inserted.

In the present invention, the "vector" is a nucleic acid molecule which is capable of transporting another nucleic acid linked thereto. One type of vector is a "plasmid," which refers to circular double-stranded DNA into which an additional DNA segment can be ligated. Another type of vector is a phage vector. Yet another type of vector is a viral vector, where an additional DNA segment can be ligated into the viral genome. Certain vectors are capable of autonomous replication in a host cell into which they are introduced (for example, bacterial vectors having a bacterial origin of replication and episomal mammalian vectors). Other vectors (for example, non-episomal mammalian vectors) can be integrated into the genome of a host cell upon introduction into the host cell, and thus are replicated along with the host genome. In addition, certain vectors are capable of directing expression of genes to which they are operatively linked. Such vectors are referred to herein as "recombinant expression vectors" or simply "expression vectors." In general, expression vectors useful in recombinant DNA techniques are often in the form of plasmids. In the present specification, "plasmid" and "vector" may be used interchangeably as the plasmid is the most commonly used form among vectors.

Specific examples of the expression vector in the present invention may be selected from, but are not limited to, the group consisting of commercially widely used pCDNA vectors, F, R1, RP1, Col, pBR322, ToL, Ti vectors; cosmids; phages such as lambda, lambdoid, M13, Mu, p1 P22, Qμ, T-even, T2, T3, T7; plant viruses. Any expression vector known, to those skilled in the art, as expression vectors can be used in the present invention, and the expression vector is selected depending on the nature of the target host cell. Introduction of a vector into a host cell may be performed by calcium phosphate transfection, viral infection, DEAE-dextran-mediated transfection, lipofectamine transfection, or electroporation. However, the present invention is not limited thereto, and those skilled in the art may adopt and use an introduction method appropriate for the expression vector and the host cell which are used. The vector may preferably contain at least one selection marker. However, the present invention is not limited thereto, and selection can be made using the vector that contains no selection marker, depending on whether or not a product is produced. The selection marker is selected depending on the target host cell, which is done using methods already known to those skilled in the art, and thus the present invention has no limitation thereon.

In order to facilitate purification of the nucleic acid molecule of the present invention, a tag sequence may be inserted into and fused to an expression vector. The tag includes, but is not limited to, hexa-histidine tag, hemagglutinin tag, myc tag, or flag tag, and any tag known to those skilled in the art which facilitates purification can be used in the present invention.

According to still yet another embodiment of the present invention, there is provided a host cell, transfected with the expression vector provided in the present invention.

In the present invention, the "host cell" includes individual cells or cell cultures which may be or have been recipients of the vector(s) for incorporation of a polypeptide insert. The host cell includes progeny of a single host cell, and the progeny may not necessarily be completely identical (in morphology or in genomic DNA complement) to the original parent cell due to natural, accidental, or intentional mutation. The host cell includes cells transfected in vivo with the polynucleotide(s) herein.

In the present invention, the host cell may include cells of mammalian, plant, insect, fungal, or cellular origin, and may be, for example, bacterial cells such as *E. coli, Streptomyces, Salmonella typhimurium*; fungal cells such as yeast cells and *Pichia pastoris*; insect cells such as *Drosophila* and *Spodoptera* Sf9 cells; animal cells such as Chinese hamster ovary (CHO) cells, SP2/0 (mouse myeloma), human lymphoblastoid, COS, NSO (mouse myeloma), 293T, Bowes melanoma cells, HT-1080, baby hamster kidney (BHK) cells, human embryonic kidney (HEK) cells, or PERC.6 (human retinal cells); or plant cells. However, the host cell is not limited thereto, and any cell known to those skilled in the art which can be used as a host cell is available.

According to still yet another embodiment of the present invention, there is provided a composition for activating T cells, comprising a cancer-specific tumor antigen epitope provided in the present invention, a nucleic acid molecule encoding the same, an expression vector into which the nucleic acid molecule is inserted, or a host cell transformed with the expression vector.

As used herein, the term "activation of T cells" refers to a population of monoclonal (for example, encoding the same TCR) or polyclonal (for example, having clones encoding different TCRs) T cells that have T cell receptors recognizing at least one tumor antigen peptide. Activated T cells may include one or more subtypes of T cells, including, but not limited to, one or more selected from the group consisting of cytotoxic T cells, helper T cells, natural killer T cells, γδT cells, regulatory T cells, and memory T cells, with memory T cells being preferred.

In the present invention, the activated T cells can treat a cancerous or neoplastic condition or prevent recurrence, progression, or metastasis of cancer while avoiding the defense mechanism of cancer cells.

According to still yet another embodiment of the present invention, there may be provided an antigen-presenting cell (APC) loaded with a cancer-specific tumor antigen epitope provided in the present invention.

In the present invention, the antigen-presenting cells may include at least one of dendritic cell (DC), B cell, and macrophage, with dendritic cell being preferred.

In the present invention, the "dendritic cell" refers to any member of a diverse population of morphologically similar cell types found in lymphoid or non-lymphoid tissues. These cells are characterized by their distinctive morphology and high expression levels of surface class I and class II MHC molecules, which are proteins that present antigenic peptides to T cells. DCs, other APCs, and T cells may be isolated or derived (such as differentiated) from a number of tissue sources, and conveniently from peripheral blood, such as peripheral blood mononuclear cells (PBMCs) derived from peripheral blood.

In the present invention, the antigen-presenting cell can induce differentiation and proliferation of cancer antigen-specific T cells, preferably memory T cells, thereby treating a cancerous or neoplastic condition or preventing recurrence, progression, or metastasis of cancer while avoiding the defense mechanism of cancer cells.

According to still yet another embodiment of the present invention, there is provided a fusion protein, comprising: a cancer-specific tumor antigen epitope provided in the present invention; and a dendritic cell-specific antibody or a fragment thereof.

The fusion protein provided in the present invention enables the cancer-specific tumor antigen epitope provided in the present invention to be loaded on dendritic cells.

In the present invention, the dendritic cell-specific antibody may include, but is not limited to, antibodies specific for DCIR, MHC class I, MHC class II, CD1, CD2, CD3, CD4, CD8, CD11b, CD14, CD15, CD16, CD19, CD20, CD29, CD31, CD40, CD43, CD44, CD45, CD54, CD56, CD57, CD58, CD83, CD86, CMRF-44, CMRF-56, DCIR, DC-ASPGR, CLEC-6, CD40, BDCA-2, MARCO, DEC-205, Clec9A, 33D1, mannose receptor, Langerin, DECTIN-1, B7-1, B7-2, IFN-γ receptor, IL-2 receptor, ICAM-1, Fcγ receptor, LOX-1, or ASPGR, which is on dendritic cells.

The cancer-specific tumor antigen epitope in the fusion protein of the present invention may be conjugated to the dendritic cell-specific antibody or a fragment thereof. Here, the term "conjugate" refers to any material formed by joining two parts together. A representative conjugate according to the present invention includes those formed by joining an antigen together with an antibody and a TLR agonist. The term "conjugation" refers to a process of forming a conjugate and generally indicates physical coupling, for example, covalent bond, co-coordinate covalent bond, or second binding force, for example, Van der Waals binding force. The process of linking the antigen to the antibody may also be done via a non-covalent association such as a dockerin-cohesin association (as described in U.S. Patent Publication No. 20100135994, Banchereau et al. relevant portions incorporated herein by reference) or via a direct chemical linkage by forming a peptide or chemical bond.

According to another embodiment of the present invention, there is provided a method for producing an antigen-presenting cell, in which the antigen-presenting cell is loaded with a cancer-specific tumor antigen epitope provided in the present invention.

In the present invention, the antigen-presenting cell may include one or more of dendritic cell, B cell, and macrophage, with dendritic cell being preferred.

In the present invention, the dendritic cells (such as immature dendritic cells) may be obtained from a variety of sources including autologous sources, that is, derived from a target individual. The dendritic cells may preferably be obtained from peripheral blood mononuclear cells (PBMCs) derived from peripheral blood, and more preferably be obtained by isolating monocytes from individual-derived PBMCs and contacting the monocytes with a plurality of cytokines. Here, the type of cytokine that induces differentiation of the monocytes into dendritic cells is not particularly limited, and may include, for example, one or more of GM-CSF and IL-4.

In the present invention, the "target individual" means an individual who has or is at high risk of developing cancer.

In the present invention, once antigen-presenting cells are prepared as described above, the antigen-presenting cells may be loaded with a cancer-specific tumor antigen epitope of the present invention. In general, immature dendritic cells capture an antigen through phagocytosis or receptor-mediated endocytosis, process the antigen through a series of intracellular processes and then cause an antigenic peptide to be loaded on MHC and presented to T lymphocytes. With the process of processing an antigen, the dendritic cells become more mature, which makes them lose receptors used for phagocytosis and endocytosis, exhibit increased expression of MHC class I, II, costimulatory molecules, and adhesion molecules, and express new chemokine receptors. This allows the dendritic cells to migrate to T lymphocyte-rich areas of the surrounding lymph nodes, and to present the antigen to T lymphocytes, thereby causing a T lymphocyte immune response.

In an example of the present invention, in order for the cancer-specific tumor antigen epitope to be loaded on the antigen-presenting cell, the antigen-presenting cell may be contacted with the cancer-specific tumor antigen epitope of the present invention, and preferably, a step of pulsing, with the cancer-specific tumor antigen epitope of the present invention, the antigen-presenting cells, for example, immature dendritic cells, or antigen-presenting cells (such as dendritic cells) contained in or derived (for example, differentiated) from PBMCs may be performed. As known in the art, pulsing refers to a process of mixing cells, such as dendritic cells, with a solution containing a cancer-specific tumor antigen epitope peptide of the present invention, and then optionally removing the cancer-specific tumor antigen epitope peptide from the mixture. In the present invention, when the immature dendritic cells are contacted with the cancer-specific tumor antigen epitope, treatment with toll-like receptor agonists may be performed to further induce maturation of a population of immature dendritic cells. Here, exemplary TLR agonists include, but are not limited to, polyIC, MALP, and R848.

In another example of the present invention, in order for the cancer-specific tumor antigen epitope to be loaded on the antigen-presenting cell, it is possible to perform nucleofection of the antigen-presenting cell with an expression vector, preferably a plasmid, into which a nucleic acid molecule encoding the cancer-specific tumor antigen epitope is inserted. Here, the nucleofection may be performed by any useful means in the art, including, for example, Amaxa® nucleofection system or InVitrogen® nucleofection system.

In yet another example of the present invention, in order for the cancer-specific tumor antigen epitope to be loaded on the antigen-presenting cell, such loading may be performed using a fusion protein that contains the cancer-specific tumor antigen epitope provided in the present invention; and a dendritic cell-specific antibody or a fragment thereof.

According to still yet another embodiment of the present invention, there is provided a T cell activated by an antigen-presenting cell provided in the present invention.

In the present invention, the T cells refer to a population of monoclonal (for example, encoding the same TCR) or polyclonal (for example, having clones encoding different TCRs) T cells that have T cell receptors recognizing a tumor antigen peptide, and may include one or more subtypes of T cells, including, but not limited to, one or more selected from the group consisting of cytotoxic T cells, helper T cells, natural killer T cells, γδ T cells, regulatory T cells, and memory T cells, with memory T cells being preferred.

In the present invention, the "memory T cells" are T cells that have previously encountered and responded to their specific antigen, or T cells that have differentiated from activated T cells. Although tumor-specific memory T cells make up a small portion of the total T cell amount, they play an important function in surveillance of tumor cells during a person's entire lifespan. In a case where tumor-specific memory T cells encounter tumor cells that express their specific tumor antigen, the memory T cells are immediately activated and clonally expanded. The activated and expanded T cells differentiate into effector T cells to kill tumor cells with high efficiency. Memory T cells are important for establishing and maintaining long-term tumor antigen-specific responses of T cells. In the present invention, activated T cells, preferably activated memory T cells, specifically recognize antigens on cancer cells, so that such T cells can treat a cancerous or neoplastic condition or prevent recurrence, progression, or metastasis of cancer while avoiding the defense mechanism of cancer cells.

According to still yet another embodiment of the present invention, there is provided a method for activating T cells using an antigen-presenting cell (APC) provided in the present invention.

In the present invention, for activation of the T cells, the T cells may be co-cultured with antigen-presenting cells loaded with a cancer-specific tumor antigen epitope of the present invention.

In the present invention, the T cells may be obtained from various sources including autologous sources, that is, derived from a target individual, may preferably be obtained from peripheral blood mononuclear cells (PBMCs) derived from peripheral blood, and may more preferably be obtained from non-adherent portions of the peripheral blood mononuclear cells. In an example of the present invention, the non-adherent portions of the PBMCs may be obtained by density gradient centrifugation of a peripheral blood sample, or may be obtained by performing culture with at least one cytokine (such as IL-2) in the presence or absence of an anti-CD3 antibody (such as OKT3).

In the present invention, the T cells refer to a population of monoclonal (for example, encoding the same TCR) or polyclonal (for example, having clones encoding different TCRs) T cells that have T cell receptors recognizing a tumor antigen peptide, and may include one or more subtypes of T cells, including, but not limited to, one or more selected from the group consisting of cytotoxic T cells, helper T cells, natural killer T cells, γδ T cells, regulatory T cells, and memory T cells, with memory T cells being preferred.

In addition, in the present invention, the T cells and the antigen-presenting cells may be derived from the same individual, such as an individual suffering from cancer, preferably EBV-positive cancer (for example, low to medium grade cancer). However, the present invention is not limited thereto.

In the present invention, for activation of the T cells, the T cells may be co-cultured with antigen-presenting cells of the present invention for any one or more time periods of 1, 2, 3, 4, 6, 8, 10, 12, 14, 16, 18, 20, 22, 24, 26, 28, or 30 days, and preferably for 1 to 21 days, 1 to 14 days, 2 to 10 days, 2 to 5 days, 2 to 5 days, 3 days, 5 days, 7 days, 10 days, 14 days, 16 days, 18 days, or 21 days. However, the present invention is not limited thereto.

In the present invention, during the co-culture of the T cells with antigen-presenting cells of the present invention, one or more cytokines may be added to prime the T cells so that activation, maturation and/or proliferation of the T cells are promoted and the T cells subsequently differentiate into memory T cells. Exemplary cytokines that may be used at this stage include, but are not limited to, interleukin-2 (IL-2), interleukin-4 (IL-4), interleukin-7 (IL-7), interleukin-15 (IL-15), interleukin-21 (IL-21), or combinations thereof, and the like.

In addition, in the present invention, during the co-culture of the T cells with antigen-presenting cells of the present invention, a fusion protein comprising a cytokine and an immunoglobulin heavy chain constant region may be added to prime the T cells so that activation, maturation and/or proliferation of the T cells are promoted and the T cells subsequently differentiate into memory T cells. Here, the cytokine may include, but is not limited to, interferon-γ (IFN-γ), interleukin-2 (IL-2), interleukin-4 (IL-4), interleukin-12 (IL-12), IL-18, and tumor necrosis factor (TNF), or granulocyte macrophage colony stimulating factor (GMCSF). The immunoglobulin heavy chain constant region may also be, but is not limited to, an immunoglobulin hinge region, and an immunoglobulin heavy chain constant region optionally selected from the group consisting of CH2 domain, CH3 domain, and CH4 domain, or combinations thereof. In addition, the immunoglobulin heavy chain constant region may be derived from immunoglobulins belonging to any of five immunoglobulin classes called in the art as IgA (Igα), IgD (Igδ), IgE (Igε), IgG (Igγ), and IgM (Igμ), and may preferably be an immunoglobulin heavy chain constant region derived from the IgG class.

In addition, in the present invention, during the co-culture of the T cells with antigen-presenting cells of the present invention, a fusion protein that contains ligand binding to a cell surface protein which is highly expressed in memory T cells; and an immunoglobulin heavy chain constant region, may be added to prime the T cells so that activation, maturation and/or proliferation of the T cells are promoted and the T cells subsequently differentiate into memory T cells. Here, the cell surface protein which is highly expressed in memory T cells may be CD27, CXCR3, or CD62L. The ligand capable of binding to CD27 may be CD70; the ligand capable of binding to CXCR3 may be CXCR9 or CXCR10; and the ligand capable of binding to CD62L may be GlyCAM-1, CD34, MadCAM-1, or PSGL-1. However, the present invention is not limited thereto. In addition, the immunoglobulin heavy chain constant region may be derived from immunoglobulins belonging to any of five immunoglobulin classes called in the art as IgA (Igα), IgD (Igδ), IgE (Igε), IgG (Igγ), and IgM (Igμ), and may preferably be an immunoglobulin heavy chain constant region derived from the IgG class.

According to still yet another embodiment of the present invention, there is provided an immunotherapeutic agent, comprising, as an active ingredient, an antigen-presenting cell loaded with a cancer-specific tumor antigen epitope provided in the present invention. The immunotherapeutic agent according to the present invention can increase immune responses or may selectively increase some of immune responses desired for treatment or prevention of a certain disease, for example, cancer.

According to still yet another embodiment of the present invention, there is provided an anticancer vaccine or a pharmaceutical composition for preventing or treating cancer, comprising, as an active ingredient, an antigen-presenting cell loaded with a cancer-specific tumor antigen epitope provided in the present invention; and/or an activated T cell.

As used herein, the term "cancer" refers to or indicates a physiological condition characterized by cell growth in mammals which is not regulated in a typical manner. The cancer to be prevented, ameliorated, or treated in the present invention may be Epstein-Barr virus (EBV)-positive cancer, including, but not limited to, EBV-positive gastric cancer, EBV-positive cervical cancer, EBV-positive Burkitt's lymphoma, EBV-positive T cell lymphoma, EBV-positive breast cancer, EBV-positive leiomyosarcoma, EBV-positive smooth muscle tumor, EBV-positive Hodgkin lymphoma, EBV-positive nasopharyngeal cancer, or EBV-positive post-transplant lymphoproliferative disorder (PTLD), with EBV-positive gastric cancer being preferred.

The antigen-presenting cell provided in the present invention enables induction of differentiation and proliferation of EBV-positive cancer antigen-specific T cells, preferably memory T cells, and the memory T cells thus activated can treat a cancerous or neoplastic condition or prevent recurrence, progression, or metastasis of cancer while avoiding the defense mechanism of cancer cells.

The anticancer vaccine according to the present invention may involve both an immunization method performed by single administration and an immunization method performed by continuous administration. In the present invention, the "prevention" may include, without limitation, any act of blocking symptoms of cancer, or suppressing or delaying the symptoms, using the pharmaceutical composition of the present invention.

In addition, in the present invention, the "treatment" may include, without limitation, any act of ameliorating or beneficially altering symptoms of cancer, using the pharmaceutical composition of the present invention.

In the present invention, the pharmaceutical composition may be characterized by being in the form of capsules, tablets, granules, injections, ointments, powders, or beverages, and the pharmaceutical composition may be characterized by being targeted to humans.

In the present invention, the pharmaceutical composition may be formulated in the form of oral preparations such as powders, granules, capsules, tablets, and aqueous suspensions, preparations for external use, suppositories, and sterile injectable solutions, respectively, according to conventional methods, and used. However, the pharmaceutical composition is not limited thereto. The pharmaceutical composition of the present invention may further comprise a pharmaceutically acceptable carrier. As the pharmaceutically acceptable carrier, a binder, a glidant, a disintegrant, an excipient, a solubilizer, a dispersant, a stabilizer, a suspending agent, a pigment, a flavor, and the like may be used for oral administration; a buffer, a preserving agent, a pain-relieving agent, a solubilizer, an isotonic agent, a stabilizer, and the like may be used in admixture for injections; and a base, an excipient, a lubricant, a preserving agent, and the like may be used for topical administration. The preparations of the pharmaceutical composition of the present invention may be prepared in various ways by being mixed with the pharmaceutically acceptable carrier as described above. For example, for oral administration, the pharmaceutical composition may be formulated in the form of tablets, troches, capsules, elixirs, suspensions, syrups, wafers, or the like. For injections, the pharmaceutical composition may be formulated in the form of unit dosage ampoules or multiple dosage forms. Alternatively, the pharmaceutical composition may be formulated into solutions, suspensions, tablets, capsules, sustained-release preparations, or the like.

Meanwhile, as examples of carriers, diluents, or excipients suitable for making preparations, lactose, dextrose, sucrose, sorbitol, mannitol, xylitol, erythritol, maltitol, starch, gum acacia, alginate, gelatin, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate, mineral oil, or the like may be used. In addition, a filler, an anti-coagulant, a lubricant, a wetting agent, a fragrance, an emulsifier, a preservative, and the like may further be included.

The route of administration of the pharmaceutical composition of the present invention includes, but is not limited to, oral, intravenous, intramuscular, intraarterial, intramedullary, intradural, intracardiac, transdermal, subcutaneous, intraperitoneal, intranasal, intestinal, topical, sublingual, or rectal route. Oral or parenteral administration is preferred.

As used herein, the term "parenteral" includes subcutaneous, intradermal, intravenous, intramuscular, intraarticular, intrabursal, intrasternal, intradural, intralesional, and intracranial injection or infusion techniques. The pharmaceutical composition of the present invention may also be administered in the form of suppositories for rectal administration.

The pharmaceutical composition of the present invention may vary depending on a variety of factors, including activity of a certain compound used, the patient's age, body weight, general health status, sex, diet, time of administration, route of administration, rate of excretion, drug combination, and severity of a certain disease to be prevented or treated. A dose of the pharmaceutical composition may vary depending on the patient's condition, body weight, severity of disease, drug form, route of administration, and duration, and may be appropriately selected by those skilled in the art. The pharmaceutical composition may be administered in an amount of 0.0001 to 50 mg/kg or 0.001 to 50 mg/kg, per day. Administration may be made once a day or several times a day. The dose is not intended to limit the scope of the present invention in any way. The pharmaceutical composition according to the present invention may be formulated in the form of pills, sugar-coated tablets, capsules, liquids, gels, syrups, slurries, or suspensions.

According to still yet another embodiment of the present invention, there is provided a method for preventing or treating cancer, comprising a step of administering, to a target individual, an antigen-presenting cell loaded with a cancer-specific tumor antigen epitope provided in the present invention; and/or an activated T cell.

In the present invention, the cancer may be Epstein-Barr virus (EBV)-positive cancer, including, but not limited to, EBV-positive gastric cancer, EBV-positive cervical cancer, EBV-positive Burkitt's lymphoma, EBV-positive T cell lymphoma, EBV-positive breast cancer, EBV-positive leiomyosarcoma, EBV-positive smooth muscle tumor, EBV-positive Hodgkin lymphoma, EBV-positive nasopharyngeal cancer, or EBV-positive post-transplant lymphoproliferative disorder (PTLD), with EBV-positive gastric cancer being preferred.

Dose, schedule, and route of administration of the antigen-presenting cell loaded with a cancer-specific tumor antigen epitope provided in the present invention or the activated T cell may be determined depending on the size and condition of an individual, and in accordance with standard pharmaceutical practice. Exemplary routes of administration include intravenous, intraarterial, intraperitoneal, intrapulmonary, intravascular, intramuscular, intratracheal, subcutaneous, intraocular, intrathecal, or transdermal route.

A dose of cells administered to an individual may vary depending, for example, on the particular type of cells being administered, the route of administration, and the particular type and stage of cancer being treated. The amount should be sufficient to produce a desirable response, such as a therapeutic response against cancer, but without severe toxicity or adverse events. In some embodiments, the amount of activated T cells or antigen-presenting cells (such as dendritic cells) to be administered is a therapeutically effective amount. In some embodiments, the amount of cells (such as dendritic cells loaded with a cancer-specific tumor antigen epitope or activated T cells) is an amount sufficient to decrease the size of a tumor, decrease the number of cancer cells, or decrease the growth rate of a tumor by any one of at least about 10%, 20%, 30%, 40%, 50%, 60%, 70%, 80%, 90%, 95%, or 100%, as compared with the corresponding tumor size, number of cancer cells, or tumor growth rate in the same individual prior to treatment or as compared with the corresponding activity in other individuals having not received the treatment. The magnitude of effects may be measured using standard methods, such as in vitro assays with purified enzymes, cell-based assays, animal models, or experiments using humans.

In an embodiment of the present invention, the antigen-presenting cells (such as dendritic cells) loaded with a cancer-specific tumor antigen epitope of the present invention may be administrated at a dose of any of $1\times10^5$ to $5\times10^5$, $5\times10^5$ to $1\times10^6$, $1\times10^6$ to $2\times10^6$, $2\times10^6$ to $3\times10^6$, $3\times10^6$ to $4\times10^6$, $4\times10^6$ to $5\times10^6$, $5\times10^6$ to $6\times10^6$, $6\times10^6$ to $7\times10^6$, $7\times10^6$ to $8\times10^6$, $8\times10^6$ to $1\times10^8$, $1\times10^6$ to $3\times10^6$, $3\times10^6$ to $5\times10^6$, $5\times10^6$ to $7\times10^6$, $2\times10^6$ to $4\times10^6$, $1\times10^6$ to $5\times10^6$, or $5\times10^6$ to $1\times10^7$ cells/individual. However, the present invention is not limited thereto.

In another embodiment of the present invention, the antigen-presenting cells (e.g., dendritic cells) loaded with a cancer-specific tumor antigen epitope of the present invention may be administrated at a dose of any of $1\times10^4$ to $5\times10^4$, $5\times10^4$ to $1\times10^5$, $1\times10^5$ to $2\times10^5$, $2\times10^5$ to $4\times10^5$, $4\times10^5$ to $6\times10^5$, $6\times10^5$ to $8\times10^5$, $8\times10^5$ to $1\times10^6$, $1\times10^6$ to $2\times10^6$, $2\times10^6$ to $1\times10^7$, $1\times10^4$ to $1\times10^5$, $1\times10^5$ to $1\times10^6$, $1\times10^6$ to $1\times10$, $1\times10^4$ to $1\times10^6$, or $1\times10^5$ to $1\times10^7$ cells/kg. However, the present invention is not limited thereto.

In addition, in an embodiment of the present invention, the activated T cells of the present invention may be administrated at a dose of any of $1\times10^8$ to $5\times10^8$, $5\times10^8$ to $9\times10^8$, $9\times10^8$ to $1\times10^9$, $1\times10^9$ to $2\times10^9$, $2\times10^9$ to $3\times10^9$, $3\times10^9$ to $4\times10^9$, $4\times10^9$ to $5\times10^9$, $5\times10^9$ to $6\times10^9$, $6\times10^9$ to $1\times10^{10}$, $1\times10^9$ to $3\times10^9$, $3\times10^9$ to $5\times10^9$, $5\times10^9$ to $7\times10^9$, $7\times10^9$ to $1\times10^{10}$, $1\times10^9$ to $5\times10^9$, $5\times10^9$ to $1\times10^{10}$, $3\times10^9$ to $7\times10^9$, $1\times10^{10}$ to $1.5\times10^{10}$, $1\times10^{10}$ to $2\times10^{10}$, or $1\times10^9$ to $1\times10^{10}$ cells/individual. However, the present invention is not limited thereto.

In another embodiment of the present invention, the activated T cells of the present invention may be administrated at a dose of any of $1\times10^7$ to $1\times10^8$, $1\times10^8$ to $2\times10^8$, $2\times10^8$ to $4\times10^8$, $4\times10^8$ to $6\times10^8$, $6\times10^8$ to $8\times10^8$, $8\times10^8$ to $1\times10^9$, $1\times10^9$ to $2\times10^9$, $2\times10^9$ to $4\times10^9$, $4\times10^9$ to $1\times10^{10}$, $2\times10^8$ to $6\times10^8$, $6\times10^8$ to $1\times10^9$, $1\times10^8$ to $2\times10^8$, $2\times10^8$ to $2\times10^9$, $1\times10^7$ to $1\times10^8$, $1\times10^8$ to $1\times10^9$, $1\times10^9$ to $1\times10^{10}$, or $1\times10^7$ to $1\times10^9$ cells/kg. However, the present invention is not limited thereto.

In the present invention, a stabilizer or excipient such as human albumin may be used together with administration of the antigen-presenting cells (such as dendritic cells) loaded with a cancer-specific tumor antigen epitope and/or the activated T cells.

In the present invention, dose and dosing schedule of the antigen-presenting cells (such as dendritic cells) loaded with a cancer-specific tumor antigen epitope and/or the activated T cells may be adjusted over the course of treatment based on the judgment of the administering physician. In some embodiments, the activated T cells may be administered at any time point of about 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, or 1 month after the antigen-presenting cells loaded with a tumor antigen peptide are administered, or may be administered simultaneously with the antigen-presenting cells. However, the present invention is not limited thereto.

In the present invention, administration of the antigen-presenting cells (such as dendritic cells) loaded with a cancer-specific tumor antigen epitope and/or the activated T cell may be done alone or in combination with other therapies, such as surgery, radiation therapy, gene therapy, immunotherapy, bone marrow transplantation, stem cell transplantation, hormone therapy, targeted therapy, cryotherapy, ultrasound therapy, photodynamic therapy, chemotherapy, or the like. Additionally, a person having a greater risk of developing a proliferative disease may receive treatments to inhibit and/or delay development of the disease.

Advantageous Effects of Invention

The antigen-presenting cell, that is, dendritic cell, loaded with an Epstein-Barr virus (EBV)-positive cancer-specific tumor antigen epitope provided in the present invention enables rapid and effective induction of differentiation and proliferation of cancer antigen-specific T cells, preferably memory T cells, and the memory T cells thus activated can treat an Epstein-Barr virus (EBV)-positive cancerous or neoplastic condition or prevent recurrence, progression, or metastasis of cancer while avoiding the defense mechanism of cancer cells.

In the conventional adoptive T cell therapies, it takes a long time of 3 to 6 months to produce a large number of T cells for treatment of cancer patients, which poses a big problem in the cell production process in immune cell therapy. However, according to the present invention, $10^9$ autologous memory T cells, which should be used for patient treatment, can be produced within three weeks, and cost reduction and minimized infection risk factors to external contaminants can be achieved. Accordingly, according to the present invention, there is provided a technique that can be applied to terminal cancer patients because such a technique makes rapid therapeutic approaches available for a larger number of solid cancer patients.

BRIEF DESCRIPTION OF DRAWINGS

FIG. 1 illustrates results obtained by performing ELIS-POT on respective EBNA-1-derived neoepitopes to identify degree of T cell activation caused by such neoepitopes in SNU719 cell line according to an embodiment of the present invention.

FIG. 2 illustrates results obtained by performing ELIS-POT on respective EBNA-1-derived neoepitopes to identify degree of T cell activation caused by such neoepitopes in EBV-infected MKN74 cell line according to an embodiment of the present invention.

FIG. 3 illustrates results obtained by performing ELIS-POT on respective LMP-2A-derived neoepitopes to identify degree of T cell activation caused by such neoepitopes in SNU719 cell line according to an embodiment of the present invention.

FIG. 4 illustrates results obtained by performing ELIS-POT on respective LMP-2A-derived neoepitopes to identify degree of T cell activation caused by such neoepitopes in EBV-infected MKN74 cell line according to an embodiment of the present invention.

FIG. 5 illustrates results obtained by performing Cr51 release assay on each of three neoepitopes, which have been selected from EBNA-1-derived neoepitopes, in SNU-719 cell line, depending on HLA type, to identify targeted cancer cell-killing activity of EBV-positive gastric cancer cell antigen, caused by human-derived memory T cells produced according to an embodiment of the present invention.

FIG. 6 illustrates results obtained by performing Cr51 release assay on each of three neoepitopes, which have been selected from EBNA-1-derived neoepitopes, in EBV-infected MKN74 cell line, depending on HLA type, to identify targeted cancer cell-killing activity of EBV-positive gastric cancer cell antigen, caused by human-derived memory T cells produced according to an embodiment of the present invention.

FIG. 7 illustrates results obtained by performing Cr51 release assay on each of three neoepitopes, which have been selected from LMP-2A-derived neoepitopes, in SNU-719 cell line, depending on HLA type, to identify targeted cancer cell-killing activity of EBV-positive gastric cancer cell antigen, caused by human-derived memory T cells produced according to an embodiment of the present invention.

FIG. 8 illustrates results obtained by performing Cr51 release assay on each of three neoepitopes, which have been selected from LMP-2A-derived neoepitopes, in EBV-infected MKN74 cell line, depending on HLA type, to identify targeted cancer cell-killing activity of EBV-positive gastric cancer cell antigen, caused by human-derived memory T cells produced according to an embodiment of the present invention.

FIG. 9 illustrates results obtained by performing Cr51 release assay on each of three selected EBNA-1-derived neoepitopes in EBV-negative MKN74 cell line, to identify cancer cell specificity of such neoepitopes among EBV-positive gastric cancer cell antigens, caused by human-derived memory T cells produced according to an embodiment of the present invention.

FIG. 10 illustrates results obtained by performing Cr51 release assay on each of three selected EBNA-1-derived neoepitopes in EBV-negative MKN74 cell line, to identify cancer cell specificity of such neoepitopes among EBV-positive gastric cancer cell antigens, caused by human-derived memory T cells produced according to an embodiment of the present invention.

FIG. 11 illustrates results obtained by performing Cr51 release assay on each of three selected LMP-2A-derived neoepitopes in EBV-negative MKN74 cell line, to identify cancer cell specificity of such neoepitopes among EBV-positive gastric cancer cell antigens, caused by human-derived memory T cells produced according to an embodiment of the present invention.

FIG. 12 illustrates results obtained by performing Cr51 release assay on each of three selected LMP-2A-derived neoepitopes in EBV-negative MKN74 cell line, to identify cancer cell specificity of such neoepitopes among EBV-positive gastric cancer cell antigens, caused by human-derived memory T cells produced according to an embodiment of the present invention.

FIG. 13 illustrates experimental results on effects of neoepitope-specific cytotoxic T cells in BALB/c nude mouse xenograft model (SNU-719), to verify an in vivo anticancer effect of EBNA-1-derived neoepitopes according to an embodiment of the present invention.

FIG. 14 illustrates experimental results on effects of neoepitope-specific cytotoxic T cells in BALB/c nude mouse xenograft model (EBV-infected MKN74), to verify an in vivo anticancer effect of EBNA-1-derived neoepitopes according to an embodiment of the present invention.

FIG. 15 illustrates experimental results on effects of neoepitope-specific cytotoxic T cells in BALB/c nude mouse xenograft model (SNU-719), to verify an in vivo anticancer effect of LMP-2A-derived neoepitopes according to an embodiment of the present invention.

FIG. 16 illustrates experimental results on effects of neoepitope-specific cytotoxic T cells in BALB/c nude mouse xenograft model (EBV-infected MKN74), to verify an in vivo anticancer effect of LMP-2A-derived neoepitopes according to an embodiment of the present invention.

DETAILED DESCRIPTION OF INVENTION

According to an embodiment of the present invention, there is provided an Epstein-Barr virus (EBV)-positive cancer-specific tumor antigen neoepitope, represented by any one of SEQ ID NOs: 1 to 184.

According to another embodiment of the present invention, there is provided an antigen-presenting cell (APC) loaded with a cancer-specific tumor antigen neoepitope provided in the present invention.

According to yet another embodiment of the present invention, there is provided a T cell activated by an antigen-presenting cell provided in the present invention.

According to still yet another embodiment of the present invention, there is provided an anticancer vaccine or a pharmaceutical composition for preventing or treating cancer, comprising, as an active ingredient, an antigen-presenting cell loaded with a cancer-specific tumor antigen epitope provided in the present invention; and/or an activated T cell.

Hereinafter, the present invention will be described in more detail by way of examples. These examples are only for describing the present invention in more detail, and it will be apparent to those skilled in the art that according to the gist of the present invention, the scope of the present invention is not limited by these examples.

EXAMPLES

Example 1 Production Method of Autologous Memory T Cells Specific to EBV-Positive Gastric Cancer Cells and Clinical Application Thereof 1. Selection of EBV-Positive Gastric Cancer Cell Antigen Neoepitopes Algorithms for predicting the most important sequence with accumulation of genetic mutations in gastric cancer cells and for predicting epitopes of this sequence which bind to HLA of T cells were developed using bioinformatics and proteomics. As algorithms for predicting neoepitopes, NetMHC and NetCTLpan were used. Here, peptide sequences were identified which are expected to have high binding affinity with various HLA types including HLA-A*1101, HLA-A*0206, HLA-A*3101, HLA-B*5101, HLA-B*4403, HLA-B*5401, HLA-B*5801, and HLA-B*3501, as well as HLA-A*2402, HLA-A*0201, and HLA-A*3303 which are HLA types that Koreans express the most. To this end, existing EBV+gastric cancer cell lines were HLA-typed to investigate the HLA type of each cell line, and neoepitopes having high binding affinity with each HLA type were predicted and identified through NetMHC program for the representative proteins, LMP-2A and EBNA-1 proteins, which are present only in EBV+gastric cancer cells due to EBV virus and cause malignancies. The results are shown in Tables 1 and 2, respectively.

TABLE 1

| Neoepitopes for LMP-2A protein | | | | | | | |
|---|---|---|---|---|---|---|---|
| # ID | SEQ (9mer) | HLA-A*24:02 | HLA-A*02:01 | HLA-A*33:03 | HLA-A*11:01 | HLA-A*02:06 | HLA-A*31:01 |
| LMP2A_SNU-719_1 | MGSLEMVPM (SEQ ID NO: 1) | 27371.8 | 11991.5 | 19548.9 | 21044.7 | 2968.1 | 20300.8 |
| LMP2A_SNU-719_119 | SMNPVCLPV (SEQ ID NO: 2) | 9889.5 | 9.9 | 6933.4 | 4394.9 | 14.9 | 1649.6 |

TABLE 1-continued

| | | | | | | | |
|---|---|---|---|---|---|---|---|
| LMP2A_SNU719_121 | NPVCLPVIV (SEQ ID NO: 3) | 40322.3 | 27033.9 | 31415.9 | 38783.6 | 19110.2 | 38909.2 |
| LMP2A_SNU719_124 | CLPVIVAPY (SEQ ID NO: 4) | 13941.3 | 10007.3 | 11545.2 | 4017.4 | 5530.2 | 10510.1 |
| LMP2A_SNU719_125 | LPVIVAPYL (SEQ ID NO: 5) | 29593.2 | 19280.3 | 23285.5 | 37445.1 | 8770.7 | 30098.9 |
| LMP2A_SNU719_127 | VIVAPYLFW (SEQ ID NO: 6) | 3787.8 | 21911.8 | 24575.2 | 10829.4 | 13529.2 | 16840.6 |
| LMP2A_SNU719_128 | IVAPYLFWL (SEQ ID NO: 7) | 2732.2 | 10.1 | 5448.5 | 8930.6 | 6.7 | 2015.8 |
| LMP2A_SNU719_129 | VAPYLFWLA (SEQ ID NO: 8) | 6485.2 | 2405.6 | 10912 | 20624.5 | 159.1 | 10250.1 |
| LMP2A_SNU719_130 | APYLFWLAA (SEQ ID NO: 9) | 39372.1 | 14186.6 | 22554 | 23424.5 | 5249.7 | 20785.8 |
| LMP2A_SNU719_131 | PYLFWLAAI (SEQ ID NO: 10) | 45.8 | 20451.8 | 20179 | 37721.6 | 12845 | 12993.1 |
| LMP2A_SNU719_132 | YLFWLAAIA (SEQ ID NO: 11) | 36946.9 | 22.5 | 13714.8 | 22720.8 | 67.5 | 15292.2 |
| LMP2A_SNU719_136 | LAAIAASCF (SEQ ID NO: 12) | 11127 | 28133.2 | 32080.5 | 26643.1 | 12921.5 | 32823.8 |

TABLE 1-continued

| | | | | | | | |
|---|---|---|---|---|---|---|---|
| LMP2A_SNU-719_138 | AIAASCFTA (SEQ ID NO: 13) | 30319.9 | 200.5 | 24584.2 | 6731.1 | 71.3 | 12568.3 |
| LMP2A_SNU-719_140 | AASCFTASV (SEQ ID NO: 14) | 25117.4 | 224.6 | 17740.8 | 12369.6 | 32.8 | 11110 |
| LMP2A_SNU-719_144 | FTASVSTVV (SEQ ID NO: 15) | 19464.9 | 88.6 | 13762.4 | 20136.1 | 14.6 | 19810.8 |
| LMP2A_SNU-719_146 | ASVSTVVTA (SEQ ID NO: 16) | 37052.1 | 5560.8 | 32852.6 | 8850.6 | 424.7 | 18831.4 |
| LMP2A_SNU-719_153 | TATGLALSL (SEQ ID NO: 17) | 28638.1 | 14742.6 | 31449.6 | 28040.2 | 4055.3 | 34638 |
| LMP2A_SNU-719_156 | GLALSLLLL (SEQ ID NO: 18) | 18374.7 | 83 | 33237 | 18495.4 | 254.8 | 19863.2 |
| LMP2A_SNU-719_157 | LALSLLLLA (SEQ ID NO: 19) | 35190.6 | 817.2 | 21235.6 | 14830.1 | 83.6 | 15856.8 |
| LMP2A_SNU-719_158 | ALSLLLLAA (SEQ ID NO: 20) | 40341.5 | 157.1 | 31542.6 | 14530.5 | 190 | 17991.5 |
| LMP2A_SNU-719_159 | LSLLLLAAV (SEQ ID NO: 21) | 25009.2 | 295.1 | 14717.7 | 21696.2 | 30.5 | 9125.3 |
| LMP2A_SNU-719_160 | SLLLLAAVA (SEQ ID NO: 22) | 38650.3 | 362.5 | 30858 | 23970.9 | 591.4 | 22057.6 |

TABLE 1-continued

| | | | | | | | |
|---|---|---|---|---|---|---|---|
| LMP2A_SNU-719_162 | LLLAVASS (SEQ ID NO: 23) | 39044.6 | 402.5 | 31171.1 | 21818.6 | 315.9 | 23555.9 |
| LMP2A_SNU-719_163 | LLAVASSY (SEQ ID NO: 24) | 26232.6 | 11237.2 | 17769.4 | 1693.5 | 8474.3 | 15035 |
| LMP2A_SNU-719_165 | AAVASSYAA (SEQ ID NO: 25) | 38779.4 | 7069.2 | 29746.7 | 10683.7 | 397.4 | 19865.3 |
| LMP2A_SNU-719_166 | AVASSYAA (SEQ ID NO: 26) | 39351.2 | 1556.8 | 21477.3 | 6403.6 | 124.8 | 14250.3 |
| LMP2A_SNU-719_168 | ASSYAAAQR (SEQ ID NO: 27) | 40984.7 | 33783 | 367.6 | 173.6 | 25710.5 | 76.6 |
| LMP2A_SNU-719_169 | SSYAAAQRK (SEQ ID NO: 28) | 36886.5 | 31558.3 | 5931.4 | 14.5 | 20818 | 930.3 |
| LMP2A_SNU-719_174 | AQRKLLTPV (SEQ ID NO: 29) | 23509.8 | 882.2 | 24447.6 | 21770.7 | 70 | 5273.4 |
| LMP2A_SNU-719_177 | KLLTPVTVL (SEQ ID NO: 30) | 11776.9 | 93.5 | 28522.5 | 24228.3 | 193.5 | 7097.1 |
| LMP2A_SNU-719_178 | LLTPVTVLT (SEQ ID NO: 31) | 37137.6 | 147.1 | 23494.6 | 22140.1 | 257.4 | 20809.9 |
| LMP2A_SNU-719_180 | TPVTVLTAV (SEQ ID NO: 32) | 37734.2 | 18144.2 | 24195.8 | 32539.5 | 5162.9 | 31765.6 |

TABLE 1-continued

| | | | | | | | |
|---|---|---|---|---|---|---|---|
| LMP2A_SNU-719_183 | TVLTAVVTF (SEQ ID NO: 33) | 1299.4 | 12607.8 | 21331.9 | 12630.8 | 2596 | 17811.8 |
| LMP2A_SNU-719_184 | VLTAVVTFF (SEQ ID NO: 34) | 1880 | 1724.7 | 18858.8 | 13899.4 | 1269.2 | 11444.8 |
| LMP2A_SNU-719_185 | LTAVVTFFA (SEQ ID NO: 35) | 28599.4 | 522 | 4795.7 | 3078.1 | 92.6 | 3678 |
| LMP2A_SNU-719_186 | TAVVTFFAI (SEQ ID NO: 36) | 7615.8 | 3348.3 | 12820.8 | 15877.6 | 134.9 | 13801.6 |
| LMP2A_SNU-719_190 | TFFAICLTW (SEQ ID NO: 37) | 209.6 | 24870.2 | 17421.4 | 26303.1 | 22323.9 | 16909.8 |
| LMP2A_SNU-719_191 | FFAICLTWR (SEQ ID NO: 38) | 31407.7 | 22080.5 | 67.9 | 9575.9 | 20572.3 | 140.7 |
| LMP2A_SNU-719_192 | FAICLTWRI (SEQ ID NO: 39) | 2489.3 | 33.1 | 6603.3 | 20325.8 | 8.7 | 11143.4 |
| LMP2A_SNU-719_207 | SLLFALLAA (SEQ ID NO: 40) | 33552.8 | 28.8 | 22637.9 | 7154.3 | 26.2 | 12754.2 |
| LMP2A_SNU-719_208 | LLFALLAAA (SEQ ID NO: 41) | 39864.6 | 17.1 | 15143.5 | 19287.8 | 22.5 | 11438.6 |
| LMP2A_SNU-719_211 | ALLAAAGGL (SEQ ID NO: 42) | 30890.7 | 238.2 | 33730 | 31528.9 | 425.5 | 22061.4 |

TABLE 1-continued

| | | | | | | | |
|---|---|---|---|---|---|---|---|
| LMP2A_SNU-719_214 | AAAGGLQGI (SEQ ID NO: 43) | 27565 | 3517.1 | 32696.6 | 24960 | 137.2 | 27509.3 |
| LMP2A_SNU-719_218 | GLQGIYVLV (SEQ ID NO: 44) | 19757.3 | 26.7 | 18903.5 | 20338.6 | 89.9 | 6778.5 |
| LMP2A_SNU-719_219 | LQGIYVLVM (SEQ ID NO: 45) | 21973.1 | 8022.8 | 37703.6 | 30905.4 | 2345.8 | 29019 |
| LMP2A_SNU-719_221 | GIYVLVML (SEQ ID NO: 46) | 36065.3 | 151.8 | 21377.9 | 13972.3 | 448.8 | 8123.9 |
| LMP2A_SNU-719_223 | YVLVMLVLL (SEQ ID NO: 47) | 17490.5 | 293.6 | 15156 | 27530.7 | 153.6 | 11887.4 |
| LMP2A_SNU-719_226 | VMLVLLILA (SEQ ID NO: 48) | 35525.8 | 444.6 | 24613.5 | 18421.9 | 674.5 | 10636.3 |
| LMP2A_SNU-719_227 | MLVLLILAY (SEQ ID NO: 49) | 37081.4 | 19470 | 23627.1 | 6144.4 | 16629.6 | 20171.2 |
| LMP2A_SNU-719_228 | LVLLILAYR (SEQ ID NO: 50) | 40296.1 | 15526.5 | 27.5 | 405.9 | 10119.1 | 20.7 |
| LMP2A_SNU-719_229 | VLLILAYRR (SEQ ID NO: 51) | 33407.1 | 15983.6 | 238.7 | 964.6 | 16825.3 | 563 |
| LMP2A_SNU-719_230 | LLILAYRR (SEQ ID NO: 52) | 37733.4 | 194672 | 353 | 3782.7 | 15867.3 | 159.2 |

TABLE 1-continued

| | | | | | | | |
|---|---|---|---|---|---|---|---|
| LMP2A_SNU-719_231 | LILAYRRRW (SEQ ID NO: 53) | 10191.2 | 25457.8 | 25429.9 | 27362.6 | 19540.7 | 17519.7 |
| LMP2A_SNU-719_232 | ILAYRRRWR (SEQ ID NO: 54) | 39845.2 | 28729.1 | 71.9 | 7319.8 | 30463.6 | 29.4 |
| LMP2A_SNU-719_233 | LAYRRRWRR (SEQ ID NO: 55) | 24998.6 | 20425.9 | 7.8 | 424.1 | 14678.8 | 5.2 |
| LMP2A_SNU-719_241 | RLTVCGGIM (SEQ ID NO: 56) | 30154.3 | 7330.9 | 345477 | 24745.1 | 5573.4 | 16855.2 |
| LMP2A_SNU-719_242 | LTVCGGIMF (SEQ ID NO: 57) | 9930 | 15172.7 | 21640.9 | 14515.6 | 3824 | 20535.8 |
| LMP2A_SNU-719_243 | TVCGGIMFL (SEQ ID NO: 58) | 17100.9 | 384.8 | 9819.9 | 8431.6 | 128.5 | 9625.5 |
| LMP2A_SNU-719_246 | GGIMFLACV (SEQ ID NO: 59) | 29382.6 | 2824.6 | 25826.7 | 29467 | 437.1 | 15686.2 |
| LMP2A_SNU-719_248 | IMFLACVLV (SEQ ID NO: 60) | 13468.2 | 33.7 | 7969.8 | 17351.1 | 93.2 | 2903 |
| LMP2A_SNU-719_250 | FLACVLVLI (SEQ ID NO: 61) | 19384.4 | 10.5 | 12112.4 | 24245.6 | 16.8 | 10846 |
| LMP2A_SNU-719_254 | VLVLIVDAV (SEQ ID NO: 62) | 31115.8 | 63.7 | 27382.5 | 29178.3 | 81.1 | 22651.6 |

TABLE 1-continued

| | | | | | | | |
|---|---|---|---|---|---|---|---|
| LMP2A_SNU-719_257 | LIVDAVLQL (SEQ ID NO: 63) | 23873.3 | 143.2 | 25164.7 | 21696.4 | 59.9 | 25241.6 |
| LMP2A_SNU-719_261 | AVLQLSPLL (SEQ ID NO: 64) | 10808.3 | 395.5 | 23133.1 | 13646.3 | 117.1 | 9438.6 |
| LMP2A_SNU-719_263 | LQLSPLLGA (SEQ ID NO: 65) | 32042.4 | 469.3 | 29672.4 | 14340.6 | 29.8 | 15058.9 |
| LMP2A_SNU-719_264 | QLSPLLGAV (SEQ ID NO: 66) | 33550.6 | 49.7 | 21128.2 | 26797.4 | 43.7 | 16755 |
| LMP2A_SNU-719_266 | SPLLGAVTV (SEQ ID NO: 67) | 30117.5 | 17918.9 | 30290.4 | 33256.4 | 7730 | 31488.4 |
| LMP2A_SNU-719_272 | VTVVSMTLL (SEQ ID NO: 68) | 15006.2 | 5526.8 | 18969.7 | 15331.5 | 589.6 | 13347.5 |
| LMP2A_SNU-719_273 | TVVSMTLLL (SEQ ID NO: 69) | 6049.7 | 652.7 | 13530.9 | 7958.2 | 177.7 | 15315.7 |
| LMP2A_SNU-719_274 | VVSMTLLLL (SEQ ID NO: 70) | 8120.1 | 978.1 | 21960 | 10661 | 428 | 13853.2 |
| LMP2A_SNU-719_275 | VSMTLLLLA (SEQ ID NO: 71) | 22765.4 | 920 | 16803.5 | 2487.7 | 79.4 | 5629.8 |
| LMP2A_SNU-719_276 | SMTLLLLAF (SEQ ID NO: 72) | 2867.4 | 5041.4 | 25983.4 | 15082.4 | 3004.4 | 16672.7 |

TABLE 1-continued

| | | | | | | | |
|---|---|---|---|---|---|---|---|
| LMP2A_SNU-719_277 | MTLLLAFV (SEQ ID NO: 73) | 19035.5 | 27.4 | 1099.5 | 4770.9 | 8.4 | 582 |
| LMP2A_SNU-719_278 | TLLLLAFVL (SEQ ID NO: 74) | 12676.6 | 164.2 | 20545 | 25952.5 | 587.5 | 13178.3 |
| LMP2A_SNU-719_280 | LLLAFVLWL (SEQ ID NO: 75) | 24803 | 40 | 23132.4 | 26986.3 | 202.3 | 10568 |
| LMP2A_SNU-719_281 | LLAFVLWLS (SEQ ID NO: 76) | 33242 | 300.2 | 13010.6 | 11757 | 412.4 | 9140.2 |
| LMP2A_SNU-719_296 | TLGAALLTL (SEQ ID NO: 77) | 7510.8 | 95.9 | 31160 | 23852.4 | 183.4 | 22528.4 |
| LMP2A_SNU-719_299 | AALLTLAAA (SEQ ID NO: 78) | 39908.7 | 1586.9 | 28364.3 | 16855.7 | 86.9 | 16521.3 |
| LMP2A_SNU-719_300 | ALLTLAAAL (SEQ ID NO: 79) | 23261.1 | 46.8 | 26860.1 | 27729.8 | 155.2 | 13582.5 |
| LMP2A_SNU-719_302 | LTLAAALAL (SEQ ID NO: 80) | 11578.4 | 949 | 20215.5 | 12875.3 | 129.5 | 13315.3 |
| LMP2A_SNU-719_303 | TLAAALALL (SEQ ID NO: 81) | 6696.7 | 21.8 | 13358.6 | 16222.7 | 28.2 | 11363.2 |
| LMP2A_SNU-719_304 | LAAALALLA (SEQ ID NO: 82) | 36062.2 | 2985.8 | 25515.9 | 15003.8 | 414 | 25095.9 |

TABLE 1-continued

| Name | Sequence | | | | | | |
|---|---|---|---|---|---|---|---|
| LMP2A_SNU-719_306 | AALASLASL (SEQ ID NO: 83) | 16882.4 | 797.7 | 23744.5 | 21892.9 | 49.1 | 10793.2 |
| LMP2A_SNU-719_307 | ALALLASLI (SEQ ID NO: 84) | 14588.2 | 191 | 30081.3 | 19870.7 | 541.2 | 18083.4 |
| LMP2A_SNU-719_308 | LALLASLIL (SEQ ID NO: 85) | 17259.7 | 7925.7 | 33454.2 | 2993.87 | 1744.5 | 29244 |
| LMP2A_SNU-719-31 | YPSASGSYG (SEQ ID NO: 86) | 41679.6 | 39870.2 | 37645.8 | 39333.8 | 32297.5 | 42032 |
| LMP2A_SNU-719_310 | LLASLILGT (SEQ ID NO: 87) | 41604.9 | 74.7 | 29015.5 | 23428.3 | 99.3 | 24439.7 |
| LMP2A_SNU-719_313 | SLILGTLNL (SEQ ID NO: 88) | 12080.2 | 70.6 | 25306.7 | 15799.3 | 170.6 | 16385.8 |
| LMP2A_SNU-719_314 | LILGTLNLT (SEQ ID NO: 89) | 41776.7 | 1274.6 | 27409.7 | 27342.2 | 220.3 | 24829.1 |
| LMP2A_SNU-719_317 | GTLNLTTMF (SEQ ID NO: 90) | 5555.5 | 13923.8 | 23808.1 | 6308.3 | 2682.7 | 9656.2 |
| LMP2A_SNU-719_318 | TLNLTTMFL (SEQ ID NO: 91) | 11744.1 | 70.1 | 13411.5 | 9317.2 | 331.4 | 9132.5 |
| LMP2A_SNU-719_320 | NLTTMFLLM (SEQ ID NO: 92) | 13538.2 | 261.2 | 12244.1 | 16237.1 | 454.7 | 15909.4 |

TABLE 1-continued

| | | | | | | | |
|---|---|---|---|---|---|---|---|
| LMP2A_SNU-719_322 | TTMFLLMLL (SEQ ID NO: 93) | 2651.6 | 248.1 | 1781.8 | 2219 | 48.5 | 1513.6 |
| LMP2A_SNU-719_323 | TMFLLMLLW (SEQ ID NO: 94) | 3988.3 | 16232.3 | 24882.1 | 18622.5 | 13501.9 | 17977.3 |
| LMP2A_SNU-719_325 | FLLMLLWTL (SEQ ID NO: 95) | 8083.8 | 8.9 | 12745.7 | 33192.8 | 13.9 | 7882.1 |
| LMP2A_SNU-719_326 | LLMLLWTLV (SEQ ID NO: 96) | 13488.2 | 26.7 | 7799.5 | 17571.3 | 52.8 | 3052 |
| LMP2A_SNU-719_327 | LMLLWTLVV (SEQ ID NO: 97) | 15787.8 | 31.7 | 15849.6 | 19663.7 | 119.1 | 6864 |
| LMP2A_SNU-719_328 | MLLWTLVVL (SEQ ID NO: 98) | 16912 | 24.7 | 13754 | 24171.7 | 52.5 | 7678.7 |
| LMP2A_SNU-719_329 | LLWTLVVLL (SEQ ID NO: 99) | 22368.6 | 24.7 | 11762 | 26130.3 | 141.6 | 4070.5 |
| LMP2A_SNU-719_345 | CPLTKILLA (SEQ ID NO: 100) | 37670.6 | 21444.6 | 26652.3 | 29420.8 | 10764.3 | 29121.2 |
| LMP2A_SNU-719_350 | ILLARLFLY (SEQ ID NO: 101) | 5233.8 | 3865.6 | 6694.9 | 236 | 2901.5 | 1264.9 |
| LMP2A_SNU-719_351 | LLARLFLYA (SEQ ID NO: 102) | 31672.9 | 34.9 | 11717.7 | 4604.7 | 45.8 | 6011.2 |

TABLE 1-continued

| | | | | | | | |
|---|---|---|---|---|---|---|---|
| LMP2A_SNU-719_354 | RLFLYAL AL (SEQ ID NO: 103) | 6856.4 | 20.3 | 14775.5 | 9547.6 | 92.6 | 2096.5 |
| LMP2A_SNU-719_356 | FLYALALL L (SEQ ID NO: 104) | 11428.5 | 6 | 10051.6 | 14849.5 | 19.6 | 7883.2 |
| LMP2A_SNU-719_357 | LYALALLL L (SEQ ID NO: 105) | 101 | 12176 | 20911.6 | 31716.4 | 6586.9 | 16497.4 |
| LMP2A_SNU-719_358 | YALALLL LA (SEQ ID NO: 106) | 31846.1 | 159.2 | 16022.1 | 14850.3 | 20.8 | 15655.3 |
| LMP2A_SNU-719_360 | LALLLLAS A (SEQ ID NO: 107) | 40372 | 1722.3 | 23602.9 | 27980.2 | 127.2 | 20356.9 |
| LMP2A_SNU-719_361 | ALLLLAS AL (SEQ ID NO: 108) | 25296.6 | 167 | 29618.5 | 30183.4 | 455.9 | 16547.6 |
| LMP2A_SNU-719_362 | LLLLASA LI (SEQ ID NO: 109) | 7740.7 | 55.9 | 20129.3 | 23602.9 | 116.9 | 13531.6 |
| LMP2A_SNU-719_363 | LLLASALI A (SEQ ID NO: 110) | 37708.1 | 263.9 | 35188.7 | 16754.1 | 400.9 | 26159.2 |
| LMP2A_SNU-719_368 | ALIAGGSI L (SEQ ID NO: 111) | 25800.8 | 493.1 | 36320.6 | 28980.7 | 560.1 | 24630.6 |
| LMP2A_SNU-719_373 | GSILQTN FK (SEQ ID NO: 112) | 40801.5 | 35501.6 | 6602.4 | 16.2 | 26128.9 | 791.4 |

TABLE 1-continued

| | | | | | | | |
|---|---|---|---|---|---|---|---|
| LMP2A_SNU-719_381 | KSLSTEFI (SEQ ID NO: 113) | 5507.7 | 2533.5 | 21307.9 | 12976.3 | 221.3 | 3775.2 |
| LMP2A_SNU-719_384 | SSTEFIPNL (SEQ ID NO: 114) | 14988.3 | 2681.8 | 19581.3 | 13178 | 219.9 | 11100.4 |
| LMP2A_SNU-719_388 | FIPNLFCML (SEQ ID NO: 115) | 4505.5 | 72.9 | 10675 | 27973.3 | 19.8 | 14050.6 |
| LMP2A_SNU-719_389 | IPNLFCMLL (SEQ ID NO: 116) | 16916.4 | 10587.1 | 20005.8 | 27848 | 6583.9 | 20799.9 |
| LMP2A_SNU-719_391 | NLFCMLLLI (SEQ ID NO: 117) | 14595.1 | 20.1 | 7777.2 | 14671.3 | 74.9 | 7191.9 |
| LMP2A_SNU-719_395 | MLLLIVAGI (SEQ ID NO: 118) | 22235.9 | 20.4 | 9301.5 | 26251 | 43.9 | 6024.6 |
| LMP2A_SNU-719_397 | LLIVAGILF (SEQ ID NO: 119) | 6873.4 | 7266.6 | 29271.6 | 21315.3 | 4210.1 | 22774.5 |
| LMP2A_SNU-719_398 | LIVAGILFI (SEQ ID NO: 120) | 23654.3 | 75.6 | 18461.8 | 15122.1 | 47.5 | 14693.4 |
| LMP2A_SNU-719_399 | IVAGILFIL (SEQ ID NO: 121) | 6760.8 | 65.7 | 10025.3 | 14721.2 | 34.3 | 6870.5 |
| LMP2A_SNU-719_405 | FILAILTEW (SEQ ID NO: 122) | 5075.9 | 3363.4 | 19730 | 23123.9 | 1176.5 | 21302.8 |

TABLE 1-continued

| | | | | | | | |
|---|---|---|---|---|---|---|---|
| LMP2A_SNU-719_410 | LTEWGSGNR (SEQ ID NO: 123) | 45205.3 | 34231.1 | 404.4 | 1968.7 | 28770.8 | 787.8 |
| LMP2A_SNU-719_418 | RTYGPVFMC (SEQ ID NO: 124) | 13674.3 | 2452.5 | 20810.3 | 7194.6 | 359.6 | 2242.3 |
| LMP2A_SNU-719_419 | TYGPVFMCL (SEQ ID NO: 125) | 43.1 | 20573.4 | 17372.1 | 28767 | 11909.3 | 10962.4 |
| LMP2A_SNU-719_424 | FMCLGGLLT (SEQ ID NO: 126) | 36749.1 | 418.4 | 26159.7 | 27774.5 | 543.7 | 23960.5 |
| LMP2A_SNU-719_425 | MCLGGLLTM (SEQ ID NO: 127) | 25037.6 | 3987 | 27163.8 | 30133.1 | 848.4 | 26216.1 |
| LMP2A_SNU-719_426 | CLGGLLTMV (SEQ ID NO: 128) | 29360.1 | 39.8 | 26562.2 | 29588.7 | 70 | 18962.1 |
| LMP2A_SNU-719_429 | GLLTMVAGA (SEQ ID NO: 129) | 42669.3 | 50.4 | 33575.3 | 27874.2 | 101.9 | 19703.9 |
| LMP2A_SNU-719_430 | LLTMVAGAV (SEQ ID NO: 130) | 37594.5 | 307.4 | 27810.6 | 35011.8 | 519 | 26238 |
| LMP2A_SNU-719_431 | LTMVAGAVW (SEQ ID NO: 131) | 2451.6 | 22223.6 | 21501.8 | 15181.9 | 8332.6 | 17938.6 |
| LMP2A_SNU-719_432 | TMVAGAVWL (SEQ ID NO: 132) | 14694.7 | 81.7 | 20692.6 | 26012.6 | 145.8 | 18008.3 |

TABLE 1-continued

| | | | | | | | |
|---|---|---|---|---|---|---|---|
| LMP2A_SNU-719_433 | MVAGAVWLT (SEQ ID NO: 133) | 21800.9 | 136.2 | 5179.1 | 7819.4 | 24.4 | 7866.6 |
| LMP2A_SNU-719_434 | VAGAVWLTV (SEQ ID NO: 134) | 8593.3 | 2606.6 | 25834.3 | 23105.9 | 411.4 | 17830.3 |
| LMP2A_SNU-719_439 | WLTVMTNTL (SEQ ID NO: 135) | 11823.3 | 106 | 26126.6 | 35724.7 | 248.7 | 26604.7 |
| LMP2A_SNU-719_440 | LTVMTNTLL (SEQ ID NO: 136) | 17661.7 | 3493.6 | 16154 | 19986.5 | 509.9 | 14004.8 |
| LMP2A_SNU-719_442 | VMTNTLLSA (SEQ ID NO: 137) | 31556.9 | 156.8 | 28830.3 | 13858.3 | 115.4 | 18258.8 |
| LMP2A_SNU-719_443 | MTNTLLSAW (SEQ ID NO: 138) | 7290.9 | 20237.4 | 12898.6 | 10001.4 | 8034.8 | 12238.2 |
| LMP2A_SNU-719_446 | TLLSAWILT (SEQ ID NO: 139) | 30273 | 396.9 | 21252 | 15570.9 | 352.7 | 14095.9 |
| LMP2A_SNU-719_447 | LLSAWILTA (SEQ ID NO: 140) | 32764.6 | 32.4 | 24319.4 | 13902.6 | 93.4 | 16585.4 |
| LMP2A_SNU-719_449 | SAWILTAGF (SEQ ID NO: 141) | 4573.1 | 11740.2 | 13701 | 17240.5 | 2700.5 | 8892.1 |
| LMP2A_SNU-719_451 | WILTAGFLI (SEQ ID NO: 142) | 5519.8 | 57.6 | 10388.7 | 17443.7 | 33.4 | 8331.9 |

TABLE 1-continued

| # ID | Peptide | HLA-A*02:01 | HLA-A*24:02 | HLA-A*11:01 | HLA-A*33:03 | HLA-A*01:01 | HLA-A*26:01 |
|---|---|---|---|---|---|---|---|
| LMP2A_SNU-719_452 | ILTAGFLIF (SEQ ID NO: 143) | 769.6 | 2963.6 | 29225.1 | 16621.5 | 1785.3 | 21390.8 |
| LMP2A_SNU-719_453 | LTAGFLIFL (SEQ ID NO: 144) | 16982.4 | 120 | 6508.1 | 8045.4 | 33.2 | 4517.1 |
| LMP2A_SNU-719_457 | FLIFLIGFA (SEQ ID NO: 145) | 42365.3 | 42.7 | 13437.3 | 25165.8 | 52 | 16269.2 |
| LMP2A_SNU-719-459 | IFLIGFALF (SEQ ID NO: 146) | 43.6 | 17773.3 | 13570.3 | 28036.3 | 10285.2 | 10021.4 |
| LMP2A_SNU-719_460 | FLIGFALFG (SEQ ID NO: 147) | 36214.7 | 277.8 | 25993.6 | 27631.3 | 461.1 | 25977.5 |
| LMP2A_SNU-719_461 | LIGFALFGV (SEQ ID NO: 148) | 24962.4 | 20.3 | 11149.9 | 18296.8 | 16.6 | 6672.9 |
| LMP2A_SNU-719_463 | GFALFGVIR (SEQ ID NO: 149) | 35328.8 | 33229.1 | 582.4 | 8108.8 | 32269.6 | 210 |
| LMP2A_SNU-719_466 | LFGVIRCCR (SEQ ID NO: 150) | 28785.7 | 34993.2 | 78.8 | 12351.4 | 33974.7 | 38.3 |
| LMP2A_SNU-719_7 | VPMGAGPPS (SEQ ID NO: 151) | 44669 | 36655.4 | 35264.6 | 36414.6 | 26600.4 | 39954.4 |

| # ID | HLA-B*51:01 | HLA-B*15:01 | HLA-B*44:03 | HLA-B*54:01 | HLA-B*58:01 | HLA-B*35:01 |
|---|---|---|---|---|---|---|
| LMP2A_SNU-719_1 | 19068 | 1393.9 | 31463.2 | 20902.1 | 2627.5 | 164.2 |
| LMP2A_SNU-719_119 | 18869.2 | 443.8 | 11789.2 | 12880.3 | 9730 | 9998.1 |

TABLE 1-continued

| | | | | | | |
|---|---|---|---|---|---|---|
| LMP2A_SNU-719_121 | 1717.4 | 34671.7 | 29524.1 | 241.1 | 30432.6 | 868.3 |
| LMP2A_SNU-719_124 | 32273.1 | 161.2 | 17839.2 | 29638.7 | 17168.1 | 1118.9 |
| LMP2A_SNU-719_125 | 456.5 | 22503.1 | 30741.7 | 337.4 | 11162.4 | 39 |
| LMP2A_SNU-719_127 | 23369.9 | 7172.4 | 14029.8 | 36881.8 | 81 | 14816.8 |
| LMP2A_SNU-719_128 | 14093.9 | 7650 | 29346.4 | 18362.2 | 817.2 | 9877.3 |
| LMP2A_SNU-719_129 | 21984.5 | 20546.3 | 34583.3 | 6597 | 10554.1 | 13623 |
| LMP2A_SNU-719_130 | 9931.9 | 20808.5 | 14633.9 | 25.3 | 33807.9 | 1458.6 |
| LMP2A_SNU-719_131 | 32690.2 | 33027.6 | 35911.5 | 39974.3 | 31558.3 | 38018.7 |
| LMP2A_SNU-719_132 | 26173.6 | 3914.4 | 28938.1 | 5371.4 | 30695.2 | 11886.3 |
| LMP2A_SNU-719_136 | 7996.6 | 63.4 | 14661.8 | 18015.7 | 159.8 | 23.8 |
| LMP2A_SNU-719_138 | 37957.8 | 6013.5 | 31247.4 | 14492.5 | 17396.7 | 21943.8 |
| LMP2A_SNU-719_140 | 9860.7 | 3306.5 | 10812.2 | 5602.1 | 3334.9 | 7527.4 |
| LMP2A_SNU-719_144 | 5884.4 | 1074.2 | 32054.2 | 1077.5 | 1464.4 | 1864.9 |
| LMP2A_SNU-719_146 | 32015 | 3547.8 | 26008.7 | 9458.8 | 3367.2 | 18947.7 |
| LMP2A_SNU-719_153 | 12835.5 | 9454.7 | 26436.6 | 21854.8 | 1695.6 | 404.4 |
| LMP2A_SNU-719_156 | 38515.9 | 4023.7 | 31753.5 | 41085.5 | 15854.4 | 36429.6 |
| LMP2A_SNU-719_157 | 9880.7 | 9979.6 | 25269 | 909.2 | 2060 | 6184.2 |
| LMP2A_SNU-719_158 | 41561.2 | 6626.9 | 26400.6 | 22040.9 | 30091.4 | 31931.3 |
| LMP2A_SNU-719_159 | 7137.4 | 4766.5 | 30342.5 | 3013.5 | 2491.7 | 14007.7 |
| LMP2A_SNU-719_160 | 35597.7 | 6048.7 | 26564.8 | 16328.5 | 32493.8 | 27442.7 |
| LMP2A_SNU-719_162 | 34547.8 | 3633.5 | 37258.4 | 16083.4 | 27538.7 | 18507 |
| LMP2A_SNU-719_163 | 23097.6 | 9.1 | 9592.6 | 23151.9 | 2410.6 | 43 |
| LMP2A_SNU-719_165 | 30204.3 | 3134.7 | 19736.8 | 2929 | 8128.6 | 2163.8 |
| LMP2A_SNU-719_166 | 36692.7 | 1626.1 | 28170.4 | 6365.9 | 23419.2 | 10828.7 |
| LMP2A_SNU-719_168 | 45002.3 | 24905.2 | 34733.7 | 39245.8 | 16532.8 | 34429.5 |
| LMP2A_SNU-719_169 | 35890.1 | 17324.8 | 25977.8 | 33151.5 | 7653 | 29593.5 |
| LMP2A_SNU-719_174 | 29998.4 | 223.9 | 14359.9 | 20829.2 | 28749.6 | 32884.3 |

TABLE 1-continued

| | | | | | | |
|---|---|---|---|---|---|---|
| LMP2A_SNU-719_177 | 26627.8 | 787.1 | 31556.2 | 34200.4 | 6615.5 | 25782.9 |
| LMP2A_SNU-719_178 | 35201.7 | 13541.2 | 40609.9 | 19821.1 | 20510.8 | 21753.5 |
| LMP2A_SNU-719_180 | 1073 | 27088.7 | 32545.2 | 36.9 | 30156.9 | 322.4 |
| LMP2A_SNU-719_183 | 17799.8 | 242.9 | 18087.5 | 26212.1 | 1633.7 | 303.3 |
| LMP2A_SNU-719_184 | 28882.1 | 119.1 | 16654.5 | 35748.6 | 1881.7 | 4251.7 |
| LMP2A_SNU-719_185 | 26352.3 | 14096.2 | 34361.4 | 2279.9 | 2239.6 | 11683.7 |
| LMP2A_SNU-719_186 | 1811.7 | 4697.9 | 20385.3 | 1210.6 | 1509.2 | 1494.9 |
| LMP2A_SNU-719_190 | 23353.2 | 17916.9 | 7418.5 | 35167.8 | 1245.1 | 14681.3 |
| LMP2A_SNU-719_191 | 46034.1 | 39399.8 | 40223.4 | 35558.1 | 43345.9 | 36240.1 |
| LMP2A_SNU-719_192 | 701.1 | 7610.2 | 11525.1 | 679.6 | 323.5 | 1097.9 |
| LMP2A_SNU-719_207 | 36465.9 | 3779.6 | 28678.8 | 11933.9 | 27135 | 21409.4 |
| LMP2A_SNU-719_208 | 25677.4 | 1228.6 | 30349.7 | 2809 | 28533 | 12044.2 |
| LMP2A_SNU-719_211 | 35326.5 | 2099.8 | 24292.3 | 40247.3 | 22863.4 | 30329.1 |
| LMP2A_SNU-719_214 | 18595.5 | 8783.3 | 20531.6 | 26576 | 4561.5 | 20074.7 |
| LMP2A_SNU-719_218 | 39230.9 | 15981.5 | 30612.2 | 35452.4 | 29224.7 | 42802.1 |
| LMP2A_SNU-719_219 | 28065.4 | 128 | 14998.1 | 33933.9 | 18243.6 | 8771 |
| LMP2A_SNU-719_221 | 35575.8 | 16510.1 | 32974.8 | 28738.1 | 24709.3 | 42830.8 |
| LMP2A_SNU-719_223 | 25310.5 | 10525.9 | 35050.4 | 21845.1 | 9208.3 | 13460.3 |
| LMP2A_SNU-719_226 | 38789 | 14580.5 | 34150.1 | 26232 | 28571.3 | 36984.1 |
| LMP2A_SNU-719_227 | 34382.6 | 171.6 | 11119.5 | 26821.8 | 11758.2 | 366.9 |
| LMP2A_SNU-719_228 | 42621.4 | 33896.1 | 40627.1 | 26214.4 | 30730.7 | 34800.3 |
| LMP2A_SNU-719_229 | 45282.7 | 36046.9 | 36738 | 40449.4 | 37005.7 | 40947.5 |
| LMP2A_SNU-719_230 | 45312.6 | 23309 | 39296.3 | 40381.7 | 37662.9 | 38250.9 |
| LMP2A_SNU-719_231 | 21706.8 | 9545.3 | 17745.4 | 34120.6 | 136 | 18865.5 |
| LMP2A_SNU-719_232 | 46423.7 | 30236.3 | 42353.4 | 42222 | 40589.7 | 40637.6 |
| LMP2A_SNU-719_233 | 33940.2 | 28971 | 35978.8 | 22147.5 | 14714.4 | 25705.5 |

TABLE 1-continued

| | | | | | | |
|---|---|---|---|---|---|---|
| LMP2A_SNU-719_241 | 34894.5 | 216.9 | 31598.6 | 33239.9 | 10678.4 | 12768 |
| LMP2A_SNU-719_242 | 20266.8 | 151.3 | 23587 | 21495.2 | 512.1 | 692.3 |
| LMP2A_SNU-719_243 | 28314.3 | 5527.2 | 35112.3 | 30373.4 | 9552.1 | 13224.3 |
| LMP2A_SNU-719_246 | 32710.4 | 17841.9 | 32488.9 | 27472.7 | 21090.2 | 38076.7 |
| LMP2A_SNU-719_248 | 19631.8 | 4985.6 | 28744 | 20012.3 | 20098.4 | 27284.3 |
| LMP2A_SNU-719_250 | 23637.6 | 7804.8 | 28164.6 | 13581.5 | 18267.5 | 19826.9 |
| LMP2A_SNU-719_254 | 25904.3 | 6865.1 | 31934.1 | 18772.4 | 26216.4 | 27905.3 |
| LMP2A_SNU-719_257 | 17736.2 | 1148.6 | 32569.5 | 22865.1 | 6475.4 | 3550.7 |
| LMP2A_SNU-719_261 | 20883.6 | 4239.7 | 18649.1 | 30555 | 4025.1 | 11797.6 |
| LMP2A_SNU-719_263 | 28135.4 | 2373.8 | 17703.8 | 14681.8 | 21815.1 | 27746.3 |
| LMP2A_SNU-719_264 | 26585.2 | 3605.7 | 30283.5 | 19801.6 | 25397.5 | 24460.1 |
| LMP2A_SNU-719_266 | 1526.9 | 29720.3 | 28761.4 | 355 | 27198.2 | 892.6 |
| LMP2A_SNU-719_272 | 21080.7 | 3762.7 | 36890.5 | 30202.3 | 452.5 | 18717.1 |
| LMP2A_SNU-719_273 | 15908.7 | 1878.8 | 25562.4 | 21519.7 | 2484.5 | 3325.5 |
| LMP2A_SNU-719_274 | 19204.7 | 2901.8 | 32228.4 | 28795 | 1653.4 | 11146 |
| LMP2A_SNU-719_275 | 15701.6 | 6979.6 | 21951.2 | 3615.2 | 826.9 | 18865.5 |
| LMP2A_SNU-719_276 | 33160.8 | 60 | 8048.1 | 35866 | 7268.3 | 1565.1 |
| LMP2A_SNU-719_277 | 11617.1 | 11509.4 | 27039.5 | 2957.3 | 2041.4 | 20396.6 |
| LMP2A_SNU-719_278 | 31870.9 | 9836 | 27846.8 | 32047.2 | 21002.6 | 19043.3 |
| LMP2A_SNU-719_280 | 32574.4 | 13364.1 | 29749.2 | 34396.7 | 14753.9 | 32068.7 |
| LMP2A_SNU-719_281 | 42903.1 | 22877.5 | 34893 | 25882.1 | 23769.5 | 32067.4 |
| LMP2A_SNU-719_296 | 30173.3 | 1555.3 | 33269.7 | 37369 | 12634.3 | 20706.8 |
| LMP2A_SNU-719_299 | 23912.1 | 4561.1 | 23387.8 | 2285.5 | 13858.1 | 8526 |
| LMP2A_SNU-719_300 | 30515.3 | 753.6 | 16063.9 | 32101.7 | 21011.9 | 14789.4 |
| LMP2A_SNU-719_302 | 8078.8 | 561.8 | 27998.1 | 10984.6 | 188.7 | 641.6 |
| LMP2A_SNU-719_303 | 26107.4 | 612.3 | 25912.1 | 30321.5 | 10647 | 12400.7 |
| LMP2A_SNU-719_304 | 9761.3 | 5008 | 22831.3 | 743 | 798.5 | 1496.1 |

TABLE 1-continued

| | | | | | | |
|---|---|---|---|---|---|---|
| LMP2A_SNU-719_306 | 13608.2 | 1354.4 | 14455.4 | 17031.9 | 928.5 | 3403.9 |
| LMP2A_SNU-719_307 | 25036 | 3146.9 | 16547.8 | 32603.7 | 12979.9 | 35350.6 |
| LMP2A_SNU-719_308 | 3865.7 | 3163.4 | 29938.1 | 12036 | 436.8 | 600.4 |
| LMP2A_SNU-719-31 | 13480.7 | 25105.7 | 38370.8 | 653.1 | 25946.6 | 290.6 |
| LMP2A_SNU-719_310 | 38239.8 | 10950.6 | 35332.6 | 27090.7 | 26687.8 | 31919.2 |
| LMP2A_SNU-719_313 | 29842.7 | 677.1 | 24228.8 | 35236.8 | 15685.2 | 15131.9 |
| LMP2A_SNU-719_314 | 36325.3 | 20529.8 | 43873.4 | 17673.7 | 30129.5 | 28730.9 |
| LMP2A_SNU-719_317 | 32438.7 | 337.5 | 19058.3 | 36479.3 | 182.7 | 7933.2 |
| LMP2A_SNU-719_318 | 26916.6 | 1882.1 | 25585.3 | 30786 | 12223.1 | 10896.2 |
| LMP2A_SNU-719_320 | 27240.3 | 2283.2 | 19381.3 | 29707.8 | 15477.7 | 3864.1 |
| LMP2A_SNU-719_322 | 18366.4 | 3871.8 | 21160.2 | 13386.7 | 625.4 | 11838.4 |
| LMP2A_SNU-719_323 | 28013.9 | 7739 | 5484.2 | 39287 | 377.9 | 19971.6 |
| LMP2A_SNU-719_325 | 29633 | 9838.9 | 29389.6 | 24180.3 | 18410.8 | 15012.5 |
| LMP2A_SNU-719_326 | 22552.3 | 6274.9 | 22518.5 | 11468.4 | 21324.5 | 27980.5 |
| LMP2A_SNU-719_327 | 15437.3 | 2864 | 29283.3 | 15663.8 | 15936 | 17141 |
| LMP2A_SNU-719_328 | 20823.4 | 1237.6 | 27968.7 | 15626.1 | 11511.6 | 5123.8 |
| LMP2A_SNU-719_329 | 26938.7 | 6287.6 | 30004.3 | 24819.7 | 16723.5 | 22476.8 |
| LMP2A_SNU-719_345 | 3795.9 | 33986.8 | 32242.7 | 40.5 | 27618.4 | 4556.3 |
| LMP2A_SNU-719_350 | 28103.1 | 675.1 | 15314.7 | 31828.5 | 3987.8 | 3393.9 |
| LMP2A_SNU-719_351 | 32842.3 | 4290.9 | 32551.5 | 9100.6 | 20431 | 25441.8 |
| LMP2A_SNU-719_354 | 22423.6 | 352.6 | 17945 | 23931.5 | 8333.2 | 11218.5 |
| LMP2A_SNU-719_356 | 14452.3 | 933.8 | 22566.5 | 14066.6 | 8976 | 7114.4 |
| LMP2A_SNU-719_357 | 27210.3 | 16018.8 | 33860.9 | 34946.7 | 16177.4 | 23396.4 |
| LMP2A_SNU-719_358 | 11348.3 | 9221.5 | 22015.4 | 558.3 | 2741.6 | 2807.8 |
| LMP2A_SNU-719_360 | 12404.7 | 7468.9 | 31337.1 | 726.9 | 8043.6 | 5539.5 |
| LMP2A_SNU-719_361 | 30580.1 | 982.2 | 18787.5 | 32238.5 | 24767.1 | 17945.6 |

TABLE 1-continued

| | | | | | | |
|---|---|---|---|---|---|---|
| LMP2A_SNU-719_362 | 10169.7 | 2337.2 | 27104.5 | 20273.6 | 10813.2 | 22288.7 |
| LMP2A_SNU-719_363 | 28071.2 | 3395.5 | 34432.5 | 11384 | 20770 | 18889.4 |
| LMP2A_SNU-719_368 | 32742.3 | 102.5 | 21901.8 | 34824 | 20077.8 | 14272.5 |
| LMP2A_SNU-719_373 | 43973.3 | 24934.3 | 39868.5 | 40321.4 | 14126.7 | 38027.7 |
| LMP2A_SNU-719_381 | 18540.5 | 8780.4 | 27824.2 | 27091 | 48.4 | 29173.2 |
| LMP2A_SNU-719_384 | 18233.9 | 11500.3 | 25381.8 | 32592.1 | 521 | 12130.1 |
| LMP2A_SNU-719_388 | 18845.9 | 3217.7 | 37974.7 | 17265.7 | 27948.8 | 8245.1 |
| LMP2A_SNU-719_389 | 808.3 | 22119.5 | 23895.3 | 1101.4 | 14068.7 | 298.1 |
| LMP2A_SNU-719_391 | 17987 | 10340.4 | 16613.5 | 17723.3 | 17321.2 | 28299.3 |
| LMP2A_SNU-719_395 | 16888.9 | 5920 | 19812.8 | 13208.7 | 14228.6 | 26095.6 |
| LMP2A_SNU-719_397 | 28410.7 | 114.5 | 19338.1 | 30961 | 7162.9 | 4153.9 |
| LMP2A_SNU-719_398 | 15242 | 4774.9 | 34571.4 | 17750.6 | 7809.7 | 20384.2 |
| LMP2A_SNU-719_399 | 20780.6 | 3961.8 | 33101 | 18325.3 | 1341.3 | 6022.3 |
| LMP2A_SNU-719_405 | 14795.5 | 4255.1 | 11400.4 | 18955.3 | 74 | 1361.9 |
| LMP2A_SNU-719_410 | 43444.1 | 32402.9 | 44760 | 36137.2 | 34919.5 | 29665 |
| LMP2A_SNU-719_418 | 33440.4 | 22294 | 35295.9 | 20698.7 | 1940.2 | 38397.7 |
| LMP2A_SNU-719_419 | 31268.4 | 22881.4 | 30885.4 | 36459.2 | 27367.3 | 23665 |
| LMP2A_SNU-719_424 | 38175.3 | 6987.3 | 39059 | 27342.8 | 32303.8 | 26047.9 |
| LMP2A_SNU-719_425 | 15294.2 | 3697.3 | 26509.3 | 18716.3 | 1800.8 | 227.3 |
| LMP2A_SNU-719_426 | 33113.9 | 18368.6 | 35968.2 | 31684.9 | 29085.3 | 41790.7 |
| LMP2A_SNU-719_429 | 41913.5 | 12690.2 | 31166.7 | 32767.4 | 34065.6 | 41039.7 |
| LMP2A_SNU-719_430 | 18858.1 | 2762.7 | 34930.4 | 14473.4 | 28951.9 | 17382.8 |
| LMP2A_SNU-719_431 | 5820 | 331.9 | 4419.9 | 14170.2 | 3.5 | 575.5 |
| LMP2A_SNU-719_432 | 30304.4 | 1675.5 | 20684.8 | 36242.1 | 12071.7 | 10316.5 |
| LMP2A_SNU-719_433 | 26470.9 | 14570.8 | 28749 | 4146.1 | 5216 | 5224.5 |
| LMP2A_SNU-719_434 | 5520.8 | 11126.7 | 28783.8 | 8098 | 946.5 | 14748.6 |
| LMP2A_SNU-719_439 | 21999.9 | 1453.3 | 31394.8 | 22179.2 | 13818.5 | 2582.2 |

TABLE 1-continued

| | | | | | | |
|---|---|---|---|---|---|---|
| LMP2A_SNU-719_440 | 14075.1 | 1202 | 34902.1 | 18094.4 | 339 | 6061.1 |
| LMP2A_SNU-719_442 | 30682.5 | 1108.2 | 32059.4 | 17305.7 | 16675.9 | 18845.3 |
| LMP2A_SNU-719_443 | 12564 | 770.3 | 3529.2 | 16440 | 4.4 | 383.6 |
| LMP2A_SNU-719_446 | 41198.1 | 22402.5 | 35064.1 | 28311.3 | 32570.2 | 33655.3 |
| LMP2A_SNU-719_447 | 29325.5 | 3688.2 | 31123.2 | 12418.8 | 16408.9 | 19392.4 |
| LMP2A_SNU-719_449 | 10008.4 | 210.4 | 4177.6 | 15491.4 | 309.7 | 149.2 |
| LMP2A_SNU-719_451 | 9748.3 | 10058.9 | 24364.2 | 8275.5 | 7233.1 | 10872.3 |
| LMP2A_SNU-719_452 | 21963.6 | 41.1 | 20551.4 | 32421.1 | 3330.1 | 1209.6 |
| LMP2A_SNU-719_453 | 24710.9 | 6108.3 | 33208.9 | 19951.9 | 1093.2 | 12051.5 |
| LMP2A_SNU-719_457 | 37931.1 | 9963.8 | 38572.6 | 13793.5 | 39126.6 | 29860.5 |
| LMP2A_SNU-719-459 | 27325.6 | 5467.1 | 19946.5 | 32621 | 14748.5 | 7339.5 |
| LMP2A_SNU-719_460 | 36790.5 | 11054.1 | 32861.9 | 25757.5 | 25267.6 | 26034.4 |
| LMP2A_SNU-719_461 | 30790.6 | 17419.9 | 38901.6 | 20134.8 | 18600.8 | 33095.9 |
| LMP2A_SNU-719_463 | 48129.4 | 37637.2 | 36865.8 | 42648.6 | 44000.4 | 40388.2 |
| LMP2A_SNU-719_466 | 46970.9 | 39068.3 | 42482.3 | 39408.7 | 43194.2 | 37968.9 |
| LMP2A_SNU-719_7 | 17537.7 | 28276.4 | 40505.1 | 191.3 | 38119.6 | 337.5 |

TABLE 2

Neoepitopes for EBNA-1 protein

| # ID | SEQ (9mer) | HLA-A*24:02 | HLA-A*02:01 | HLA-A*33:03 | HLA-A*11:01 | HLA-A*02:06 | HLA-A*31:01 |
|---|---|---|---|---|---|---|---|
| EBNA-1_SNU-719_277 | RGRGGSGGR (SEQ ID NO: 152) | 45316.5 | 39680 | 4373 | 18740.2 | 34826.3 | 289.3 |
| EBNA-1_SNU-719_285 | RGRGGSGGR (SEQ ID NO: 153) | 45316.5 | 39680 | 4373 | 18740.2 | 34826.3 | 289.3 |

TABLE 2-continued

| | | | | | | | |
|---|---|---|---|---|---|---|---|
| EBNA-1_SNU-719_293 | RGRGGSGGR (SEQ ID NO: 154) | 45316.5 | 39680 | 4373 | 18740.2 | 34826.3 | 289.3 |
| EBNA-1_SNU-719_302 | RGRGRERAR (SEQ ID NO: 155) | 46032.1 | 42644 | 3895.5 | 29673.7 | 38658.7 | 229.8 |
| EBNA-1_SNU-719_308 | RARGGSRER (SEQ ID NO: 156) | 45029.1 | 39602.4 | 1219 | 10439.7 | 31841.9 | 86.1 |
| EBNA-1_SNU-719_312 | GSRERARGR (SEQ ID NO: 157) | 47184.8 | 41384.4 | 1249.1 | 15361.7 | 37002.5 | 175.9 |
| EBNA-1_SNU-719_316 | RARGRGRGR (SEQ ID NO: 158) | 44722.2 | 39536 | 884.7 | 17784.2 | 33601.8 | 65.1 |
| EBNA-1_SNU-719_320 | RGRGRGEKR (SEQ ID NO: 159) | 44053.2 | 42854.4 | 3516.3 | 22983.4 | 38461.4 | 136.3 |
| EBNA-1_SNU-719_322 | RGRGEKRPR (SEQ ID NO: 160) | 45689.7 | 42293.4 | 4657.9 | 28956.6 | 38106 | 233.2 |
| EBNA-1_SNU-719_336 | SSSSGSPPR (SEQ ID NO: 161) | 42342.4 | 36614.5 | 425.2 | 125.9 | 28232.3 | 177.9 |
| EBNA-1_SNU-719_355 | HPVGDADYF (SEQ ID NO: 162) | 31231.2 | 36176.7 | 33692.8 | 36983.6 | 22741.8 | 41710.8 |
| EBNA-1_SNU-719_409 | KGGWFGKHR (SEQ ID NO: 163) | 42456.6 | 37922.1 | 4856.2 | 10120 | 33694.3 | 124.7 |

TABLE 2-continued

| | | | | | | | |
|---|---|---|---|---|---|---|---|
| EBNA-1_SNU-719_41 | RGRGRGRGR (SEQ ID NO: 164) | 45006.2 | 42700.3 | 3668.5 | 27677.6 | 39018.4 | 188.3 |
| EBNA-1_SNU-719_431 | EGLRVLLAR (SEQ ID NO: 165) | 42050.2 | 37488.5 | 187.6 | 7955.5 | 29022.1 | 987.3 |
| EBNA-1_SNU-719_434 | RVLLARSHV (SEQ ID NO: 166) | 19512.6 | 2581.5 | 11516.2 | 16095.2 | 353.6 | 1075 |
| EBNA-1_SNU-719_436 | LLARSHVER (SEQ ID NO: 167) | 36376.1 | 18739.8 | 116.8 | 577.6 | 17709.7 | 53 |
| EBNA-1_SNU-719_45 | RGRGRGGGR (SEQ ID NO: 168) | 45332.2 | 41211.9 | 3488.8 | 26198.8 | 37068.6 | 236.3 |
| EBNA-1_SNU-719_454 | GVFVYGGSK (SEQ ID NO: 169) | 44626.5 | 27517.3 | 9143.4 | 81.9 | 20473.5 | 1986.2 |
| EBNA-1_SNU-719_462 | KTSLYNLRR (SEQ ID NO: 170) | 34794.6 | 26595.5 | 446.4 | 53.6 | 20319.7 | 18.8 |
| EBNA-1_SNU-719_472 | IALAVPQCR (SEQ ID NO: 171) | 39511.7 | 32880.4 | 527.2 | 2884.4 | 26713.5 | 229.8 |
| EBNA-1_SNU-719_481 | ITPLSRLPF (SEQ ID No: 172) | 1491.1 | 25301 | 24504 | 16803.1 | 10821.1 | 17909.2 |
| EBNA-1_SNU-719_503 | RESIVCYFM (SEQ ID NO: 173) | 13257.4 | 17730.8 | 23507 | 22586.8 | 4054.7 | 14022.8 |

TABLE 2-continued

| | | | | | | | |
|---|---|---|---|---|---|---|---|
| EBNA-1_SNU-719_504 (SEQ ID NO: 174) | ESIVCYFMV | 17345.4 | 5738.8 | 5835.7 | 18953.5 | 465.9 | 9913.9 |
| EBNA-1_SNU-719_505 (SEQ ID NO: 175) | SIVCYFMVF | 2026.1 | 6030.4 | 15283.4 | 5288.3 | 1655.6 | 10406.6 |
| EBNA-1_SNU-719_506 (SEQ ID NO: 176) | IVCYFMVFL | 26724.5 | 521.2 | 7210.1 | 10733.8 | 480.8 | 3174.7 |
| EBNA-1_SNU-719_510 (SEQ ID NO: 177) | FMVFLQTHI | 10141.7 | 16.1 | 10488.4 | 28823.4 | 26.1 | 10274.1 |
| EBNA-1_SNU-719_511 (SEQ ID NO: 178) | MVFLQTHIF | 773.1 | 6982.1 | 6844.4 | 6047.9 | 2152.6 | 8273.3 |
| EBNA-1_SNU-719_513 (SEQ ID NO: 179) | FLQTHIFAE | 34284.9 | 428.3 | 14139.7 | 18590.5 | 402.8 | 12823.6 |
| EBNA-1_SNU-719_514 (SEQ ID NO: 180) | LQTHIFAEV | 17941 | 61.6 | 16078.5 | 25417.3 | 9.8 | 12729.3 |
| EBNA-1_SNU-719_526 (SEQ ID NO: 181) | AIKDLVMTK | 39676.1 | 22195.5 | 2666.4 | 29.4 | 14992.6 | 322.1 |
| EBNA-1_SNU-719_540 (SEQ ID NO: 182) | NIKVTVCSF | 15027.2 | 26519.7 | 16872.7 | 27649.5 | 17243.3 | 20453.6 |
| EBNA-1_SNU-719_544 (SEQ ID NO: 183) | TVCSFDDGV | 40262.6 | 2096.8 | 22454.7 | 24077.5 | 380.9 | 24941.6 |

TABLE 2-continued

| # ID | | HLA-B*51:01 | HLA-B*15:01 | HLA-B*44:03 | HLA-B*54:01 | HLA-B*58:01 | HLA-B*35:01 |
|---|---|---|---|---|---|---|---|
| EBNA-1_SNU-719_558 | FPPMVEGAA (SEQ ID NO: 184) | 43694.8 | 29057.6 | 36446.2 | 42153.1 | 18949.4 | 43126.1 |
| EBNA-1_SNU-719_277 | | 47765.8 | 29769.2 | 45986.8 | 44280.7 | 39982.1 | 43547.6 |
| EBNA-1_SNU-719_285 | | 47765.8 | 29769.2 | 45986.8 | 44280.7 | 39982.1 | 43547.6 |
| EBNA-1_SNU-719_293 | | 47765.8 | 29769.2 | 45986.8 | 44280.7 | 39982.1 | 43547.6 |
| EBNA-1_SNU-719_302 | | 47725.5 | 32620.6 | 45707.5 | 43198 | 39720.8 | 41805.7 |
| EBNA-1_SNU-719_308 | | 45468.3 | 19127.1 | 42510.4 | 37732.6 | 27999.9 | 30362.9 |
| EBNA-1_SNU-719_312 | | 47577.5 | 32963.7 | 43767.7 | 45223 | 37929.5 | 45253.8 |
| EBNA-1_SNU-719_316 | | 45327.3 | 23182.2 | 42450.6 | 38545.9 | 32356.3 | 39243.2 |
| EBNA-1_SNU-719_320 | | 47659.9 | 36580.1 | 45330.7 | 42924.9 | 37426.4 | 44343.5 |
| EBNA-1_SNU-719_322 | | 48265.6 | 33970.3 | 46416.2 | 44423.2 | 39930.2 | 43241.9 |
| EBNA-1_SNU-719_336 | | 43513.7 | 23101.1 | 39692.5 | 36562.7 | 27088.4 | 22741.3 |
| EBNA-1_SNU-719_355 | | 12468.9 | 13575.1 | 25926.7 | 10752.9 | 9492.1 | 13.2 |
| EBNA-1_SNU-719_409 | | 48473.3 | 35691.1 | 44147.2 | 45552.5 | 34497.4 | 44034.7 |
| EBNA-1_SNU-719_41 | | 47327.5 | 33030.8 | 45445.2 | 44144.4 | 39900.9 | 44790.1 |
| EBNA-1_SNU-719_431 | | 43250.4 | 39180.9 | 40538 | 35094.5 | 36902.5 | 29032.2 |
| EBNA-1_SNU-719_434 | | 22726.3 | 5093.3 | 32701.6 | 14056.7 | 7788.7 | 35120.3 |
| EBNA-1_SNU-719_436 | | 45126.7 | 22087.2 | 40498.5 | 35766.4 | 32575.8 | 26860.1 |
| EBNA-1_SNU-719_45 | | 47258.9 | 32002.9 | 45779.3 | 43911.9 | 41157.1 | 44732.4 |

TABLE 2-continued

| | | | | | | |
|---|---|---|---|---|---|---|
| EBNA-1_SNU-719_454 | 41747.3 | 17980.8 | 36473 | 31707.9 | 30633.8 | 30968.7 |
| EBNA-1_SNU-719_462 | 45634.8 | 29342.9 | 38073.8 | 40031.5 | 13160.8 | 39576.3 |
| EBNA-1_SNU-719_472 | 37853.6 | 31599.6 | 37944.3 | 32340.2 | 17579.5 | 24121.8 |
| EBNA-1_SNU-719_481 | 26114.5 | 438.1 | 35685.7 | 33692.8 | 3771.2 | 2754 |
| EBNA-1_SNU-719_503 | 33839.3 | 5262.5 | 440 | 26568.8 | 11335.6 | 16703 |
| EBNA-1_SNU-719_504 | 20573.9 | 28021.1 | 28717.3 | 9180.2 | 7673.5 | 23247.5 |
| EBNA-1_SNU-719_505 | 24843.9 | 52.8 | 11265 | 23057.2 | 8440 | 813.6 |
| EBNA-1_SNU-719_506 | 34592.3 | 12094.1 | 39419 | 32020.9 | 11647.3 | 22473.2 |
| EBNA-1_SNU-719_510 | 10650.8 | 402 | 22139.2 | 16201.6 | 5493.7 | 11412.7 |
| EBNA-1_SNU-719_511 | 4430.3 | 28.8 | 10520 | 7239.1 | 217.3 | 20.3 |
| EBNA-1_SNU-719_513 | 39689 | 12298.9 | 41389.8 | 23759.7 | 38950.5 | 15521.1 |
| EBNA-1_SNU-719_514 | 17980.6 | 1123 | 14996.1 | 11684.8 | 17726.8 | 17732.5 |
| EBNA-1_SNU-719_526 | 44286.5 | 16408 | 35567.3 | 36968.8 | 30457 | 32160.8 |
| EBNA-1_SNU-719_540 | 29037.2 | 154.9 | 24316.2 | 34414.2 | 16844.2 | 1653.5 |
| EBNA-1_SNU-719_544 | 34793.9 | 28022.7 | 35086.1 | 24905.8 | 21011.9 | 27572.1 |
| EBNA-1_SNU-719_558 | 7576.1 | 30308.4 | 45375.9 | 48.7 | 39527.1 | 418.3 |

As shown in Tables 1 and 2 above, through in silico prediction, neoepitopes were identified which have high binding affinity for HLA-A*2402, HLA-A*A0201, HLA-A*3303, HLA-A*1101, HLA-A*0206, HLA-A*3101, HLA-B*5101, HLA-B*4403, HLA-B*5401, HLA-B*5801, or HLA-B*3501, and their binding affinity with respective HLA's was predicted by $IC_{50}$ (nM) values. Sequences present in actual human gastric cancer cells and recognizable by T cells in the body were selected based on their binding affinity with the HLA's. As shown in Table 1, regarding the neoepitopes for LMP-2A, in a case of HLA-A*2402, TYGPVFMCL ($IC_{50}$=43.1 nM), LLWTLVVLL ($IC_{50}$=22368.6 nM), LTEWGSGNR ($IC_{50}$=45205.3 nM) were selected in order of high to low binding affinity therefor, and in a case of HLA-A*3101, LAYRRRWRR ($IC_{50}$=5.2 nM), LTVMTNTLL ($IC_{50}$=14004.8 nM), YPSASGSYG ($IC_{50}$=42032 nM) were selected. In addition, as shown in Table 2, regarding the neoepitopes for EBNA-1, in a case of HLA-A*2402, MVFLQTHIF ($IC_{50}$=773.1 nM), AIKDLVMTK ($IC_{50}$=39676.1 nM), GSRERARGR ($IC_{50}$=47184.8 nM) were selected in order of high to low binding affinity therefor, and in a case of HLA-A*3101, KTSLYNLRR ($IC_{50}$=18.8 nM), RGRGGSGGR ($IC_{50}$=289.3 nM), FPPMVEGAA ($IC_{50}$=43126.1 nM) were selected. The neoepitopes selected as above were synthesized into peptides for the following experiments.

2. ELISPOT Results for T Cells Activated by Dendritic Cells Loaded with Selected Neoepitope PBMCs extracted from healthy human blood were separated into monocytes and leukocytes through flow cytometry, and the monocytes were cultured for 2 days in a culture supplemented with cytokines GM-CSF and IL-4 to differentiate into dendritic cells. In addition, the leukocytes were cultured with anti-CD3/CD28 antibody for 3 days, and then cultured in a culture supplemented with cytokine IL-2. The neoepitope peptide selected as above was transferred to the monocyte-differentiated dendritic cells using electroporation. Subsequently, culture was performed for 2 days to identify that the neoepitope has been expressed on the surface of the dendritic cells. Then, the dendritic cells were co-cultured with the leukocytes, which were cultured in a culture supplemented with anti-CD3/CD28 antibody, at a ratio of 1:20 (dendritic cells:leukocytes). In a case of the co-culture, the culture was mixed with a cytokine cocktail containing both cytokine IL-4 that increases the antigen-presenting function of dendritic cells, and cytokines IL-2 and IL-7 that function to help conversion of T cells into memory cells, and culture was performed. After 16 hours, expression levels of IFN-γ in the T cells thus activated were measured with ELISPOT, and the results are illustrated in FIGS. 1 to 4. Here, for a negative control peptide used in the experiments, the amino acid sequence 9-mer (sequence: GGSRERARG) was employed which is of any EBNA-1 or LMP-2A protein that has not been extracted through NetMHC in EBNA-1 and LMP-2A.

As a result, it was found that the T-cells cultured with dendritic cells loaded with a neoepitope peptide of the present invention secrete much more IFN-γ than the control regardless of binding affinity of the peptide for HLA.

From these results, it was found that in the present invention, cytotoxic T lymphocytes (CTLs) can be activated by the dendritic cells loaded with each of neoepitopes, which have been selected by HLA-A types of respective cell lines in Tables 1 and 2 above, and the thus activated T cells have antigen specificity which enables recognition of the neoepitope that is a neoantigen.

3. Cancer Cell Lysis Effect of T Cells Activated by Dendritic Cells Loaded with Selected Neoepitope In order to select memory T cells to which an antigen had been presented through the dendritic cells after co-culture for 72 hours as in item no. 2 above, a magnetic-activated cell sorter (MACS) capable of extracting T cells secreting cytokine IFN-γ was used to extract EBV antigen-specific memory T cells. The extracted memory T cells were cultured in a culture supplemented with cytokines IL-2, IL-7, and IL-15 to maintain their memory function and increase the number of cells, in which the culture was performed until the memory T cells reach the number of cells that can be injected into mice.

Such activated T cells were co-cultured with SNU-719 cell line, that is, EBV-positive gastric cancer cells, and with EBV-infected MKN74 cell line, to identify lysis of the cancer cells through Cr51 release assay. The results are illustrated in FIGS. 5 to 8. Also, such activated T cells were co-cultured with MKN-74 cell line, that is, EBV-negative gastric cancer cells, to identify lysis of the cancer cells through Cr51 release assay. The results are illustrated in FIGS. 9 to 12. Here, for a negative control peptide used in the experiments, the amino acid sequence 9-mer (sequence: GGSRERARG) was employed which is of any EBNA-1 or LMP-2A protein that has not been extracted through NetMHC in EBNA-1 and LMP-2A.

As a result, it was found that the T cells activated by the neoepitope according to the present invention exhibit excellent lytic ability against EBV-positive gastric cancer cells while exhibiting insignificant lytic ability against EBV-negative gastric cancer cells. In other words, it can be seen that the T cells activated by the dendritic cells loaded with the EBV cancer-specific antigen neoepitope according to the present invention specifically lyse EBV-positive cancer cells.

In addition, the T cells activated by the neoepitope according to the present invention tended to show an increase in the lytic ability, in a mixed-concentration dependent manner, especially in a case of being co-cultured with EBV-positive gastric cancer cells; and it was found that in a case where, among the neoepitopes for respective HLA types, in particular, a neoepitope with higher binding affinity with HLA is used, the activated T cells exhibit a more increased lytic ability against EBV-positive gastric cancer cell line.

4. Identification of In Vivo Anticancer Effect of T Cells Activated by Dendritic Cells Loaded with Selected Neoepitope The EBV-positive gastric cancer cell line, SNU-719 (HLA type: HLA-A*2402), or EBV-infected MKN74 (HLA type: HLA-A*3101), in an amount of $1\times10^7$ cells, was mixed with Matrigel, and the mixture was transplanted into the flank of BALB/c nude mice, to produce a xenograft model. After 4 weeks had elapsed, in a case where cancer tissue is observed, the T cells activated in item no. 2 above, in an amount of $1\times10^7$ cells, were intratumorally injected once a week, and then the size of cancer tissue was measured. The results are illustrated in FIGS. 13 to 16. Here, for a negative control peptide used in the experiments, the amino acid sequence 9-mer (sequence: GGSRERARG) was employed which is of any EBNA-1 or LMP-2A protein that has not been extracted through NetMHC in EBNA-1 and LMP-2A.

As a result, it was found that in a case where activated T cells are subjected to treatment with the neoepitope according to the present invention, the size of EBV-positive gastric cancer is remarkably decreased as compared with the control; and it was found that in a case where, among the neoepitopes for respective HLA types, in particular, a neoepitope with higher binding affinity with HLA is used, a higher rate of decrease in size of gastric cancer is exhibited.

As described above, it was found that all neoepitopes selected by the HLA-A type of each cell line exhibit an excellent effect in enhancing activity of T cells, and that as binding affinity obtained by bioinformatics increases (that is, $IC_{50}$ value decreases), activity of the T cells is enhanced and activity thereof for targeted cancer cell killing is increased. From these results, it is easily predictable that dendritic cells together with the neoepitopes shown in Tables 1 and 2 can be used to enhance activity of T cells, and this also results in an excellent targeted cancer therapeutic effect.

Although specific parts of the present invention have been described in detail as above, it is obvious to those skilled in the art that such a specific description is merely a preferred embodiment, and the scope of the present invention is not limited thereto. Therefore, the substantial scope of the present invention will be defined by the appended claims and equivalents thereof.

INDUSTRIAL APPLICABILITY

The present invention relates to a cancer-specific tumor antigen neoepitope, an antigen-presenting cell loaded with the neoepitope, and a method for activating T cells for cancer treatment using the antigen-presenting cell.

The invention claimed is:

1. A method for preventing or treating cancer, comprising a step of administering to a target individual an antigen-presenting cell loaded with an Epstein-Barr virus (EBV)-positive cancer-specific tumor antigen neoepitope consisting of any one of SEQ ID NOs: 1, 5, 63, 99 and 136.

2. The method according to claim 1, wherein the antigen-presenting cell is a dendritic cell, a B cell, or a macrophage.

3. The method according to claim 1, wherein the antigen-presenting cell promotes proliferation or differentiation of T cells.

4. The method according to claim 1, wherein the Epstein-Barr virus (EBV)-positive cancer-specific tumor antigen neoepitope exhibits binding affinity with at least one of HLA-A, HLA-B, HLA-C, HLA-E, HLA-F, HLA-G, β2-microglobulin, HLA-DPA1, HLA-DPB1, HLA-DQA1, HLA-DQB1, HLA-DRA1, HLA-DRB1, HLA-DRB3, HLA-DRB4, HLA-DRB5, HLA-DM, HLA-DOA, and HLA-DOB loci.

5. The method according to claim 1, wherein the Epstein-Barr virus (EBV)-positive cancer-specific tumor antigen neoepitope exhibits binding affinity with at least one of HLA-A*2402, HLA-A*A0201, HLA-A*3303, HLA-A*1101, HLA-A*0206, HLA-A*3101, HLA-B*5101, HLA-B*4403, HLA-B*5401, HLA-B*5801, and HLA-B*3501.

6. The method according to claim 1, wherein the cancer is EBV-positive gastric cancer, EBV-positive cervical cancer, EBV-positive Burkitt's lymphoma, EBV-positive T cell lymphoma, EBV-positive breast cancer, EBV-positive leiomyosarcoma, EBV-positive smooth muscle tumor, EBV-positive Hodgkin lymphoma, EBV-positive nasopharyngeal cancer, or EBV-positive post-transplant lymphoproliferative disorder (PTLD).

* * * * *